(12) United States Patent
Madsen et al.

(10) Patent No.: US 10,040,893 B2
(45) Date of Patent: *Aug. 7, 2018

(54) POLYMERIC PHOTOINITIATORS AND PHOTOINITIATOR MONOMERS

(71) Applicant: Coloplast A/S, Humlebaek (DK)

(72) Inventors: Niels Joergen Madsen, Alleroed (DK); Petr Sehnal, York (GB); David George Anderson, York (GB); Bo Rud Nielsen, Alleroed (DK)

(73) Assignee: Coloplast A/S, Humlebaek (DK)

( * ) Notice: Subject to any disclaimer, the term of this patent is extended or adjusted under 35 U.S.C. 154(b) by 491 days.

This patent is subject to a terminal disclaimer.

(21) Appl. No.: 14/401,126

(22) PCT Filed: May 14, 2013

(86) PCT No.: PCT/DK2013/050143
§ 371 (c)(1),
(2) Date: Nov. 14, 2014

(87) PCT Pub. No.: WO2013/170857
PCT Pub. Date: Nov. 21, 2013

(65) Prior Publication Data
US 2015/0105488 A1    Apr. 16, 2015

(30) Foreign Application Priority Data

May 16, 2012   (DK) ................................ 2012 70260
Feb. 21, 2013   (DK) ................................ 2013 70098

(51) Int. Cl.
C08G 18/66       (2006.01)
C08F 2/50        (2006.01)
(Continued)

(52) U.S. Cl.
CPC ........ *C08G 18/6688* (2013.01); *C07C 217/54* (2013.01); *C07D 335/16* (2013.01);
(Continued)

(58) Field of Classification Search
CPC ..................... C08G 18/6688; C08G 18/3275; C08G 18/73; C08G 18/758; C08G 18/0814;
(Continued)

(56) References Cited

FOREIGN PATENT DOCUMENTS

EP    1676870 A1    7/2006
FR    2456764    * 12/1980 ............. C09B 57/00
(Continued)

OTHER PUBLICATIONS

Sarker et al.: "Photoinduce Electron-Transfer Reactions: Highly efficient cleavage of C-N bonds and photogeneration of tertiary amines", Journal of Physical Chemistry, vol. 102, 1998, pp. 5375-5382.
Rubinstein et al.: "Antispasmodic ortho-substituted phenoxyalkylamines", Journal of Medical Chemistry, vol. 9, 1966, pp. 804-809.
Sarker et al.: "Tetraorganylborate salts as convenient precursors for photogeneration of tertiary amides", J. Chem. Soc., Perkin Trans. 2, No. 2, 1998, pp. 2315-2321.
(Continued)

*Primary Examiner* — Michael F Pepitone
*Assistant Examiner* — Jessica M Roswell
(74) *Attorney, Agent, or Firm* — Coloplast Corp., Coloplast A/S; Nick Baumann

(57) ABSTRACT

The present invention provides polymeric quaternary ammonium photoinitiators being co-polymers of photoinitiator monomers, as well as quaternary ammonium photoinitiator monomer being valuable intermediates in the preparation of such polymeric photoinitiators. Additionally, there is provided a polyacrylate obtained by radical polymerization of at least one acrylate monomer (Ac) in the presence of such polymeric photoinitiators. In the photoinitiator monomers and polymeric photoinitiators, a photoinitiator moiety and a quaternary ammonium are incorporated into the photoinitiator structure.

32 Claims, 1 Drawing Sheet

(51) Int. Cl.
| | |
|---|---|
| *C09D 4/00* | (2006.01) |
| *C08F 4/04* | (2006.01) |
| *C08G 18/48* | (2006.01) |
| *C08G 18/73* | (2006.01) |
| *C08G 18/75* | (2006.01) |
| *C08G 18/08* | (2006.01) |
| *C08G 18/32* | (2006.01) |
| *C07C 217/54* | (2006.01) |
| *C07D 335/16* | (2006.01) |
| *C08F 2/48* | (2006.01) |

(52) U.S. Cl.
CPC .............. *C08F 2/48* (2013.01); *C08F 2/50* (2013.01); *C08F 4/04* (2013.01); *C08G 18/0814* (2013.01); *C08G 18/3275* (2013.01); *C08G 18/4833* (2013.01); *C08G 18/73* (2013.01); *C08G 18/758* (2013.01); *C09D 4/00* (2013.01)

(58) Field of Classification Search
CPC ..... C08F 2/48; C08F 4/04; C08F 2/50; C07D 335/16; C09D 4/00; C07C 217/54
See application file for complete search history.

(56) References Cited

FOREIGN PATENT DOCUMENTS

| | | |
|---|---|---|
| GB | 919126 A | 2/1963 |
| GB | 952736 A | 3/1964 |
| WO | 2006093371 | 9/2006 |
| WO | 2009147057 A1 | 12/2009 |

OTHER PUBLICATIONS

Wei J et al.: "Novel PU-type polymeric photoinitiator comprising side-chain benzophenone and coinitiator amine for photopolymerization of PU acrylate", Polymers for advanced technologies, XX, XX, vol. 19, No. 12, Jan. 1, 2008, pp. 1763-1770.

Saettone et al.: "Substantivity of sunscreens—preparation and evaluation of some quaternary ammonium benzophenone derivatives", International journal of cosmetic science, vol. 10, 1988, pp. 99-109.

Kunitake T et al.: "DSC Studies of the phase transition behaviour of synthetic bilayer membranes. Opart II bilayer membranes of single-chain and triple-chain amphiphiles", Memoirs of the faculty of engineering, XX, XX, vol. 46, No. 2, Jan. 1, 1986, pp. 245-263.

* cited by examiner

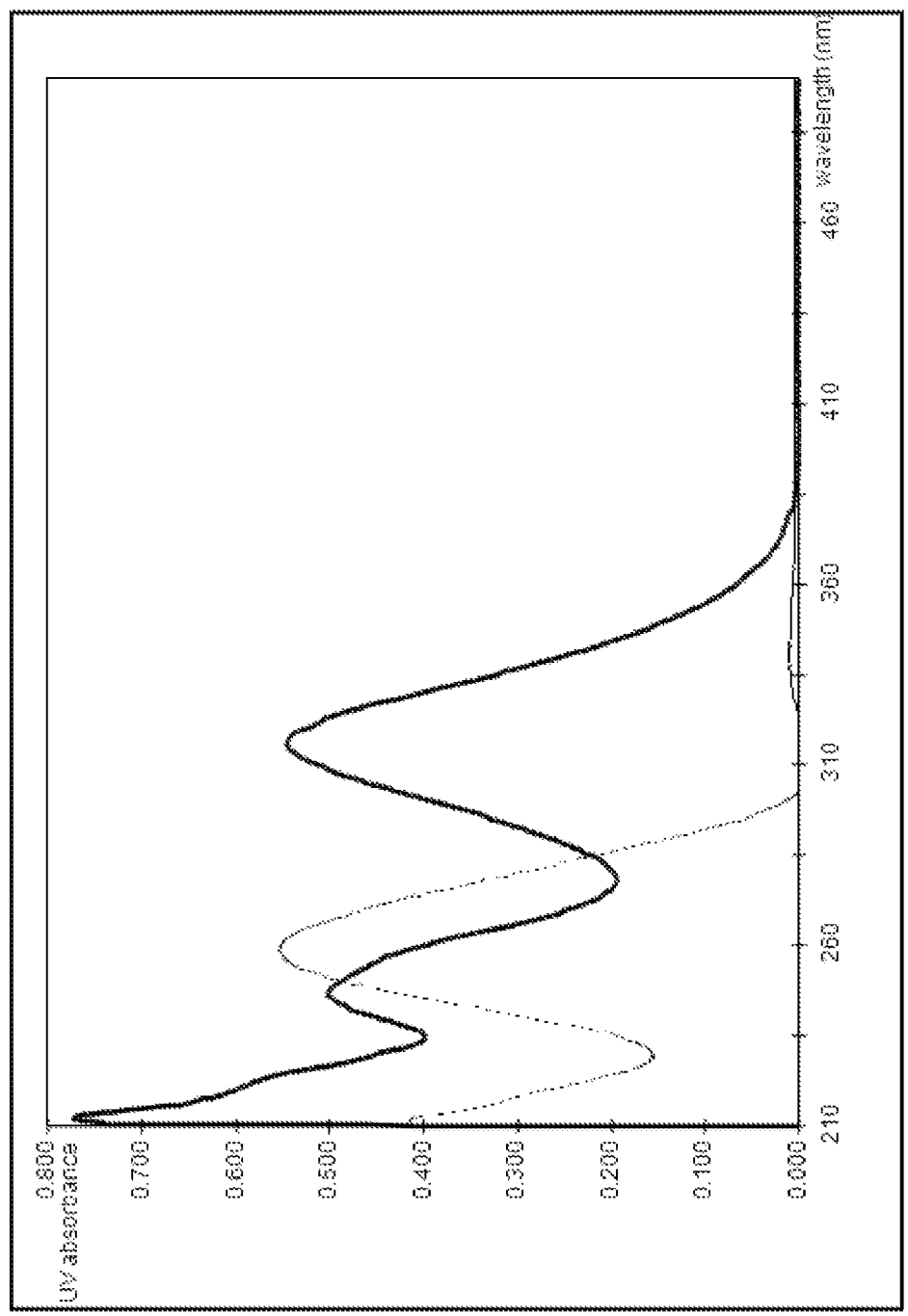

POLYMERIC PHOTOINITIATORS AND PHOTOINITIATOR MONOMERS

FIELD OF THE INVENTION

The present invention relates to polymeric photoinitiators where the photoinitiator moieties are incorporated as pendant groups on the polymeric backbone, as well as photoinitiator monomers being intermediates in the preparation of such polymeric photoinitiators. In the photoinitiator monomers and polymeric photoinitiators, a photoinitiator moiety and a quaternary ammonium group are incorporated into the photoinitiator structure, such that the photoinitiator moieties are present as pendant groups on the polymeric backbone when used in polymers. Additionally the present invention relates to polyacrylates obtained by radical polymerization of at least one acrylate monomer (Ac) in the presence of the polymeric photoinitiator.

BACKGROUND OF THE INVENTION

Curing of coatings through ultraviolet (UV) radiation requires efficient methods of initiating the chemical reaction responsible for the curing process. Curing of polymeric material through generation of radical species upon irradiation with UV light is widely used to produce coatings for medical devices. The paint and lacquer industry also makes use of UV-initiated curing of acrylates, where photoinitiators in many cases are employed. These two examples illustrate the diversity of UV curable coatings.

In a UV curing process, a photoinitiator moiety (low molecular weight or polymer-bound) absorbs UV light and undergoes transition to an excited state, which undergoes further processes which result in the formation of free radicals. This stage is known as initiation.

A polymer photocrosslinking process starts out with long linear polymer chains, and the initiation stage proceeds as described above. Through hydrogen abstraction, the free radicals can be transferred from the photoinitiator to the existing polymer backbone. Hereby forming new carbon-carbon bonds via radical recombination between the polymer chains providing a cross-linking of the before linear polymer chain. Such photoinitiators can be either of low molecular weight or bound in a polymer backbone.

One advantage of the later method is that a linear polymer has considerably different properties than the same type of polymer being cross-linked. The linear polymer may for example be soluble and can then be used in different production processes; it may be e.g. applied on medical devices by spraying or dip coating. The photocrosslinking process may then be initiated afterwards, cross-linking the polymer attaching it to the surface it is applied upon. It will neither dissolve nor melt.

Alternatively, the free radicals formed in the initiation stage may react with unsaturated monomers. This is then called a radical propagation stage. As the unsaturated moieties are transformed to new carbon-carbon bonds, the molecular weight of the radical grows and a new polymer chain is formed, i.e. the polymer is formed from unsaturated monomers and is cross-linked in the same process.

Until recently, polymers designed for use in coatings have relied on photoinitiators with relatively low molecular weight to initiate the cross-linking. In addition, the polymerization reactions for preparing the initial linear polymer often comprise co-reagents and catalysts of the polymerization process which also have relatively low molecular weight. Low molecular weight substances, and their by-products in the polymerization reaction, are generally difficult to remove from the resultant cross-linked polymer, but instead remain within the polymer matrix and diffuse slowly to the surface of the polymer during its lifetime. Over time, low molecular weight substances therefore leach from the polymer into the surrounding environment.

This presents particular problems in the polymers used in the medical field, as patient safety considerations limit the amount and type of substance which can leach from a given polymer. This is especially relevant if the polymer is to be used as a coating or adhesive which is designed to be in contact with the inside or outside of the patient's body. Notably, certain low molecular weight co-reagents and catalysts of polyurethane polymerization are toxic to plants and animals (e.g. dibutyltin dilaurate (DBTDL) or 1,4-diazabicyclo[2.2.2]octane (DABCO)).

Higher molecular weight photoinitiators, in particular polymeric photoinitiators, have comparably higher intrinsic viscosities which most likely result in longer diffusion times through a matrix. Migration of the UV active substances to the surface is therefore diminished when polymeric photoinitiators are used as opposed to lower molecular weight photoinitiators. Scarce literature within the field of polymeric photoinitiators suggests that development of such polymers could lead to novel applications and present solutions for existing needs, such as providing a material with negligent migration of substances to the surface/patient.

The majority of commercial polymeric initiators are based on a linear polymer backbone structures where a photoinitiator species is attached by a linking group to one (WO 96/33156) or both (U.S. Pat. No. 4,602,097) ends of a polymeric chain. While this type of structure provides a cost effective route to production of non-migratable photoinitiators, the linear structures tend to give rise to viscous oils and resinous materials. More problematic, the active photoinitiator weight fraction of the molecule is significantly reduced compared to the parent monomer and therefore a reduction in photoactivity by 50% or more is typically observed.

Polymeric photoinitiators based on a polyurethane main chain have been reported by Wei et al. (Macromolecules 2009, 42, 5486-5491). However, all materials prepared are linear polymeric structures with initiator species within the chain itself. While synthetically available, 'in-chain' polymeric photoinitiators tend to suffer from intrinsically lower photoactivity compared to the photoinitiator monomers. Moreover, linear polymers with in-chain aromatic moieties are prone to give materials with higher degree of crystallinity and much lower solubility compared to other polymer architectures.

Accordingly, it is an object of the present invention to provide polymeric photoinitiators having better photoactivity, in order to efficiently substitute low weight photoinitiators, where migration from the final products are critical. Additionally, it is desirable that such polymeric photoinitiators have good processing properties in the linear polymer state, for use in e.g. coating processes.

Although polymeric photoinitiators have been the subject of much research in recent years, water-soluble polymeric photoinitiators remain elusive. Some cationic thioxanthone macrophotoinitiators were reported by Corrales et al. (3. Photochem. Photobiol. A: Chem. 169 (2005) 95-100). Polycationic benzophenones have also been reported (U.S. Pat. No. 5,714,360), with molecular weights lower than 2000 Da. Detailed photochemical studies of cationic thioxanthones have been reported in a series of papers by Catalina et al. (Eur. Polym. J. 22 (1986) 347-350; Eur. Polym. J. 22 (1986)

871-875; Eur. Polym. J. 29 (1993) 125-130). While low molecular weight cationic photoinitiators discussed above are available, their undesirable properties such as high extractability with water after the completion of the UV curing process have prevented their practical use. Moreover, due to hygroscopic character of ammonium containing low molecular weight photoinitiators, the cured coatings tend to suffer from low weathering stability and water ingress can lead to complete coating disintegration over time. This issue has been addressed in U.S. Pat. No. 4,948,819, where quaternary ammonium benzophenones covalently linked to one acrylate or methacrylate group are described which can be copolymerised with other acrylates during UV curing. Although the authors demonstrate significantly reduced water extractability, the fact that potentially highly toxic and skin-irritating moieties such as (meth)acrylates have to be employed makes them unsuitable for medical coating applications.

Polymers containing multiple charged species (cationic, anionic or betaine-type) in the polymer backbone itself or as part of polymer pendant chains have found many practical uses in the textile, cosmetic (WO94/13724, US2008/0025933), pharmaceutical industries and as ink dispersants (U.S. Pat. No. 7,964,665), however, requiring further additives if they are to be UV cured. In these areas, water soluble polymers can reduce a load on the environment and the human body caused by the usage of organic solvents in most of mainstream polymer solution preparations.

A further object of the present invention is the provision of photoinitiator monomers and polymeric photoinitiators having good solubility or dispersibility in water, which allows for formulating aqueous solutions. Hereby reducing the use of organic solvents, and hence the load on the environment and the human body caused by such usage, both during production and afterwards when final products come in contact with the human body.

The present invention provides polymer photoinitiators in which the photoinitiator moiety itself becomes an integral part of the polymer, and remains so, during and after the polymerization process. Leaching of photoinitiator and photoinitiator by-products is therefore reduced or even eliminated. Polymers likely to improve medical safety are thereby obtained.

Additionally, the present invention provides photoinitiator monomers and polymeric photoinitiators being water soluble, and thereby further facilitates an improved medical safety.

SUMMARY OF THE INVENTION

In a first aspect, the present invention provides intermediates to be used in preparation of polymeric photoinitiators: photoinitiator monomers of the general formula (I):

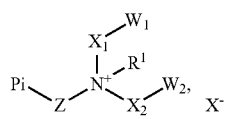

wherein:
Pi is a photoinitiator moiety;
Z is a linker moiety;
$R^1$ is selected from optionally substituted $C_1$-$C_{30}$ alkyl, optionally substituted $C_3$-$C_{30}$ alkenyl, optionally substituted $C_3$-$C_{30}$ alkynyl, optionally substituted $C_3$-$C_{12}$ cycloalkyl, optionally substituted —[($C_1$-$C_6$ alkylene)-O—($C_1$-$C_6$ alkylene)]$_p$—H moiety, optionally substituted heterocyclyl, and optionally substituted aryl;

p is an integer from 1-6;

$X_1$ and $X_2$ are each independently selected from optionally substituted $C_1$-$C_{12}$ alkylene, optionally substituted $C_2$-$C_{12}$ alkenylene, —O—, —S—, —NR$^4$—, —C(=O)—, —C(=NR$^3$)—, —Si(R$^3$)$_2$—O—, optionally substituted $C_3$-$C_8$ cycloalkyl, optionally substituted heterocyclyl, optionally substituted aryl, and combinations thereof;

$X_1$ and $X_2$ or a part thereof may be linked to one another or to linker Z or $R^1$, to form one or more ring structures;

Z, $R^1$, $X_1$ and $X_2$ are selected such that N is a quaternary ammonium;

$R^3$ is H or optionally substituted $C_1$-$C_{12}$ alkyl;
$R^4$ is optionally substituted $C_1$-$C_{12}$ alkyl;
$X^-$ is a counterion, or a negatively charged moiety that is covalently bound to any carbon atom of Pi, Z, $R^1$, $X_1$, $X_2$ or their optional substituents, to form a betaine-type structure;

$W_1$ and $W_2$ are each independently selected —OH (forming a secondary alcohol), —CH$_2$OH (forming a primary alcohol), —NH$_2$, —NHR$^6$, —SH, —Si(OR$^6$)$_2$—H, —SiH(R$^6$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^5$, —NH—C(O)—OR$^5$, and —OC(O)—NHR$^5$;

$R^5$ is H or $C_1$-$C_6$ alkyl; and
$R^6$ is $C_1$-$C_6$ alkyl,
with the proviso that the photoinitiator is not N-(2,4-benzoyl-2,6-dimethylphenoxyethyl)-N,N-bis(2-hydroxyethyl)-N-methylammonium iodide.

The particular structure of the photoinitiator monomers with two functional groups allows it to be incorporated as a monomer into a polyurethane polymer or other polymer types as described further herein. Therefore the monomers of formula (I) are intermediates in the formation of the corresponding polymers. In addition, photoinitiator monomers having the general formula (I) allows formulating highly concentrated aqueous solutions due to the introduced quaternary ammonium moiety (may in the present application also be identified by the term "quaternary amine"). Furthermore, when an alkoxy, amine or thioalkoxy link are used as Z it confers good hydrolytic stability at the same time as providing an improved UV absorption profile due to positive mesomeric effect (M+) of the heteroatoms (N, O or S) in the linker.

In a second aspect, the present invention provides polymeric photoinitiators, being co-polymers of at least one monomer (A) with at least one monomer (B), wherein:
monomer (A) is a photoinitiator monomer (A) of the formula (I):

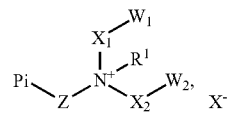

wherein formula (I) is as defined herein for photoinitiator monomers of general formula (I);
monomer (B) comprises at least two functional groups $W_3$ and $W_4$, said $W_3$ and $W_4$ being independently selected from halogen, —OH, —CH$_2$OH, —NH$_2$, —NHR$^{10}$, —SH, —Si(OR$^{10}$)$_2$—H, —SiH(R$^{10}$)$_2$, —C(=O)—

$OSi(R^{10})_3$, —NCO, —NCS, —COOH, —COOR$^{10}$, —COO-aryl, —C(=O)—Cl, —O—C(=O)—Cl, —C(O)—NH$_2$, —C(O)—NHR$^9$, —NH—C(O)—OR$^9$, and —OC(O)—NHR$^9$, wherein R$^9$ is H or C$_1$-C$_6$ alkyl, and wherein R$^{10}$ is C$_1$-C$_6$ alkyl;

wherein W$_1$, W$_2$, W$_3$ and W$_4$ are selected such that—in the co-polymerization of monomers (A) and (B)—W$_1$ reacts with W$_3$ to form a urethane, thiourethane, urea, thiourea, ester, ether, amide, carbonate, allophanate or biuret moiety, and W$_2$ reacts with W$_4$ to form a urethane, thiourethane, urea, thiourea, ester, ether, amide, carbonate, allophanate or biuret moiety.

Due to the presence of the quaternary ammonium moiety in the polymeric photoinitiators of the invention, radical polymerisation of polyacrylates—utilising such polymeric photoinitiators—can be performed in more concentrated aqueous solutions reducing the load on the environment and the human body caused by the usage of an organic solvent. The reduction of relative water content has another advantage—energy saving due to reduced amount of heat needed to evaporate the aqueous solvent after polymerization. When the quaternary ammonium group is introduced in a polymeric photoinitiator, such as polyurethanes, the solid polymer material can be dispersed/dissolved in water without applying strong shearing force, and dispersion stability of the resulting resins in water is comparatively high.

The physical and chemical properties of the polymeric photoinitiators of the present invention can be tailored as required, e.g. by varying the relative amounts and the nature of each monomer (A) or (B).

In a third aspect, the present invention provides a polyacrylate obtained by radical polymerization of at least one acrylate monomer (Ac) in the presence of a polymeric photoinitiator. The polymeric photoinitiator is a co-polymer of at least one monomer (A) with at least one monomer (B), wherein:

monomer (A) is a photoinitiator monomer (A) of the formula (I):

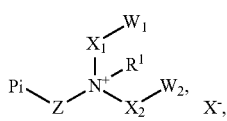

(I)

wherein formula (I) is as defined herein for photoinitiator monomers of general formula (I), according to the first or second aspect of the invention; and monomer (B) is as defined herein for polymeric photoinitiators of the second aspect of the invention.

Polymerization of acrylate monomers in the presence of the polymeric photoinitiators of the invention is rapid, and—as the polymeric photoinitiator remains bound in the polyacrylate—leaching of photoinitiator is reduced or even completely eliminated.

A fourth aspect of the invention relates to polymeric quaternary ammonium photoinitiator monomers obtained by preparing a polymeric photoinitiator being a co-polymer of at least one monomer (A') with at least one monomer (B), and thereafter alkylating a tertiary amine moiety of polymerized (A') with an alkylating agent. Monomer (A') is of formula (I'), which corresponds to formula (I) as described herein above, where R$^1$ is absent and the quaternary ammonium N$^+$ atom is replaced by a tertiary amine group. Accordingly, formula (I'):

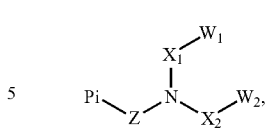

(I')

wherein Pi, Z, X$_1$, X$_2$, W$_1$, and W$_2$, each independently are as described for formula (I), mutatis mutandis.

A fifth aspect of the invention relates to polymeric quaternary ammonium photoinitiators obtained by preparing a polymer being a co-polymer of at least one monomer (A'') with at least one monomer (B), and thereafter alkylating a tertiary amine moiety of polymerized (A'') with an alkylating agent comprising a photoinitiator. Monomer (A'') is of formula (I''), which corresponds to formula (I) as described herein above, except that Pi-Z— is absent and the quaternary ammonium N$^+$ atom is replaced by a tertiary amine group. Accordingly, formula (I''):

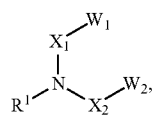

(I'')

wherein R$^1$, X$_1$, X$_2$, W$_1$, and W$_2$, each independently are as described for formula (I), mutatis mutandis.

The invention furthermore provides methods for producing the polymeric photoinitiator; of cross-linking the polymeric photoinitiator by means of UV radiation and/or heat; and for producing a polyacrylate using the polymeric photoinitiator as described herein.

Additionally, the invention provides the use of the polymeric photoinitiator as a photoinitiator of radical polymerization; the use of a polymeric photoinitiator as a photoinitiator of radical polymerization of acrylate monomers; and the use of photoinitiator monomers of formula (I) for preparation of a polymeric photoinitiator.

Further details of the above aspects of the invention are presented in the section "detailed disclosure of the invention" and in the dependent claims.

FIGURES

FIG. 1: shows the UV absorption spectra of Speedcure BMS (4-[(4-methylphenyl)sulfanyl]benzophenone; 0.001% w/v in methanol, 1 cm path length; bold black line) and of Speedcure MBP (4-methylbenzophenone; 0.001% w/v in methanol, 1 cm path length; thin dotted line). Illustrating the advantage of having a heteroatom, here —S—, in the para-position adjacent of a photoinitiator moiety.

DETAILED DISCLOSURE OF THE INVENTION

Photoinitiator monomers of formula (I) or polymeric photoinitiators being copolymers of monomer (A) of formula (I) provides the means for efficient curing of polymeric materials, such as for example coatings on, or materials in, medical devices, paints, or lacquers. The photoinitiator monomers of the present invention, by means of their two functional groups, allow for incorporation by covalent bonds into polymeric materials, hereby limiting or even preventing the migration of the photoinitiator itself, or its by-products, to the surface of the final product encompassing the polymeric material.

As the present photoinitiator monomers or polymeric photoinitiators additionally encompass a quaternary ammonium moiety (quaternary amine), the solubility both of the photoinitiator monomer and the polymeric photoinitiator can be several orders of magnitude higher than the corresponding neutral molecule. The greater aqueous solubility minimized the amount of solvent needed, and it may even be possible to avoid organic solvents, both during polymerization reaction, e.g. radical polymerisation of polyacrylates, and otherwise during production of final products. Hereby reducing the load on the environment and on the human body caused by the usage of an organic solvent.

The reduction of the relative water content has another advantage—energy saving due to reduced amount of heat needed to evaporate the aqueous solvent after polymerization. Additionally, when the quaternary ammonium moiety is introduced in a polymeric photoinitiator, such as polyurethanes, the solid polymer material can be dispersed/dissolved in water without applying strong shearing force, and dispersion stability of the resulting resins in water is comparatively high while post-cure migration of the photoinitiator is minimised due to sufficiently high molecular weight. Due to their polyelectrolyte nature, polymeric photoinitiators of the present invention may form stable micelles in which the quaternary ammonium moieties are exposed to the aqueous phase, while hydrophobic photoinitiator moieties are exposed to the micelle core. It is thus contemplated that quaternary ammonium photoinitiator monomers of the present invention—compared to the non-quaternary counterparts—will stabilize water emulsions prepared from the polymers and acrylate monomers hereby among other increasing shelf-life for commercial products or giving better reproducibility. Additionally, it may reduce the need to use other surfactant additives to stabilise aqueous dispersions of acrylic resins. A further advantage of the present polymers bearing quaternary ammonium moieties is, that they are insensitive to and independent of pH extremes. This is for example not the case if one would attempt to increase the solubility by adding carboxylate or phosphate moieties, which are protonated a low pH and may precipitate from the aqueous solution. In the same manner one could attempt to increase solubility of similar tert-amine polymers or monomers by lowering pH and protonating the amine group, but one would then be dependent on the polymers and the potential products' compatibility with the low pH.

The photoinitiator monomers and polymeric photoinitiators of the present invention are useful in connection with a wide variety of polymers, such as for example polyurethanes, polyureas, polythiourethanes, polythioureas, polydithiourethanes, polyesters, polycarbonates, polyphosphonites, polyphosphonates or polyphosphates.

The photoinitiator monomers of the present invention having two functional groups, provide an advantage when used in polymerization into the above polymers, as two or more different types of monomers may be used in forming a linear polymer chain. Hereby allowing for fine tuning and variation of the physical and chemical properties of the obtained polymers. for example more hydrophobic or more hydrophilic polymers may be desired. The later may be obtained by inserting linkers or varying the polymer chain with monomers, which e.g. enhance and stabilize hydrogen-bonding giving better adhesion of the polymer to polar surfaces. This is especially of relevance when a polymeric polyurethane is to be used as a coating on top of another polyurethane material, hereby giving good adhesion and subsequent good cross-linking, binding the two materials together.

As an example of such a polymeric polyurethane photoinitiator a polyurethane having incorporated polyalkylether chain segments can be mentioned. In the definition of the polymeric photoinitiators of the invention such a polymer may correspond to a monomer (A) being of formula (I), a monomer (B) being a diisocyanate and one or more additional monomers (C) being a polyalkylether macromonomer, e.g. a polypropylene glycol or a polyethylene glycol (PEG), such as PEG 400, PEG 2000, PEG 4000 etc. Further details about suitable monomer (C) are described herein elsewhere. Three examples of polymeric polyurethane photoinitiators of the present invention incorporating three different monomers are shown in Scheme 1. In scheme 1, x may be an integer equal to 1 or greater, preferably, x is between 1 and 100; independently, y may be zero or an integer equal to 1 or greater, preferably, y is between 1 and 100; independently, z may be an integer equal to 1 or greater, preferably, z is between 2 and 10000.

Scheme 1

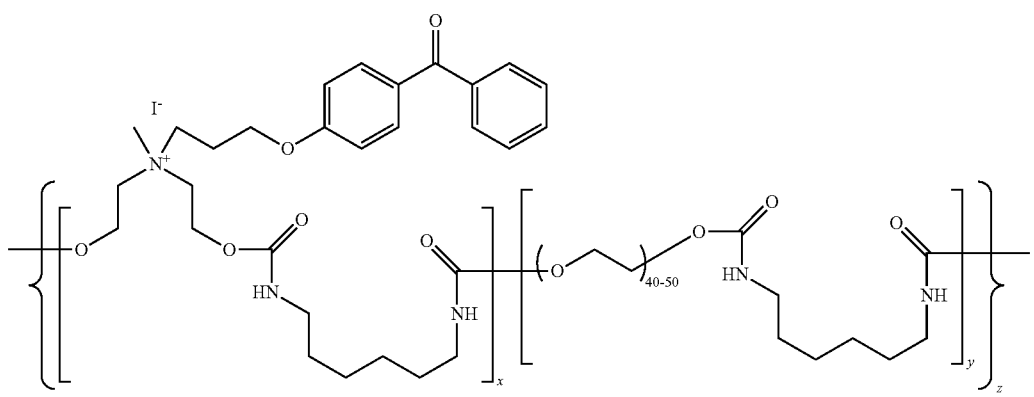

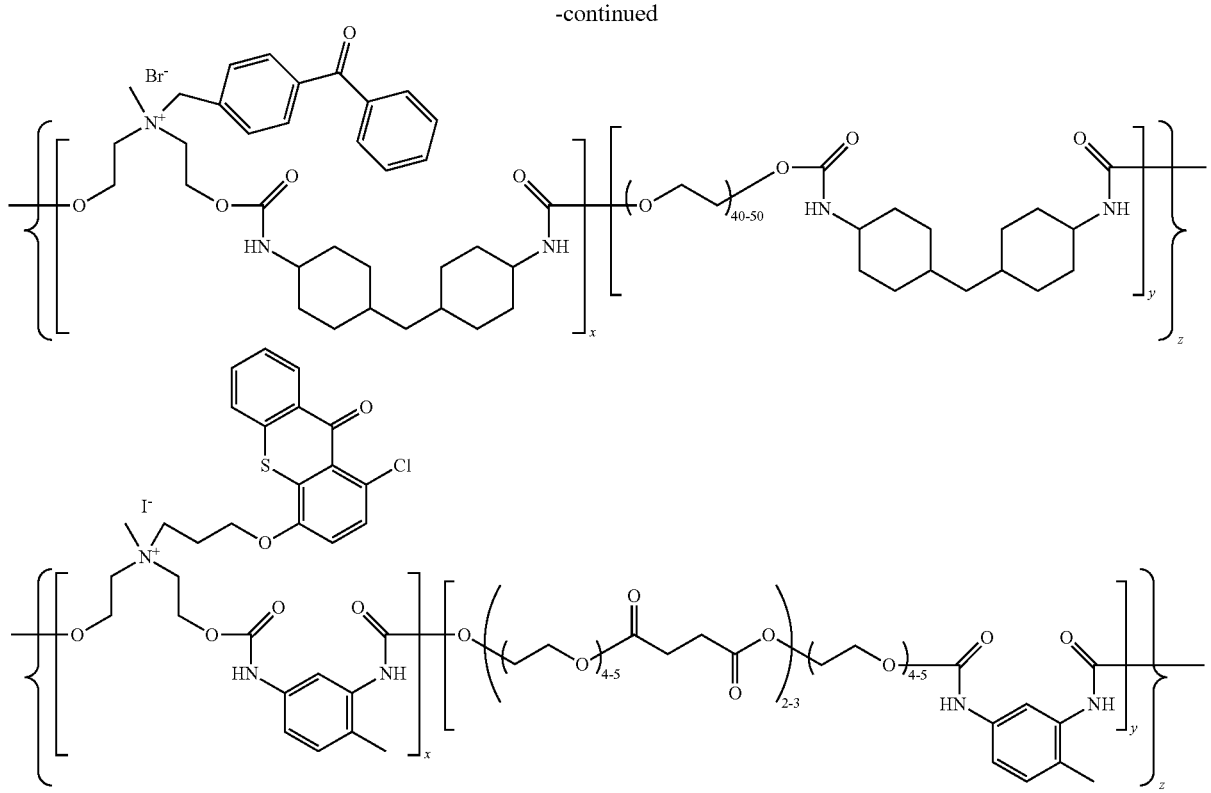

Scheme 1 shows example structures of polymeric polyurethane photoinitiators. In these non-limiting examples every unit of monomer (A) bearing a photoinitiator moiety is flanked by two diisocyanate monomer units (B). Similarly, every unit of monomer (C) in the polymer chain is flanked by two diisocyanate monomer units (B). Thus, the polymer chain is built from randomly interspersed -A-B- and -C-B- units. For example, the polymer chain may contain the following sequence of monomer units -A-B-C-B-C-B-A-B-C-B-A-B-A-B-C-B-C-B-C-B-A-B-. In this manner bonds between monomeric units A and B; C and B are formed by the urethane (carbamate) links —NH—(C=O)—O—.

This possibility of variation is in contrast to known copolymerisable photoinitiator monomers having e.g. one vinylic functional group. Such variety of properties of polymeric photoinitiators may be difficult to achieve when these are constructed from polymer backbones containing only carbon-carbon bonds (e.g. polyacrylates). Despite the fact that many examples of polymeric photoinitiators based on radical co-polymerisation of acrylic monomers (Macromolecules 2012, 45(12), 5237-5246) have been reported in the literature, such approach suffers from disadvantages. Often, radical co-polymerisation of different monomers mixed in a particular ratio does not provide a polymeric chain in which all the co-monomers are randomly interspersed in the same ratio. This is due to variations in the propagation rate for the different co-monomers. As a result, one of the co-monomers may be left largely unreacted at the end of the polymerisation reaction, or a block co-polymer is obtained, in which the less reactive co-monomer units are concentrated around the polymer end rather than randomly distributed throughout the whole polymer chain.

Polyurethanes

A polyurethane (PU) is a polymer consisting of a chain of organic units joined by urethane (carbamate) links —NH—(C=O)—O—. Polyurethanes are formed by the reaction between one monomer having at least two isocyanate functional groups (—NCO), and another monomer or macromonomer (e.g. a PEG) having at least two alcohol (—OH) groups. In their simplest form, due to the nature of the monomers from which they are prepared, polyurethanes comprise alternating A and B monomers (ABABA-BABA . . . ). In the second aspect of the present invention, monomer A may contain at least two —OH groups or two —NCO groups and hence participate in the formation of a polyurethane polymer.

A polyurethane according to the present invention may in this manner also be a polymer having such urethane links in the chain in between macromonomer moieties of e.g. polyether (see e.g. Scheme 1), polyester or polycarbonate. This may for example be the case when a polyurethane comprises A and B monomers and a C macromonomer, where A has two alcohol groups, B has two isocyanate groups, and C is a macromonomer having two terminal alcohol functional groups or two terminal isocyanate functional groups (giving e.g. ABCBABCBCBA when C has two alcohol groups). C could here for instance be a polyalkylether (e.g. PEG) or polyester having two terminal alcohol groups. In a preferred embodiment of the second aspect of the invention the polymeric photoinitiator is a polyurethane.

Polyureas

A polyurea is a polymer consisting of a chain of organic units joined by urea (carbamide) moieties —NH—(C=O)—NH—. Polyureas are typically formed by the reaction between one monomer having at least two isocyanate functional groups (—NCO) or macromonomer having two terminal —NCO groups, and another monomer or macromonomer having at least two amine (—NH₂) groups. Alternatively, polyureas can be formed by the reaction between one monomer having at least two amine (—NH₂) groups, and phosgene (COCl₂) or diphosgene (Cl—CO—OCCl₃).

A polyurea according to the present invention may in this manner also be a polymer having such urea moieties in the chain in between macromonomer moieties of e.g. polyether, polyester or polycarbonate. This may for example be the case when a polyurea comprises A, B and C monomers, where A has two amine groups, B has two isocyanate groups, and C is a polyamine macromonomer having two free terminal amine groups (giving e.g. ABCBABCBCBA) or C is an polyalkylether macromer having two free functional hydroxyl groups (giving e.g. ABCBCBABCBCBA). The first case providing a polyurea polymer having both urea moieties and amine moieties in the chain, and the later case providing a polymer having both polyurea, polyalkylether and polyurethane moieties in the chain. For example, polyether macromonomer moieties are introduced into the main polymer chain when polyetheramines such as Jeffamine D-400, Jeffamine D-2000 or Jeffamine D-4000 etc. are used as macromonomers with two amine (—NH₂) groups. Polyester macromonomer moieties may be introduced into the main polymer chain when amine-terminated polyesters such as those disclosed in U.S. Pat. No. 5,525,683 are used.

Polythiourethanes

A polythiourethane is a generic name for polymers consisting of a chain of organic units joined by —NH—(C=O)—S— or —NH—(C=S)—O— links. The former type of polythiourethanes is formed by the reaction between one monomer having at least two isocyanate functional groups (—NCO), and another monomer having at least two thiol (—SH) groups. The latter type of polythiourethanes is formed by the reaction between one monomer having at least two isothiocyanate functional groups (—NCS), and another monomer having at least two alcohol (—OH) groups.

A polythiourethanes according to the present invention may in this manner also be a polymer having such —NH—(C=O)—S— or —NH—(C=S)—O— links in the chain in between macromonomer moieties of e.g. polyether or polydisulfide. This may for example be the case when a polythiourethane comprises monomers A, B and C, where A has two thiol (—SH) groups, B has two isocyanate groups, and C is a poly(ethylene glycol) dithiol pre-polymer having two free terminal thiol groups (giving e.g. ABCBABCBCBA) or C is an polyalkylether pre-polymer containing disulfide linkages (—S—S—) such as Thiokol® LP-32 or Thiokol® LP-33 two terminal thiol (—SH) functional groups (giving e.g. ABCBCBABCBCBA). The first case providing a polythiourethane polymer having both polythiourea moieties and polyalkylether moieties in the chain, and the later case providing a polymer having both polythiourea, polyalkylether and disulfide moieties in the chain.

Polythioureas

A polythiourea is a polymer consisting of a chain of organic units joined by thiourea (thiocarbamide) moieties —NH—(C=S)—NH—. Polythioureas are typically formed by the reaction between one monomer having at least two isothiocyanate functional groups (—NCS), and another monomer having at least two amine (—NH₂) groups. Alternatively, polythioureas can be formed by the reaction between one monomer having at least two amine (—NH₂) groups, and thiophosgene (S=CCl₂).

A polythiourea according to the present invention may in this manner also be a polymer having such thiourea moieties in the chain in between macromonomer moieties of e.g. polyether, polyester or polycarbonate. This may for example be the case when a polythiourea comprises A, B and C monomers, where A has two amine groups, B has two isothiocyanate groups, and C is a polyamine macromonomer having two free terminal amine groups (giving e.g. ABCBABCBCBA) or C is a polyalkylether macromer having two free functional hydroxyl groups (giving e.g. ABCBCBABCBCBA). The first case providing a polythiourea polymer having both thiourea moieties and amine moieties in the chain, and the latter case providing a polymer having both polythiourea, polyalkylether and polythiourethane moieties in the chain. For example, polyether macromonomer moieties are introduced into the main polymer chain when polyetheramines such as Jeffamine D-400, Jeffamine D-2000 or Jeffamine D-4000 etc. are used as macromonomers with two amine (—NH₂) groups. Polyester macromonomer moieties may be introduced into the main polymer chain when amine-terminated polyesters such as those disclosed in U.S. Pat. No. 5,525,683 are used.

Polydithiourethanes

A polydithiourethane is a polymer consisting of a chain of organic units joined by dithiourethane links —NH—(C=S)—S—. Polydithiourethanes are typically formed by the reaction between one monomer having at least two isothiocyanate functional groups (—NCS), and another monomer having at least two thiol (—SH) groups.

A polydithiourethane according to the present invention may in this manner also be a polymer having such dithiourethane links in the chain in between macromonomer moieties of e.g. polyether or polydisulfide. This may for example be the case when a polydithiourethane comprises monomers A, B and C, where A has two thiol (—SH) groups, B has two isothiocyanate groups, and C is a poly(ethylene glycol) dithiol pre-polymer having two free terminal thiol groups (giving e.g. ABCBABCBCBA) or C is a polyalkylether pre-polymer containing disulfide linkages (—S—S—) such as Thiokol® LP-32 or Thiokol® LP-33 two terminal thiol (—SH) functional groups (giving e.g. ABCBCBAB-CBCBA). The first example case providing a polydithiourethane polymer having both polydithiourea moieties and polyalkylether moieties in the chain, and the later case providing a polymer having both polydithiourea, polyalkylether and disulfide moieties in the chain.

Polyesters

A polyester is a polymer consisting of a chain of organic units joined by ester moieties —(C=O)—O—. Polyesters are typically formed by the reaction between one monomer having at least two carboxylic acid functional groups (—COOH), two carboxylic ester functional groups (—COO-alkyl or —COO-aryl) or two carboxylic acid halides (—COO—X, where X is Cl or Br); and another monomer having at least two alcohol (—OH) groups. The first reaction is an esterification reaction that proceeds in the presence of a Brønsted or Lewis acid catalyst with concomitant removal of water formed during the reaction. The second reaction is a transesterification reaction that proceeds in the presence of a Brønsted or Lewis acid catalyst with concomitant removal a volatile alcohol by-product formed during the reaction. The third reaction proceeds in the presence of a catalytic or stoichiometric quantity of a base such as trialkylamine.

A polyester according to the present invention may in this manner also be a polymer having such ester moieties in the chain in between macromonomer moieties of e.g. a polyether. This may for example be the case when a polyester comprises A, B and C monomers, where A has two alcohol groups, B has two carboxylic acid groups, and C is a polyalkyl ether macromonomer having two terminal hydroxy groups (giving e.g. ABCBABCBCBA). This provides a polyester polymer having both ester moieties and polyether moieties in the chain. For example, polyether macromonomer moieties are introduced into the main polymer chain when polyalkylether, e.g. a polypropylene glycol or a polyethylene glycol (PEG), such as PEG 400, PEG 2000, PEG 4000 etc. are used as monomer C.

Polycarbonate

A polycarbonate is a polymer consisting of a chain of organic units joined by carbonate moieties —O—(C=O)—O—. Polycarbonates are typically formed by the reaction between one monomer having at least two hydroxy functional groups (—OH), and another monomer having at least two chloroformate (—O—(C=O)—Cl) groups. Alternatively, polycarbonates can be formed by the reaction between one monomer having at least two hydroxy functional groups (—OH), and phosgene ($COCl_2$) or diphenyl carbonate (($PhO)_2CO$).

A polycarbonate according to the present invention may in this manner also be a polymer having such carbonate moieties in the chain in between macromonomer moieties of e.g. a polyester or polyamide. This may for example be the case when a polycarbonate comprises monomers A, B and C, where A has two alcohol (—OH) groups, B is ethylenebis (chloroformate), and C is a linear hydroxyl-terminated polyester macromonomer, such as Desmophen 850, (giving e.g. ABCBABCBCBA) or C is a hydroxyl-terminated linear polyamide macromonomer containing amide linkages (—C(O)—NH—) such as those disclosed in patent EP0449419 (giving e.g. ABCBCBABCBCBA). The first case providing a polycarbonate polymer having both carbonate moieties and polyester moieties in the chain, and the later case providing a polymer having both carbonate and amide moieties in the chain.

Polyphosphonites

A polyphosphonite is a polymer consisting of a chain of organic units joined by phosphonite links —O—P(R)—O—, where R is typically methyl or phenyl. Polyphosphonites are typically formed by the reaction between one monomer having at least one dichlorophosphine functional group (—$PCl_2$) or bis(diethylamino)phosphine group (—P($NEt_2)_2$), and another monomer having at least two alcohol (—OH) groups.

Polyphosphonates

A polyphosphonate is a polymer consisting of a chain of organic units joined by phosphonate links —O—P(=O)(R)—O—, where R is typically methyl or phenyl. Polyphosphonates are typically formed by the reaction between one monomer having at least one phosphonoyl dichloride functional group (—P(=O)$Cl_2$), and another monomer having at least two alcohol (—OH) groups.

Polyphosphates

A polyphosphate is a polymer consisting of a chain of organic units joined by phosphate links —O—P(=O)(OR)—O—, where R is typically methyl or phenyl. Polyphosphates are typically formed by the reaction between one monomer having at least one phosphorodichloridate functional group (—O—P(=O)$Cl_2$), and another monomer having at least two alcohol (—OH) groups.

Curing

When using photoinitiator monomers or polymeric photoinitiators according to the present invention, curing is primarily initiated by exposing the photopolymerizable system containing the photoinitiator monomers or the polymeric photoinitiators to high energy irradiation, preferably UV light. The photoinitiated process takes place by methods which are known per se, through irradiation with light or UV irradiation in the wavelength range from 100 to 800 nm, and more usually from 280-800 nm. Irradiation sources which may be used are sunlight or artificial lamps, lasers, or vacuum corona processes. Mercury high-pressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelength. In particular, scattering phenomena are less pronounced at longer wavelength, thus giving a larger penetration depth in the material. Thus, photoinitiators which absorb, and can induce curing, at longer wavelength are of interest. By judicially choosing substituents on the phenone moieties, the absorption spectrum of the photoinitiator can to some extent be red-shifted, which would then facilitate curing at comparatively greater depths.

Photoinitiator Monomers and Photoinitiator Moieties

The present invention provides photoinitiator monomers of general formula (I) together with polymeric photoinitiators being a co-polymer of at least one monomer (A) with at least one monomer (B). Said monomer (A) is a photoinitiator monomer of general formula (I):

(I)

wherein:

Pi is a photoinitiator moiety;

Z is a linker moiety;

$R^1$ is selected from optionally substituted $C_1$-$C_{30}$ alkyl, optionally substituted $C_3$-$C_{30}$ alkenyl, optionally substituted $C_3$-$C_{30}$ alkynyl, optionally substituted $C_3$-$C_{12}$ cycloalkyl, optionally substituted —[($C_1$-$C_6$ alkylene)-O—($C_1$-$C_6$ alkylene)]$_p$—H moiety, optionally substituted heterocyclyl, and optionally substituted aryl;

p is an integer from 1-6;

$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3)_2$—O—, optionally substituted $C_3$-$C_8$ cycloalkyl, optionally substituted heterocyclyl, optionally substituted aryl, and combinations thereof;

$X_1$ and $X_2$ or a part thereof may be linked to one another or to linker Z or $R^1$, to form one or more ring structures;

Z, $R^1$, $X_1$ and $X_2$ are selected such that N is a quaternary ammonium (quaternary amine);

$R^3$ is H or optionally substituted $C_1$-$C_{12}$ alkyl;

$R^4$ is optionally substituted $C_1$-$C_{12}$ alkyl;

$X^-$ is a counterion, or a negatively charged moiety that is covalently bound to any carbon atom of Pi, Z, $R^1$, $X_1$, $X_2$ or their optional substituents, to form a betaine-type structure;

W$_1$ and W$_2$ are each independently selected from —OH (forming a secondary alcohol), —CH$_2$OH (forming a primary alcohol), —NH$_2$, —NHR$^6$, —SH, —Si(OR$^6$)$_2$—H, —SiH(R$^6$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^5$, —NH—C(O)—OR$^5$, and —OC(O)—NHR$^5$;

R$^5$ is H or C$_1$-C$_6$ alkyl; and

R$^6$ is C$_1$-C$_6$ alkyl.

The photoinitiator monomers with the general formula (I) comprise a photoinitiator moiety, Pi, which provides the photoinitiator monomers with the required response to UV radiation; Pi, Z, R$^1$, X$^-$, X$_1$, X$_2$, W$_1$, and W$_2$ will be further described herein below.

GB patent 919,126, published in 1963 relates to pharmaceutically active compounds and reports symphatholytic quaternary ammonium compounds. The patent does not in any way relate to the field of polymeric chemistry or photoinitiation. One of the synthesised compounds is N-(2,4-benzoyl-2,6-dimethylphenoxyethyl)-N,N-bis(2-hydroxyethyl)-N-methylammonium iodide, this specific compound is disclaimed from the first aspect of the invention relating to the photoinitiator monomers of general formula (I) as such. The specific compound may however be included in the second, third, fourth, fifth and further aspects of the invention relating to and/or including polymeric photoinitiators being co-polymers of photoinitiator monomers of formula (I), use of monomers of formula (I) for incorporation into polymers, as well as it may be included in the methods of preparing such polymers and the uses of these.

In one embodiment of the invention Z is a linker -Za-Zb-, then the general formula (I) is of formula (II):

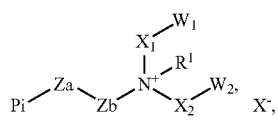

(II)

Pi, Za, Zb, R$^1$, X$_1$, X$_2$, W$_1$, and W$_2$ will be further described herein below.

A photoinitiator is defined as a substance which, on absorption of light, generates reactive species (ions or radicals) and initiates one or several chemical reactions or transformation. One preferred property of the photoinitiator is a good overlap between the emission spectrum of the UV light source and the absorption spectrum of the photoinitiator. Another desired property is a minor or no overlap between the photoinitiator absorption spectrum and the intrinsic combined absorption spectrum of the other components in the polymer matrix. Good compatibility of the photoinitiator with the matrix consisting of material to be cured is also a property of interest.

The photoinitiator moieties of the invention are efficient in transforming light from the UV or visible light source to reactive radicals which can abstract hydrogen atoms and other labile atoms from polymers and hence effect polymerization and cross-linking.

Radical photoinitiator moieties can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. Addition of electron donors is not required but may enhance the overall efficiency of cleavable photoinitiator moieties.

Excited non-cleavable photoinitiators do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. When a non-cleavable photoinitiator moiety is covalently attached as a pendant group via a linker to a polymer chain, there are, in principle, three pathways to form new carbon-carbon bond cross-links as a result of UV irradiation: 1) Coupling of ketyl and aliphatic radicals, 2) dimerisation of ketyl radicals to form a benzopinacol, 3) dimerisation of aliphatic radicals. In cases where the polymeric photoinitiator is a polyurethane with in-chain polyether macromonomer moieties, the hydrogen atom could for instance be abstracted from a —CH$_2$—O— group within the main polymer chain (forming a reactive —ĊH—O— radical). Alternatively, the hydrogen atom could be abstracted from a —CH$_2$— or —CH(R)— group adjacent to the quaternary ammonium moiety of monomer A.

Benzophenones and related ketones such as thioxanthones, xanthones, anthraquinones, fluorenones, dibenzosuberones, benzils, and phenyl ketocoumarins are important examples of non-cleavable photoinitiators, and fall within the definition of photoinitiator moieties according to the present invention. Most amines with a C—H bond in α-position to the nitrogen atom and many thiols will work as electron donors. In a preferred embodiment of the invention, Pi of general formula (I) is a non-cleavable photoinitiator, more preferably a Norrish type II photoinitiator. This due to the goal of the present invention to provide photoinitiator monomers of formula (I) where the migration of by-products from the final polymer product is avoided or at least considerably decreased.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition, the strong UV absorption of the maleimide disappears in the polymer, i.e. maleimide is a photobleaching photoinitiator moiety; this could make it possible to cure thick layers. However, as the maleimides in themself are very reactive, undesired side-reactions may occur and therefore in some embodiments of the present invention the Pi of formula (I) does not include maleimides either alone or when mentioned herein in groups of Pi.

A blend of several photoinitiators may exhibit synergistic properties, as is e.g. described by J. P. Fouassier: "Excited-State Reactivity in Radical Polymerization Photo-initiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethylamino)benzophenone+benzophenone], [benzophenone+2,4,6-trimethylbenzophenone], [thioxanthone+methylthiophenyl morpholinoalkyl ketone]. However, many other beneficial combinations may be envisaged. So, in an embodiment of the invention, the photoinitiator moiety Pi includes at least two different types of photoinitiator moieties. In one embodiment of the invention the polymeric photoinitiator comprises at least two different types of photoinitiator moieties, these may be attached to the same or different monomers (A), preferably these may be attached to two different monomer (A) molecules. Preferably, the absorbance peaks of the different photoinitiator moieties are at different wavelengths, so the total amount of light absorbed by the system increases. The different photoinitiator moieties may be all cleavable, all non-cleavable, or a mixture of cleavable and non-cleavable. Preferably, however, the photoinitiator Pi comprises only one photoinitiator moiety.

UV self-crosslinkable terpolymers based on acrylonitrile, methyl acrylate and a UV sensitive comonomer, acryloyl benzophenone (ABP), have also been reported (A. K. Naskar et al. Carbon 43 (2005) 1065-1072; T. Mukundan et al. Polymer 47 (2006) 4163-4171). The free radicals generated during UV irradiation of the terpolymer have been shown to enhance crosslinking and cyclization of nitrile units within the polymer.

Furthermore, it has recently been found that covalently linked 2-hydroxy-1-(4-(2-hydroxyethoxy)phenyl)-2-methylpropan-1-one, which is commercially available with the trade name Irgacure 2959, and benzophenone in the molecule 4-(4-benzoylphenoxy ethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalenty Bonded Photoinitiators", Proceedings from RadTech Europe 05, Barcelona, Spain, Oct. 18-20 2005, vol. 2, p. 375-81, Vincentz. This shows that different photoinitiator moieties may show significant synergistic effects when they are present in the same oligomer or polymer. Such covalently linked photoinitiator moieties are also within the scope of the present invention.

Photoinitiator moieties (Pi) in Formula (I) may be selected from, but not exclusively restricted to, the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, camphorquinones, silane and derivatives thereof, and maleimides. Of these, preferred photoinitiator moieties may be selected from benzophenones, thioxanthones, benzilketals and phenyl hydroxyalkyl ketones, such as 2-hydroxy-2-methyl-1-phenylpropan-1-ones. More preferred photoinitiator moieties may be selected from benzophenones, and thioxanthones.

In particular, Pi may be a benzophenone having the general formula (III):

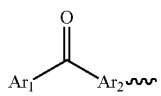

(III)

wherein $Ar_1$ and $Ar_2$ each independently are selected from the same or different aryl, where Z of general formula (I) may be attached at any position on $Ar_2$, i.e. ortho-, meta- or para-position (the attachment point is indicated in formula (III) by the wavy line), and where each aryl independently may be optionally substituted with one or more substituents selected from the groups consisting of —F, —Cl, —Br, —I, —CN, —NO$_2$, —C$_1$-C$_6$ alkyl, —C$_2$-C$_6$ alkenyl, —C$_3$-C$_6$ cycloalkyl, aryl, heterocyclyl, —O—(C$_1$-C$_6$ alkyl), —O—C$_3$-C$_8$ cycloalkyl, —O-aryl, —C(O)—(R$^8$), —C(O)-aryl, —C(O)O—(C$_1$-C$_6$ alkyl), —C(O)O-aryl, —O—C(O)-aryl, —O—C(O)—O—(C$_1$-C$_6$ alkyl), —O—C(O)—O-aryl, —N(C$_1$-C$_6$alkyl)$_2$, —N(C$_1$-C$_6$alkyl)(C$_3$-C$_6$ cycloalkyl), —N(C$_1$-C$_6$alkyl)(aryl), —N(aryl)$_2$, —N(R$^8$)—C(O)—(C$_1$-C$_6$ alkyl), —N(R$^8$)—C(O)-aryl, —C(O)—N(R$^8$)$_2$, —C(O)—N(R$^8$)-aryl, —C(O)—N(aryl)$_2$, —O—C(O)—N(R$^8$)$_2$, —O—C(O)—NH—(C$_1$-C$_6$aryl), —N(R$^8$)—C(O)—O—(C$_1$-C$_6$alkyl), —NH—C(O)—O—(C$_1$-C$_6$aryl), —S(O)—(C$_1$-C$_6$ alkyl), —S(O)-aryl, —SO$_2$—(C$_1$-C$_6$ alkyl), —SO$_2$-aryl, —S—(C$_1$-C$_6$ alkyl) and —S-aryl; wherein R$^8$ is H or C$_1$-C$_6$ alkyl.

In a preferred embodiment of the invention the one or more optional substituents are selected from the group consisting of —F, —Cl, —Br, —I, —CN, —NO$_2$, —C$_1$-C$_6$ alkyl, aryl, —O—(C$_1$-C$_6$ alkyl), —C(O)—O—(C$_1$-C$_6$ alkyl), —S—(C$_1$-C$_6$ alkyl), —S(O)—(C$_1$-C$_6$ alkyl), —SO$_2$—(C$_1$-C$_6$ alkyl), —NH—C(O)—(C$_1$-C$_6$ alkyl), —C(O)—NH—(C$_1$-C$_6$ alkyl), and —C(O)—NH$_2$.

Structures of the formula (III) wherein either or both of $Ar_1$ and $Ar_2$ are substituted in the ortho- or para-position with —OH or —NH$_2$ are known as UV absorbers, giving too low triplet quantum yields ($\Phi_T$), for use as photoinitiators for practical purposes. Additionally, secondary amines (—NH—R) in the ortho- or para-position gives low triplet quantum yields in polar solvents, being less efficient photoinitiators (see Singh et al. J. Phys. Chem. A 104, 2000, 7002; Suppan et al. J. Photochem. Photobiol. A 94, 1996, 145.). Accordingly, Pi in general formula (I) herein does not include compounds of formula (III) having one or more —OH or —NH$_2$ groups in the ortho- or para-position of the aryl rings. Additionally, in one embodiment of the invention photoinitiator monomers of formula (III) does not have a secondary amine (—NHR, where R e.g. is an alkyl group) in the ortho- or para-position of the aryl rings.

Suitably, $Ar_1$ and $Ar_2$ are the same. Preferably $Ar_1$ and $Ar_2$ each independently may be optionally substituted phenyl, where the phenyl each independently may be optionally substituted with one or more substituents selected from the herein immediately above specified group of substituents; and even more preferably both phenyl (i.e. unsubstituted).

In one preferred embodiment of the invention Y (i.e. Z or Za as appropriate) is attached at the para-position on $Ar_2$, as this provides the maximum opportunity for electron interaction with the carbonyl group, and hence maximum stabilisation of the radical formed. In another preferred embodiment of the invention Y is attached at the ortho-position on $Ar_2$. Such ortho photoinitiator monomers can be conveniently prepared from commercially readily available starting materials such as 2-benzoylbenzoic acid.

Benzophenones are well-studied, commercially-available photoinitiator moieties, and their UV absorption can be tailored according to the substitution pattern of the aryl groups. Preferred substituents on $Ar_1$ and $Ar_2$ are electron-donating groups or atoms such as N, O and S. Such substituents provide UV absorption at a longer wavelength, meaning that LED lamps can be used as a UV source. LED lamps provide advantages such as low energy consumption and generate less heat; thus the substrate temperature can be controlled more accurately. Accordingly, in a preferred embodiment of the invention $Ar_1$ and $Ar_2$ may each independently optionally be substituted with one or more electron-donating groups or atoms; more preferably such one or more substituents, e.g. one, two, three or four substituents, may be selected from the group consisting of —$CH_3$, —$CH_2CH_3$, —$CH_2CH_2CH_3$, —$CH(CH_3)_2$, —$C_6H_5$, —$OCH_3$, —$OCH_2CH_3$, —$OCH_2CH_2CH_3$, —$OCH(CH_3)_2$, —$OC_6H_5$, —$SCH_3$, —$SCH_2CH_3$, —$SCH_2CH_2CH_3$, —$SCH(CH_3)_2$, —$SC_6H_5$, —$N(CH_3)_2$, —$N(CH_2CH_3)_2$, and —$N(CH_2CH_2OCH_2CH_2)_2$.

A sub-structure which describes photoinitiator monomers of Formula I has the general formula (IIIa)

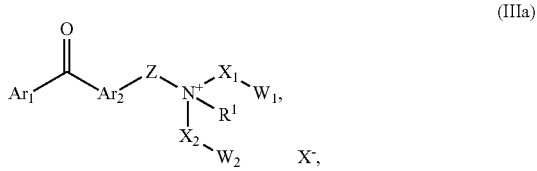

(IIIa)

wherein $Ar_1$ and $Ar_2$ are independently selected from the same or different aryl, where Z may be present at any position on $Ar_2$, and where each aryl independently may be optionally substituted with one or more substituents described herein above in relation to formula (III); and wherein $Ar_1$, $Ar_2$, Z, $R^1$, $X^-$, $X_1$, $X_2$, $W_1$ and $W_2$, and preferred options for these groups are as defined herein. Preferably Z may be present at the para-position on $Ar_2$.

Another sub-structure which describes photoinitiator monomers of General Formula (I), has the general formula (IV):

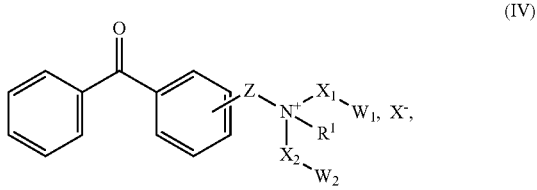

(IV)

wherein Z, $R^1$, $X^-$, $X_1$, $X_2$, $W_1$ and $W_2$, and preferred options for these groups, are as defined herein, and the two aromatic rings of formula (IV) are each independently optionally substituted.

Another sub-structure which describes photoinitiator monomers of Formula (I) has the general formula (V):

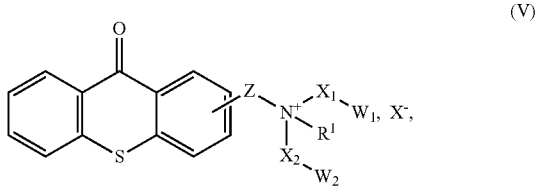

(V)

wherein Z, $R^1$, $X^-$, $X_1$, $X_2$, $W_1$ and $W_2$, and preferred options for these groups, are as defined herein, and the two aromatic rings of formula (V) are each independently optionally substituted.

In formulas (IV) and (V) Z may be attached at any position, i.e. ortho-, metha- or para-position to the carbonyl group (the attachment point is indicated in formulas (IV) and (V) by the unattached bond of Z), and where each aromatic ring independently may be optionally substituted with one or more substituents selected from the groups specified herein above for formula (III). Preferably Z may be present at the para-position to the carbonyl group.

Another sub-structure which describes photoinitiator monomers of Formula (I) has the general formula (IVa):

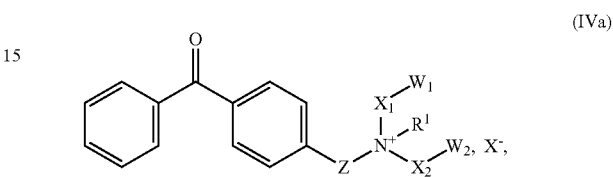

(IVa)

wherein Z, $R^1$, $X^-$, $X_1$, $X_2$, $W_1$ and $W_2$, and preferred options for these groups, are as defined herein, and the two aromatic rings of formula (IVa) are each independently optionally substituted.

Another sub-structure which describes photoinitiator monomers of Formula (I) has the general formula (IVb):

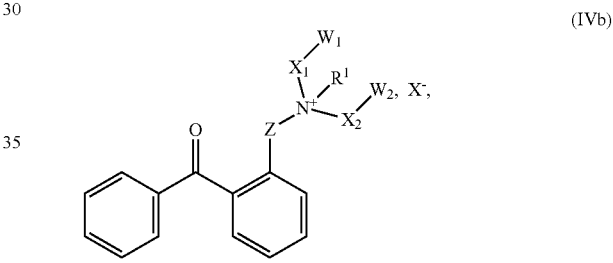

(IVb)

wherein Z, $R^1$, $X^-$, $X_1$, $X_2$, $W_1$ and $W_2$, and preferred options for these groups, are as defined herein, and the two aromatic rings of formula (IVb) are each independently optionally substituted.

Another sub-structure which describes photoinitiator monomers of Formula (I) has the general formula (Va):

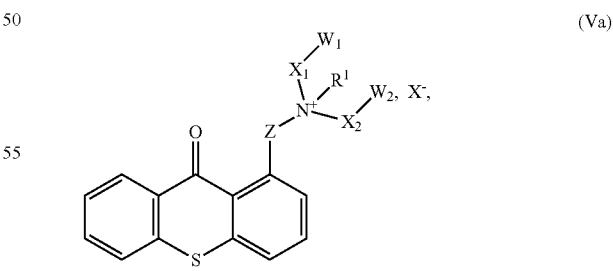

(Va)

wherein Z, $R^1$, $X^-$, $X_1$, $X_2$, $W_1$ and $W_2$, and preferred options for these groups, are as defined herein, and the two aromatic rings of formula (Va) are each independently optionally substituted.

Another sub-structure which describes photoinitiator monomers of Formula (I) has the general formula (IVc):

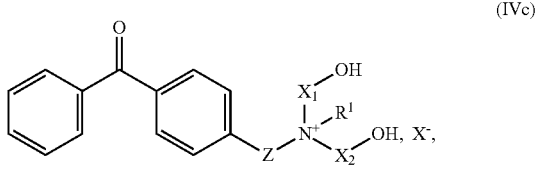

(IVc)

wherein Z, $R^1$, $X^-$, $X_1$, and $X_2$, and preferred options for these groups, are as defined herein, and the two aromatic rings of formula (IVc) are each independently optionally substituted.

Judicious selection of functional groups can be used to obtain absorption maxima in a desired wavelength region (e.g. impart positive mesomeric effect within the photoinitiator). The ketones described in the present invention are inherent electron accepting groups, so careful selection of electron-donating groups as substituents on aromatic rings within the photoinitiator can lead to absorption profiles matching the light source best suited for the desired curing application. Mechanistically, the efficiency of photoinitiators relies on their ability to intersystem cross from an electronic excited (singlet) state to a triplet state. Some literature has described that such intersystem crossing is less efficient when a higher degree of charge transfer is present within the system. Thus, the absorption profile of a photoinitiator can be controlled to some extent but not without altering the efficiency of radical formation. (see N. J. Turro, *Modern Molecular Photochemistry*, University Science Books: Sausalito, 1991).

In one preferred embodiment of the present invention Z comprises the linker -Za-Zb-, as seen in the partial formula (II) herein above. Specifically Za is designed so that it is attached via a heteroatom, —O—, —$NR^2$—, or —S—, to Pi, i.e. to the $Ar_2$ of formula (III). This particular functionality of Za confers greater hydrolytic stability at the same time as increasing the absorption in the 350-400 nm band region. An example of this effect is the comparison of the UV spectrum of chloro-thioxanthone which has an absorption at 385 nm with a $E_1^1$ of 159 whereas, its close relative which has a propoxy substituent on the aromatic ring, 1-chloro-4-propoxy thioxanthone has an absorption at 387 nm and an $E_1^1$ of 175. This enhanced extinction coefficient of absorption allows for faster curing. More preferably Za may be attached via a —O— moiety to Pi, hence in this case Za is —[O—($C_1$-$C_{12}$alkylene)]$_n$-, as such an alkoxy substituent confer greater hydrolytic stability.

A similar effect can be seen in comparing the UV spectra of 4-[(4-methylphenyl)sulfanyl]-benzophenone (Speedcure BMS) with 4-methylbenzophenone (Speedcure MBP). The absorption maximum of Speedcure BMS at 316 nm is extremely important in increasing the speed of cure of Speedcure BMS over Speedcure MBP. This band is non-existent in Speedcure MBP. FIG. 1 shows the UV spectra of BMS (0.001% w/v in methanol, 1 cm path length; bold black line) and MBP (0.001% w/v in methanol, 1 cm path length, thin dotted line)

The herein above described sub-formulas (II), (III), (IIIa), (IV), (IVa), (IVb), (IVc), (V), and (Va) of photoinitiator monomers of General formula (I), applies for the second and third aspect of the invention in addition to the first aspect of the invention.

The herein above described sub-formulas (II), (III), (IIIa), (IV), (IVa), (IVb), (IVc), (V), and (Va) of photoinitiator monomers of General formula (I), applies for the fourth and fifth aspect of the invention as well, mutatis mutandis. By way of example, for the fourth aspect of the invention sub-formula (V) corresponds to sub-formula (V') where $R^1$ is absent and the quaternary ammonium $N^+$ atom is replaced by a tertiary amine group.

Definitions

It will be apparent to one skilled in the art that the photoinitiator monomers and polymeric photoinitiators of the invention, containing a quaternary ammonium moiety, will be present in their ammonium salt forms. When the photoinitiator monomers of formula (I), and subformulas thereof, are mentioned herein it is implied that they are present in their ammonium salt form. Such salt forms are included within the scope of the invention.

$X^-$, as used herein, denotes the counterion of the ammonium salt, hence $X^-$ is a counterion, or a negatively charged moiety, such as e.g. —$SO_3^-$, —$COO^-$, —$OSO_3^-$ or —O—P(=O)(O-alkyl)$O^-$, that is covalently bound to any carbon atom of Pi, Z, Za, Zb, $R^1$, $X_1$, $X_2$ or their optionally substituents to form a betaine-type structure. Non-limiting examples of such anionic counterions include fluoride, chloride, bromide, iodide, sulfate, carbonate, phosphate, tetrafluoroborate, tetraarylborate (e.g. tetraphenylborate), hexafluorophosphate, alkyl carboxylate (e.g. acetate), aryl carboxylate (e.g. benzoate), alkyl sulfonate (e.g. mesylate) and aryl sulfonate (e.g. tosylate). Preferably $X^-$ may be selected from chloride, bromide, iodide, sulfate, tetrafluoroborate, hexafluorophosphate, acetate, benzoate, mesylate, triflate and tosylate, and more preferably $X^-$ may be selected from chloride, bromide and iodide.

The term "form a betaine-type structure", as used herein, denotes that photoinitiator monomers of formula (I) may themselves form a structure where a negatively charged counterion $X^-$ is covalently bound to any carbon atom of Pi, Z, Za, Zb, $R^1$, $X_1$, $X_2$ or their optionally substituents, and balances the positive charge of the quaternary ammonium moiety. Non-limiting examples of such negatively-charged moieties include —$SO_3^-$, —$COO^-$, —$OSO_3^-$ and —O—P(=O)(O-alkyl)$O^-$.

The photoinitiator monomers or polymeric photoinitiators of the invention may exist as solvates. When a photoinitiator monomer can exist in a solvate form, including hydrated forms, such forms are included within the scope of the invention.

The term "alkyl", as used herein, unless otherwise indicated, includes saturated monovalent hydrocarbon radicals having straight or branched moieties. Examples of alkyl moieties include, but are not limited to, methyl, ethyl, propyl, isopropyl, n-butyl, iso-butyl, sec-butyl, tert-butyl and neopentyl. Alkyl may preferably be $C_1$-$C_6$ alkyl, i.e. groups containing from 1 to 6 carbon atoms, and for some embodiments of the present invention more preferably $C_1$-$C_4$ alkyl.

The term "alkylene" as used herein specify moieties derived from alkanes in which two H atoms have been removed to form a diradical species. The simplest alkylene is methylene —$CH_2$—, and other alkylenes include ethylene —$CH_2$—$CH_2$—, propylene —$C_3H_6$— and butylene —$C_4H_8$—. The term "alkylene" includes branched and linear alkylenes, with linear alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "cycloalkyl" as used herein, unless otherwise indicated, includes non-aromatic saturated cyclic alkylene moieties, where alkylene is as defined above, or cyclic alkyl moieties, where alkyl is as defined above. The first applies where the cycloalkyl is used in a linker moiety being attached at two points to the remaining part of the photoinitiator monomers of formula (I). The skilled person will be able to identify in each case what applies. Examples of cycloalkyl include, but are not limited to, cyclopropyl, cyclobutyl, cyclopentyl, cyclohexyl, cycloheptyl, cyclooctyl. Cycloalkyl is preferably $C_3$-$C_8$ cycloalkyl, i.e. cycloalkyl groups containing from 3 to 8 carbon atoms, and more preferably $C_3$-$C_6$ cycloalkyl.

The term "alkenylene" as used herein specify moieties derived from alkenes in which two H atoms have been removed to form a diradical species. Examples include ethenylene —CH=CH— and propenylene —$C_3H_4$— moieties. The term "alkenylene" includes branched, linear and cyclic alkenylene, with linear alkenylene being most preferred. Preferred alkenylenes contain between 2 and 6 carbon atoms (i.e. $C_2$-$C_6$ alkenylenes).

The term "aryl" as used herein define an unsaturated cyclic system which contains a delocalised π-electron system about the ring. Aryl groups may comprise from 4-12 atoms, suitably from 6-8 atoms, most suitably 6 atoms. "Aryl" may preferably comprise carbocyclic rings, and may preferably be phenyl (—$C_6H_5$).

The term "aryl" is also used to include aromatic heterocycles—rings in which one or more atoms in the ring (e.g. 1-3 atoms) are N, S, P or O. Aromatic heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings). The term "aryl" also includes fused ring systems.

When referring to a linker moiety (e.g. Z, Za, Zb, $X_1$, $X_2$, Q, T), the term "aryl" is used to define moieties derived from arenes in which two H atoms have been removed to form a diradical species (i.e. arylene). Examples include 1,2-phenylene, 1,3-phenylene and 1,4-phenylene.

The term "heterocyclyl" as used herein means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom, respectively, is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "acrylate monomer" is used to describe substances containing the functional group C=C—C(=O)—O—, which are able to polymerize via the alkene C=C moiety. The carbon atoms of the alkene may be substituted.

The term "leaving group", abbreviated "LG", is used to describe a reactive moiety bound to a carbon atom that can be displaced by another moiety in a substitution reaction thus forming a new carbon-carbon or carbon-heteroatom bond. Typically a leaving group LG is —F, —Cl, —Br, —I, —OSO$_2$CH$_3$, —OSO$_2$-(p-$C_6H_4$)—CH$_3$, —OSO$_2$CF$_3$. Examples of leaving group also include reactive moieties that are a part a cyclic alkylating reagent. In a substitution reaction, the cyclic structure of the alkylating agent opens thus forming a new carbon-carbon or carbon-heteroatom bond and revealing a negatively charged moiety. Examples of such cyclic alkylating reagents include 1,3-propanesultone and 1,4-butanesultone.

The term "macromonomers" is used herein to describe a polymer or oligomer, that has two reactive groups, often at the ends, which enables it to act as a monomer in further polymerisation reactions becoming attached to the main backbone of the final polymer. Macromonomers may also be referred to as "pre-polymers". Non-limiting examples of suitable macromonomers or pre-polymers are polyalkylethers, polyesters, polydisulfides, polyamines, or polycarbonates having two free reactive groups, such as —OH groups, —NH$_2$ groups, —COOH groups, or —SH groups. Suitable macromers or pre-polymers to be used in polymeric photoinitiators of the present invention are described further in relation to monomer C. When photoinitiator monomers of formula (I), comprise only two end groups $W_1$ and $W_2$ capable of taking part in a particular polymerisation reaction, the monomer of formula (I) will be incorporated in the polymer backbone with the photoinitiator as a pendant group via the linkers Z or ZaZb, branching of the polymer is additionally avoided. It is therefore to be avoided that other functional groups being capable of participating in the desired polymer reaction are present in the photoinitiator monomers of the present invention. This therefore also applies to any optional substituents being present on photoinitiator monomers of formula (I). Accordingly, in the following, when a part of a molecule, or a moiety, is described as "optionally substituted" or "is optionally substituted with one or more substituents" it refers to the optional possibility that one or more hydrogen atoms of a moiety, such as e.g. alkyl, alkylene, alkenyl, alkenylene, cycloalkyl, aryl, and heterocyclyl moieties (all referring to $C_1$-$C_{12}$ alkyl, $C_1$-$C_6$ alkyl, $C_3$-$C_8$ cycloalkyl etc. as appropriate in the context), may or may not be substituted by one or more substituents. For example 1 to 4 substituents, preferably 1 to 3 substituents, more preferably 1 or 2 substituents. Such one or more optional substituents, unless otherwise specifically stated, may be selected from the group consisting of —F, —Cl, —Br, —I, —CN, —NO$_2$, —C$_1$-C$_6$ alkyl, —C$_2$-C$_6$ alkenyl, —C$_3$-C$_6$ cycloalkyl, aryl, heterocyclyl, —O—(C$_1$-C$_6$ alkyl), —O—C$_3$-C$_8$ cycloalkyl, —O-aryl, —C(O)—(R$^8$), —C(O)-aryl, —C(O)O—(C$_1$-C$_6$ alkyl), —C(O)O-aryl, —O—C(O)-aryl, —O—C(O)—O—(C$_1$-C$_6$ alkyl), —O—C(O)—O-aryl, —N(C$_1$-C$_6$alkyl)$_2$, —N(C$_1$-C$_6$alkyl)(C$_3$-C$_6$ cycloalkyl), —N(C$_1$-C$_6$alkyl)(aryl), —N(aryl)$_2$, —N(R$^8$)—C(O)—(C$_1$-C$_6$ alkyl), —N(R$^8$)—C(O)-aryl, —C(O)—N(R$^8$)$_2$, —C(O)—N(R$^8$)-aryl, —C(O)—N(aryl)$_2$, —O—C(O)—N(R$^8$)$_2$, —O—C(O)—NH—(C$_1$-C$_6$aryl), —N(R$^8$)—C(O)—O—(C$_1$-C$_6$alkyl), —NH—C(O)—O—(C$_1$-C$_6$aryl), —S(O)—(C$_1$-C$_6$ alkyl), —S(O)-aryl, —SO$_2$—(C$_1$-C$_6$ alkyl), —SO$_2$-aryl, —S—(C$_1$-C$_6$ alkyl) and —S-aryl; wherein R$^8$ is H or C$_1$-C$_6$ alkyl.

In a preferred embodiment of the invention, the one or more optional substituents are selected from the group consisting of —F, —Cl, —Br, —I, —CN, —NO$_2$, —C$_1$-C$_6$ alkyl, aryl, —O—(C$_1$-C$_6$ alkyl), —C(O)—O—(C$_1$-C$_6$ alkyl), —S—(C$_1$-C$_6$ alkyl), —S(O)—(C$_1$-C$_6$ alkyl), —SO$_2$—(C$_1$-C$_6$ alkyl), —NH—C(O)—(C$_1$-C$_6$ alkyl), —C(O)—NH—(C$_1$-C$_6$ alkyl), and —C(O)—NH$_2$.

Photoinitiator monomers of general formula (I) may contain chiral centers and therefore may exist in different enantiomeric or diasteromeric forms. This invention relates to all optical isomers and all stereoisomers of general formula (I), both as racemic mixtures and as individual enantiomers and diastereomers ((+)- and (−)-optically active forms) of such photoinitiator monomers and mixtures thereof. Individual isomers, if desired, can be obtained by known methods, such as optical resolution, optically selective reactions or chromatographic separation in the preparation steps or for the final products.

The photoinitiator monomers of general formula (I) may contain a protecting group. The protective group is a group that protects the functional groups of the photoinitiator monomers prior to use in polymerization reactions, such protecting group may be covalently bound independently to $W_1$ and $W_2$ through a labile bond that can be broken before or during polymerisation. Photoinitiator monomers of formula (I) incorporating such protecting groups, are within the scope of the invention. The term "protecting group" or "protective group" as used herein, refers to e.g. silyl protecting group for —OH, —CH$_2$OH, —NH$_2$ or —NHR$^6$, which is selected from typical —Si(CH$_3$)$_3$, —Si(CH$_2$CH$_3$)$_3$, —Si(CH(CH$_3$)$_2$)$_3$, —Si(C$_6$H$_5$)$_3$ and —Si(CH$_3$)$_2$(C(CH$_3$)$_3$) groups. The term "protecting group" as used herein, also refers to e.g. thermally labile protecting group for —NCO or —NCS of W$_3$ or W$_4$ of monomer (B), which is selected from typical diethyl malonate (—CH(COOCH$_2$CH$_3$)$_2$ or 3,5-dimethylpyrazole (—N(—C(CH$_3$)═CH—C(CH$_3$)═N—)) as described in e.g. Protective Groups in Organic Synthesis edited by T. W. Greene et al. (John Wiley & Sons, 1991).

Linkers, Z and -Za-Zb-

The portion of the photoinitiator monomer of Formula (I) indicated by Z represent a linker moiety. The linker Z has two ends: at one end it is joined to the photoinitiator moiety, at the other end, it is joined to the "quaternary ammonium branching group" hereby linking Pi and this group together. Simultaneously it serves to hold the photoinitiator moiety at a certain distance from the polymer backbone, when the photoinitiator monomer is incorporated into a polymeric photoinitiator. The quaternary ammonium becomes part of the polymeric backbone when a photoinitiator monomer according to the invention is incorporated into a polymeric photoinitiator according to the invention. In formula (II) being a subformula of formula (I), Z is a linker moiety -ZaZb-. Za is joined at one end to Pi and at the other end to Zb; when Zb is a single bond, Za is joined by said single bond directly to the quaternary ammonium.

The size of the linker Z is selected according to the desired properties of the photoinitiator. A short linker will provide close interaction between the polymer backbone and the photoinitiator moiety. On the other hand, a long linker will provide freer movement of the photoinitiator moiety in the polymerization process, which also provides advantages. A rigid structure may lower the possibility that radicals formed at one site propagate to polymer chains in the vicinity of the photoinitiator, whereas a "loose" structure could facilitate dispersion of radical functionalities over a wider area. Suitably, the linker has a molecular weight of less than 10000 Da, suitably less than 5000 Da, most suitably less than 1000 Da. The linker Z or -Za-Zb- preferably comprises no more than 50 atoms, preferably no more than 30 atoms.

General Formula (I) and formula (II), the latter being a subformula of (I):

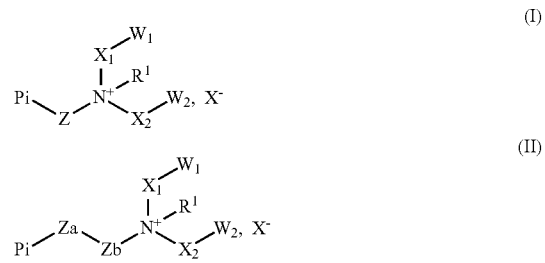

Pi, R$^1$, X$_1$, X$_2$, W$_1$, W$_2$, Z, Za, Zb, and X$^-$ will be further described herein below.

In formula (I) of the present invention, Z is a linker moiety.

Z may preferably be selected from the group consisting of a single bond, optionally substituted C$_1$-C$_{12}$ alkylene, optionally substituted C$_2$-C$_{12}$ alkenylene, —O—, —S—, —NR$^2$—, —C(═O)—, —C(═O)—NR$^7$—, —NR$^7$—C(═O)—, —C(═NR$^7$)—, —SO$_2$—, —P(═O)(OR$^7$)—, optionally substituted —C$_3$-C$_8$ cycloalkyl, optionally substituted heterocyclyl, optionally substituted aryl, —[O—(C$_1$-C$_{12}$ alkylene)]$_n$-, —[NR$^2$—(C$_1$-C$_{12}$ alkylene)]$_n$-, —[S—(C$_1$-C$_{12}$ alkylene)]$_n$-, and combinations thereof, wherein R$^2$ is optionally substituted C$_1$-C$_{12}$ alkyl, R$^7$ is H or optionally substituted C$_1$-C$_{12}$ alkyl, and n is an integer from 1-20.

Z may be selected from a single bond, optionally substituted C$_1$-C$_{12}$ alkylene, optionally substituted C$_2$-C$_{12}$ alkenylene, —O—, —S—, —NR$^2$—, —C(═O)—, —C(═O)—NR$^7$—, —NR$^7$—C(═O)—, —C(═NR$^7$)—, optionally substituted —C$_3$-C$_8$ cycloalkyl, optionally substituted heterocyclyl, optionally substituted aryl, —[O—(C$_1$-C$_{12}$ alkylene)]$_n$-, —[NR$^2$—(C$_1$-C$_{12}$ alkylene)]$_n$-, —[S—(C$_1$-C$_{12}$ alkylene)]$_n$-, and combinations thereof, wherein R$^2$ is optionally substituted C$_1$-C$_{12}$ alkyl, R$^7$ is H or optionally substituted C$_1$-C$_{12}$ alkyl, and n is an integer from 1-20.

Preferably n may be an integer from 1-10, more preferably from 1-5, such as e.g. 1, 2, 3, 4 or 5, and even more preferably from 1-2.

In that Z may comprise a combination of the above-mentioned groups, the invention encompasses photoinitiator monomers (A) in which Z is made up of two or more of the above-mentioned groups in series, e.g.

—O—(C$_1$-C$_{12}$ alkylene)-
—(C$_1$-C$_{12}$ alkylene)-O—(C$_1$-C$_{12}$ alkylene)-
—O—(C$_1$-C$_{12}$ alkylene)-O—(C$_1$-C$_{12}$ alkylene)-
—O—(C$_1$-C$_{12}$ alkylene)-O-(aryl)-
—NR$^2$—(C$_1$-C$_{12}$ alkylene)-
—(C$_1$-C$_{12}$ alkylene)-NR$^2$—(C$_1$-C$_{12}$ alkylene)-
—NR$^2$—(C$_1$-C$_{12}$ alkylene)-NR$^2$—(C$_1$-C$_{12}$ alkylene)-
—NR$^2$—(C$_1$-C$_{12}$ alkylene)-O—(C$_1$-C$_{12}$ alkylene)-
—O—(C$_1$-C$_{12}$ alkylene)-NR$^2$—(C$_1$-C$_{12}$ alkylene)-
—C(═O)—O—(C$_1$-C$_{12}$ alkylene)-
—C(═O)—NR$^7$—(C$_1$-C$_{12}$ alkylene)-
—O—C(═O)—(C$_1$-C$_{12}$ alkylene)-
—N—C(═O)—(C$_1$-C$_{12}$ alkylene)-
—O-aryl-
—(C$_1$-C$_{12}$ alkylene)-C(═O)—NR$^7$—C(═O)—(C$_1$-C$_{12}$ alkylene)-.

In all of the above, the —(C$_1$-C$_{12}$ alkylene)-, —(C$_2$-C$_{12}$ alkenylene)-, -cycloalkyl, -heterocyclyl-, and -aryl- groups may be substituted or unsubstituted. Other chemically feasible combinations of moieties for Z can be determined by the person skilled in the art.

R² may be optionally substituted $C_1$-$C_6$ alkyl, such as e.g. methyl, ethyl, propyl, isopropyl, butyl, isobutyl, pentyl, or isopentyl. R⁷ may be H. R⁷ may alternatively be optionally substituted $C_1$-$C_6$ alkyl, such as e.g. methyl, ethyl, propyl, butyl, pentyl or hexyl. In a preferred embodiment of formula (I) R⁷ is $C_1$-$C_4$ alkyl.

Suitably, Z is selected from a single bond, optionally substituted $C_1$-$C_{12}$ alkylene, optionally substituted $C_2$-$C_{12}$ alkenylene, —O—, —S—, —NR²—, —[O—($C_1$-$C_{12}$ alkylene)]$_n$-, and combinations thereof, wherein R² is optionally substituted $C_1$-$C_{12}$ alkyl and n is an integer from 1-20. Z may specifically be selected from optionally substituted $C_1$-$C_{12}$ alkylene, optionally substituted $C_1$-$C_{12}$ alkenylene, —O—, —S—, —NR²—, and —[O—($C_1$-$C_{12}$ alkylene)]$_n$-, wherein R² is optionally substituted $C_1$-$C_{12}$ alkyl and n is an integer from 1-20. Z may also be selected from optionally substituted $C_1$-$C_{12}$ alkylene, preferably optionally substituted $C_1$-$C_6$ alkylene.

Alternatively Z may be selected from a single bond, optionally substituted $C_1$-$C_6$ alkylene, optionally substituted $C_2$-$C_6$ alkenylene, —O—, —S—, —NR²—, —C(=O)—, —C(=O)—NR⁷—, —NR⁷—C(=O)—, —C(=NR⁷)—, optionally substituted —$C_3$-$C_6$ cycloalkyl, optionally substituted heterocyclyl, optionally substituted aryl, —[O—($C_1$-$C_6$ alkylene)]$_n$-, —[NR²—($C_1$-$C_6$ alkylene)]$_n$-, —[S—($C_1$-$C_6$ alkylene)]$_n$-, and combinations thereof; preferably from optionally substituted $C_1$-$C_6$ alkylene, —NR²—, —C(=O)—, —[O—($C_1$-$C_6$ alkylene)]$_n$-, —[NR²—($C_1$-$C_6$ alkylene)]$_n$-; wherein R² is optionally substituted $C_1$-$C_6$ alkyl, R⁷ is H or optionally substituted $C_1$-$C_6$ alkyl, and n is an integer from 1-6, preferably 1-2.

In a specific embodiment of the invention, Z is a single bond.

Specifically, Z may be selected from $C_1$-$C_6$ alkylene, $C_2$-$C_6$ alkenylene, —NR²—, —C(=O)—($C_1$-$C_6$ alkylene)-, —C(=O)—O—($C_1$-$C_6$ alkylene)-, —C(=O)—NR⁷—($C_1$-$C_6$ alkylene), —$C_3$-$C_6$ cycloalkyl, aryl, heterocyclyl, —[O—($C_1$-$C_6$ alkylene)]$_n$-, —[($C_1$-$C_6$ alkylene)-O—($C_1$-$C_6$ alkylene)]$_n$-, —[NR²—($C_1$-$C_6$ alkylene)]$_n$, and —[S—($C_1$-$C_6$ alkylene)]$_n$—, wherein R² is optionally substituted $C_1$-$C_6$ alkyl, R⁷ is H or optionally substituted $C_1$-$C_6$ alkyl, n is an integer from 1-2, and wherein any $C_1$-$C_6$ alkylene, $C_2$-$C_6$ alkenylene, —$C_3$-$C_6$ cycloalkyl, aryl or heterocyclyl each independently is optionally substituted with one or more substituents.

More specifically Z may be selected from $C_1$-$C_6$ alkylene, $C_2$-$C_6$ alkenylene, —NR²—, —C(=O)—($C_1$-$C_6$ alkylene)-, —C(=O)—NR⁷—, —C(=O)—O—($C_1$-$C_6$ alkylene)-, —C(=O)—NR⁷—($C_1$-$C_6$ alkylene), —[O—($C_1$-$C_6$ alkylene)]$_n$-, —[($C_1$-$C_6$ alkylene)-O—($C_1$-$C_6$ alkylene)]$_n$—, —[NR²—($C_1$-$C_6$ alkylene)]$_n$, and —[S—($C_1$-$C_6$ alkylene)]$_n$-, wherein R² is optionally substituted $C_1$-$C_6$ alkyl, R⁷ is H or optionally substituted $C_1$-$C_6$ alkyl, n is an integer from 1-2, and wherein any $C_1$-$C_6$ alkylene, $C_2$-$C_6$ alkenylene, aryl or heterocyclyl each independently is optionally substituted with one or more substituents.

Photoinitiator monomers and photoinitiator monomers (A) of Formula (I) having formula (I) in which Z comprises an electron-donating group adjacent Pi are advantageous, as this provides opportunities to tailor the UV absorption of the photoinitiator moiety. Accordingly, Z may also be selected from optionally substituted —O—($C_1$-$C_{12}$ alkylene)-, preferably optionally substituted —O—($C_1$-$C_6$ alkylene)-, optionally substituted —S—($C_1$-$C_{12}$ alkylene)-, preferably optionally substituted —S—($C_1$-$C_6$ alkylene)-, and optionally substituted —NR²—($C_1$-$C_{12}$ alkylene)-, preferably optionally substituted —NR²—($C_1$-$C_6$ alkylene)-; wherein R² is optionally substituted $C_1$-$C_{12}$ alkyl, preferably $C_1$-$C_6$ alkyl. Z may even be selected from optionally substituted —O—($C_1$-$C_{12}$ alkylene)-, preferably optionally substituted —O—($C_1$-$C_6$ alkylene)-.

Most preferably, Z may be selected from optionally substituted $C_1$-$C_6$ alkylene and optionally substituted —O—($C_1$-$C_6$ alkylene)-.

A further advantage of the embodiments of the invention where Z are selected from optionally substituted —O—($C_1$-$C_{12}$ alkylene)-, optionally substituted —S—($C_1$-$C_{12}$ alkylene)-, and optionally substituted —NR²—($C_1$-$C_{12}$ alkylene)-, is these linkers being more hydrolytically stable during polymerisation reactions and/or heat treatment of final products.

The optional substituents on linker Z are selected from the group specified herein under the definition of "optionally substituted". In a preferred embodiment of the invention, the optional substituents on linker Z are selected from the groups consisting of —F, —Cl, —Br, —I, —CN, —NO₂, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —SO₂—($C_1$-$C_6$ alkyl), —NH—C(O)—($C_1$-$C_6$ alkyl), —C(O)—NH—($C_1$-$C_6$ alkyl), and —C(O)—NH₂.

Photoinitiator monomers of Formula (I) having formulas (II) in which the linker -Za-Zb-comprises an electron-donating group adjacent Pi are advantageous, as this provides opportunities to tailor the UV absorption of the photoinitiator moiety.

Accordingly, one embodiment of the invention relates to Z being a linker moiety -ZaZb-, and formula (I) is having formula (II):

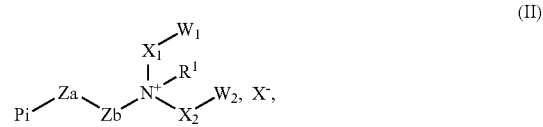

(II)

wherein:

Pi is a photoinitiator moiety;

Za and Zb together form a single bond, or a linker in which Za is selected from optionally substituted —[O—($C_1$-$C_{12}$ alkylene)]$_n$-, optionally substituted —[NR²—($C_1$-$C_{12}$ alkylene)]$_n$, and optionally substituted —[S—($C_1$-$C_{12}$ alkylene)]$_n$-, wherein Za is joined to Pi via the O, N or S atom in Za, and Zb is a linker moiety;

R¹ is selected from optionally substituted $C_1$-$C_{30}$ alkyl, optionally substituted $C_3$-$C_{30}$ alkenyl, optionally substituted $C_3$-$C_{30}$ alkynyl, optionally substituted $C_3$-$C_{12}$ cycloalkyl, optionally substituted —[($C_1$-$C_6$ alkylene)-O—($C_1$-$C_6$ alkylene)]$_p$—H moiety, optionally substituted heterocyclyl, and optionally substituted aryl;

R² is optionally substituted $C_1$-$C_{12}$ alkyl;

n is an integer from 1-20;

p is an integer from 1-6;

X₁ and X₂ are each independently selected from optionally substituted $C_1$-$C_{12}$ alkylene, optionally substituted $C_2$-$C_{12}$ alkenylene, —O—, —S—, —NR⁴—, —C(=O)—, —C(=NR³)—, —Si(R³)₂—O—, optionally substituted $C_3$-$C_8$ cycloalkyl, optionally substituted heterocyclyl, optionally substituted aryl, and combinations thereof;

X₁ and X₂ or a part thereof may be linked to one another or to linkers Za or Zb, or R¹ to form one or more ring structures;

Za, Zb, $R^1$, $X_1$ and $X_2$ are selected such that N is a quaternary ammonium;

$R^3$ is H or optionally substituted $C_1$-$C_{12}$ alkyl;

$R^4$ is optionally substituted $C_1$-$C_{12}$ alkyl;

$X^-$ is a counterion, or a negatively charged moiety that is covalently bound to any carbon atom of Pi, Za, Zb, $R^1$, $X_1$, $X_2$ or their optional substituents to form a betaine-type structure;

$W_1$ and $W_2$ are each independently selected from —OH (forming a primary alcohol), —$CH_2OH$ (forming a secondary alcohol), —$NH_2$, —$NHR^6$, —SH, —$Si(OR^6)_2$—H, —$SiH(R^6)_2$, —$C(=O)$—$OSi(R^6)_3$, —NCO, —NCS, —COOH, —$COOR^6$, —COO-aryl, —$C(=O)$—Cl, —O—$C(=O)$—Cl, —$C(O)$—$NH_2$, —$C(O)$—$NHR^5$, —NH—$C(O)$—$OR^5$, and —$OC(O)$—$NHR^5$;

$R^5$ is H or $C_1$-$C_6$ alkyl; and $R^6$ is $C_1$-$C_6$ alkyl.

In one embodiment of the invention Zb is selected from a single bond, optionally substituted $C_1$-$C_{12}$ alkylene, optionally substituted $C_2$-$C_{12}$ alkenylene, —O—, —S—, —$NR^2$—, —$C(=O)$—, —$C(=O)$—$NR^7$—, —$NR^7$—C(=O)—, —$C(=NR^7)$—, —$SO_2$—, —$P(=O)(OR^7)$—, optionally substituted $C_3$-$C_8$ cycloalkyl, optionally substituted heterocyclyl, optionally substituted aryl, optionally substituted —[O—($C_1$-$C_{12}$ alkylene)]$_n$-, optionally substituted —[$NR^2$—($C_1$-$C_{12}$ alkylene)]$_n$-, optionally substituted —[S—($C_1$-$C_{12}$ alkylene)]$_n$-, and combinations thereof, wherein $R^2$ is optionally substituted $C_1$-$C_{12}$ alkyl, $R^7$ is H or optionally substituted $C_1$-$C_{12}$ alkyl, and n is an integer from 1-20. More preferably, Zb may be a single bond.

In relation to Za and Zb n may preferably be an integer from 1-10, more preferably from 1-6, such as, e.g., 1, 2, 3, 4, 5 or 6, and even more preferably from 1-2.

$R^2$ may be optionally substituted $C_1$-$C_6$ alkyl, such as e.g. methyl, ethyl, propyl, isopropyl, butyl, isobutyl, pentyl, or isopentyl. $R^7$ may be H. $R^7$ may alternatively be optionally substituted $C_1$-$C_6$ alkyl, such as e.g. methyl, ethyl, propyl, butyl, pentyl or hexyl. In a preferred embodiment $R^2$ or $R^7$ is each independently $C_1$-$C_4$ alkyl.

When Z is linker -Za-Zb-, i.e. Formula (II), then Za, Zb, $R^1$, $X_1$ and $X_2$ are selected such that N is a quaternary ammonium, i.e. Zb is for example selected such that N is not incorporated in an amide moiety.

The invention encompasses photoinitiator monomers in which the linker -Za-Zb- is made up of two or more of the above-mentioned groups in series, e.g.

—O—($C_1$-$C_{12}$ alkylene)-
—O—($C_1$-$C_{12}$ alkylene)-O—($C_1$-$C_{12}$ alkylene)-
—O—($C_1$-$C_{12}$ alkylene)-O-(aryl)-
—$NR^2$—($C_1$-$C_{12}$ alkylene)-
—$NR^2$—($C_1$-$C_{12}$ alkylene)-$NR^2$—($C_1$-$C_{12}$ alkylene)-
—$NR^2$—($C_1$-$C_{12}$ alkylene)-O—($C_1$-$C_{12}$ alkylene)-
—O—($C_1$-$C_{12}$ alkylene)-$NR^2$—($C_1$-$C_{12}$ alkylene)-.

In all of the above, the —($C_1$-$C_{12}$ alkylene)-, —($C_2$-$C_{12}$ alkenylene)-, $C_3$-$C_8$ cycloalkyl, -heterocyclyl-, and -aryl- groups may be substituted or unsubstituted. Other chemically feasible combinations of moieties for ZaZb can be determined by the person skilled in the art.

In one preferred embodiment of the invention Zb is selected from a single bond, optionally substituted $C_1$-$C_{12}$ alkylene, optionally substituted $C_2$-$C_{12}$ alkenylene, —O—, —S—, —$NR^2$—, —[O—($C_1$-$C_{12}$ alkylene)]$_n$-, and combinations thereof, wherein $R^2$ is optionally substituted $C_1$-$C_{12}$ alkyl and n is an integer from 1-20. Specifically Zb may be selected from a single bond, optionally substituted $C_1$-$C_{12}$ alkylene, optionally substituted $C_2$-$C_{12}$ alkenylene, —O—, —S—, —$NR^2$—, and —[O—($C_1$-$C_{12}$ alkylene)]$_n$-, wherein $R^2$ is optionally substituted $C_1$-$C_{12}$ alkyl, and n is an integer from 1-20. Zb may also be selected from optionally substituted $C_1$-$C_{12}$ alkylene, preferably optionally substituted $C_1$-$C_6$ alkylene. Most preferably, Zb may be selected from a single bond, optionally substituted $C_1$-$C_6$ alkylene, and optionally substituted —O—($C_1$-$C_6$ alkylene)-.

Photoinitiator monomers of Formula (I) in which the linker -Za-Zb- comprises an electron-donating group adjacent Pi are advantageous, as this provides opportunities to tailor the UV absorption of the photoinitiator moiety. Accordingly, in one preferred embodiment of the present invention Za is selected from optionally substituted —[O—($C_1$-$C_{12}$ alkylene)]$_n$-, optionally substituted —[$NR^2$—($C_1$-$C_{12}$ alkylene)]$_n$, and optionally substituted —[S—($C_1$-$C_{12}$ alkylene)]$_n$-; wherein $R^2$ is optionally substituted $C_1$-$C_{12}$ alkyl, and n is an integer from 1-6, preferably 1-2; wherein Za is joined to Pi via the O, N or S atom in Za. In a more preferred embodiment Za is selected from optionally substituted —O—($C_1$-$C_{12}$ alkylene)-, preferably optionally substituted —O—($C_1$-$C_6$ alkylene)-.

In another preferred embodiment Za is selected from optionally substituted —[O—($C_1$-$C_6$ alkylene)]$_n$-, optionally substituted —[$NR^2$—($C_1$-$C_6$ alkylene)]$_n$, and optionally substituted —[S—($C_1$-$C_6$ alkylene)]$_n$-, wherein Za is joined to Pi via the O, N or S atom in Za; and Zb is selected from a linker moiety; preferably Zb is selected from a single bond, optionally substituted $C_1$-$C_6$ alkylene, optionally substituted $C_2$-$C_6$ alkenylene, —O—, —S—, —$NR^2$—, and combinations thereof; more preferably Zb is selected from a single bond, optionally substituted $C_1$-$C_6$ alkylene, optionally substituted $C_2$-$C_6$ alkenylene, —O—, —S—, —$NR^2$—, and —[O—($C_1$-$C_6$ alkylene)]$_n$-; wherein $R^2$ is optionally substituted $C_1$-$C_6$ alkyl, n is an integer from 1-6, preferably 1-2.

In a specific embodiment of the invention, -Za- is selected from -[O—($C_1$-$C_6$ alkylene)]$_n$-, —[$NR^2$—($C_1$-$C_6$ alkylene)]$_n$, —[S—($C_1$-$C_6$ alkylene)]$_n$-, —O—($C_1$-$C_6$ alkylene)-$NR^2$—($C_1$-$C_6$ alkylene)-, —$NR^2$—($C_1$-$C_6$ alkylene)-O—($C_1$-$C_6$ alkylene)-, —S—($C_1$-$C_6$ alkylene)-O—($C_1$-$C_6$ alkylene)-, —O—($C_1$-$C_6$ alkylene)-S—($C_1$-$C_6$ alkylene)-, —S—($C_1$-$C_6$ alkylene)-$NR^2$—($C_1$-$C_6$ alkylene)-, and —$NR^2$—($C_1$-$C_6$ alkylene)-S—($C_1$-$C_6$ alkylene)-, wherein $C_1$-$C_6$ alkylene optionally is substituted with one or more substituents, wherein $R^2$ is $C_1$-$C_6$ alkyl, and n is an integer from 1-2.

In a specific embodiment of the invention -Zb- is selected from a single bond, —$C(=O)$—O—$C_1$-$C_6$ alkylene-, —O—$C(=O)$—$C_1$-$C_6$ alkylene-, —$C(=O)$—$C_1$-$C_6$ alkylene-, —$C(=O)$—$NR^7$—$C_1$-$C_6$ alkylene-, —$NR^7$—C(=O)—($C_1$-$C_6$ alkylene)-, —$SO_2$—$C_1$-$C_6$ alkylene-, —$P(=O)(OR^7)$—($C_1$-$C_6$ alkylene)-, —$C(=O)$—O—$C_2$-$C_6$ alkenylene-, —O—$C(=O)$—$C_2$-$C_6$ alkenylene-, —$C(=O)$—$C_2$-$C_6$ alkenylene-, —$C(=O)$—$NR^7$—$C_2$-$C_6$ alkenylene-, —$NR^7$—$C(=O)$—$C_2$-$C_6$ alkenylene-, —$C(=O)$—$NR^7$—$C_2$-$C_6$ alkenylene-, —$SO_2$—$C_2$-$C_6$ alkenylene-, —$P(=O)(OR^7)$—$C_2$-$C_6$ alkenylene-, —$C_3$-$C_6$ cycloalkyl, heterocyclyl, aryl, and -aryl-($C_1$-$C_6$ alkyl)-, wherein any $C_1$-$C_6$ alkylene, $C_2$-$C_6$ alkenylene, —$C_3$-$C_6$ cycloalkyl, heterocyclyl or aryl each independently optionally is substituted with one or more substituents, wherein $R^7$ is H or $C_1$-$C_6$ alkyl, and n is an integer from 1-6, preferably 1-2.

In a more specific embodiment of the invention -Zb- is selected from a single bond, —$C(=O)$—O—$C_1$-$C_6$ alkylene-, —O—$C(=O)$—$C_1$-$C_6$ alkylene-, —$C(=O)$—$C_1$-$C_6$ alkylene-, —$C(=O)$—$NR^7$—$C_1$-$C_6$ alkylene-, —$NR^7$—C(=O)—($C_1$-$C_6$ alkylene)-, —$SO_2$—$C_1$-$C_6$ alkylene-, —P(=O)(OR$^7$)—(C$_1$-C$_6$ alkylene)-, —C$_3$-C$_6$ cycloalkyl, heterocyclyl, aryl and -aryl-(C$_1$-C$_6$ alkyl)-, wherein any C$_1$-C$_6$ alkylene, —C$_3$-C$_6$ cycloalkyl, heterocyclyl or aryl each independently optionally is substituted with one or more substituents, wherein R$^7$ is H or C$_1$-C$_6$ alkyl, and n is an integer from 1-6, preferably 1-2.

Another specific and preferred embodiment of the invention relates to a selected group of Zb linkers being more hydrolytically stable during a polymerisation reaction, this group is selected from a single bond, —C(=O)—C$_1$-C$_6$ alkylene-, —SO$_2$—C$_1$-C$_6$ alkylene-, —P(=O)(OR$^7$)—(C$_1$-C$_6$ alkylene)-, —C$_3$-C$_6$ cycloalkyl, heterocyclyl, aryl and -aryl-(C$_1$-C$_6$ alkyl)-, wherein any C$_1$-C$_6$ alkylene, —C$_3$-C$_6$ cycloalkyl, heterocyclyl or aryl each independently optionally is substituted with one or more substituents, wherein R$^7$ is H or C$_1$-C$_6$ alkyl, and n is an integer from 1-6, preferably 1-2.

The optional substituents on linker -ZaZb- are selected from the group specified herein under the definition of "optionally substituted". In a preferred embodiment of the invention, the optional substituents are selected from the groups consisting of —F, —Cl, —Br, —I, —CN, —NO$_2$, —C$_1$-C$_6$ alkyl, aryl, —O—(C$_1$-C$_6$ alkyl), —C(O)—O—(C$_1$-C$_6$ alkyl), —S—(C$_1$-C$_6$ alkyl), —S(O)—(C$_1$-C$_6$ alkyl), —SO$_2$—(C$_1$-C$_6$ alkyl), —NH—C(O)—(C$_1$-C$_6$ alkyl), —C(O)—NH—(C$_1$-C$_6$ alkyl), and —C(O)—NH$_2$.

X$_1$ and X$_2$

The groups X$_1$ and X$_2$ serve to connect the quaternary ammonium N with the end groups W$_1$ and W$_2$. The size and form of these groups can be varied to adjust the properties of the photoinitiator polymer such as e.g. a polyurethane photoinitiator polymer.

X$_1$ and X$_2$ may be the same or different, and are preferably the same, for ease of chemical synthesis. X$_1$ and X$_2$ may be independently selected from optionally substituted C$_1$-C$_{12}$ alkylene, optionally substituted C$_2$-C$_{12}$ alkenylene, —O—, —S—, —NR$^4$—, —C(=O)—, —C(=NR$^3$)—, —Si(R$^3$)$_2$—O—, optionally substituted C$_3$-C$_8$ cycloalkyl, optionally substituted heterocyclyl, optionally substituted aryl, and combinations thereof, wherein R$^3$ is H or optionally substituted C$_1$-C$_{12}$ alkyl, and R$^4$ is optionally substituted C$_1$-C$_{12}$ alkyl. In that X$_1$ and X$_2$ may comprise combinations of the above-mentioned groups, the invention encompasses photoinitiator monomers in which X$_1$ and X$_2$ are made up of two or more of the above-mentioned groups in series.

Suitably, X$_1$ and X$_2$ are independently selected from optionally substituted C$_1$-C$_{12}$ alkylene, optionally substituted C$_2$-C$_{12}$ alkenylene, —O—, —S—, —NR$^4$—, —C(=O)—, —C(=NR$^3$)—, optionally substituted C$_3$-C$_8$ cycloalkyl, optionally substituted heterocyclyl, optionally substituted aryl, wherein R$^3$ is H or optionally substituted C$_1$-C$_{12}$ alkyl, preferably C$_1$-C$_6$ alkyl, more preferably C$_2$-C$_6$ alkyl, and R$^3$ is optionally substituted C$_1$-C$_{12}$ alkyl, preferably C$_1$-C$_6$ alkyl, more preferably C$_2$-C$_6$ alkyl.

Preferably the X$_1$ and/or X$_2$ may be attached to the N atom of the quaternary ammonium branching group through a —CH$_2$— group. For example, when X$_1$ and X$_2$ are one of the above described groups, such as for example, but not limited to, the combination of —C(=O)— and optionally substituted C$_1$-C$_{12}$ alkylene it is preferred that X$_1$ and X$_2$ are attached via —CH$_2$— in the C$_1$-C$_{12}$ alkylene-C(=O)—.

R$^3$ may be H. R$^3$ may alternatively be optionally substituted C$_1$-C$_6$ alkyl, such as e.g. methyl, ethyl, propyl, butyl, pentyl or hexyl. R$^4$ may be optionally substituted C$_1$-C$_6$ alkyl, such as e.g. methyl, ethyl, propyl, isopropyl, butyl, isobutyl, pentyl, or isopentyl. In preferred embodiments R$^3$ or R$^4$ are each independently C$_2$-C$_6$ alkyl.

X$_1$ and X$_2$, or parts thereof, may be linked to one another or to linkers Z, Za, or Zb, or to R$^1$ to form one or more ring structures. X$_1$ and X$_2$ may be linked to one another to form one or more ring structures. In one embodiment of the invention X$_1$ and X$_2$ are not linked to one another or to the linkers or R$^1$.

X$_1$ and X$_2$ may independently be selected from optionally substituted C$_1$-C$_{12}$ alkylene, —O—, —S—, —NR$^4$—, wherein R$^4$ is optionally substituted C$_1$-C$_{12}$ alkyl, and combinations thereof. Additionally, X$_1$ and X$_2$ may independently be optionally substituted C$_1$-C$_{12}$ alkylene, preferably optionally substituted C$_2$-C$_6$ alkylene.

In a specific embodiment of the invention, X$_1$ and X$_2$ are independently optionally substituted C$_1$-C$_{12}$ alkylene, and W$_1$ and W$_2$ are —CH$_2$OH.

Quaternary Ammonium, N$^+$ and R$^1$

In the photoinitiator monomers of Formula (I), or the photoinitiator monomer (A) described by Formula (I), N$^+$ represents a quaternary ammonium (i.e. a nitrogen atom bound directly to four carbon atoms, in which the carbon atoms are saturated alkyl or aryl carbon atoms).

The N atom in the photoinitiator monomers in Formula (I) has a number of functions. Firstly, it provides the appropriate branching of the molecule, so that the photoinitiator moieties in the polymer photoinitiators are pendant from the polymer backbone. Secondly, it provides the desired water solubility of the photoinitiator monomers. Thirdly, the ammonium cation acts to stabilise an intermediate benzophenone radical anion by preventing back electron transfer during radical processes. Once incorporated into a cured surface coating, the quaternary ammonium moiety can additionally impart desirable antibacterial and antifouling properties on the polymer surface. By antifouling is meant prevention of accumulation of deposits of microorganisms, algae, barnacles or other marine organisms on underwater surfaces, such as ships bottoms. This effect is particularly strong when the N-atom carries long linear alkyl chains, such as chains having more than 6 carbon atoms, such as e.g. more than 7, more than 8 or more than 9 carbon atoms. Accordingly, in a preferred embodiment of the invention at least one of X$_1$, X$_2$ or R$^1$, comprises a linear alkyl chain of at least C$_6$.

A further aspect of the present invention relates to use of the quaternary ammonium polymeric photoinitiators of the invention in antimicrobial, antibacterial, antifungal or antifouling compositions. These compositions may typically be in the form of a cured surface coating or a polymer surface.

R$^1$ is selected from optionally substituted C$_1$-C$_{30}$ alkyl, optionally substituted C$_3$-C$_{30}$ alkenyl, optionally substituted C$_3$-C$_{30}$ alkynyl, optionally substituted C$_3$-C$_{12}$ cycloalkyl, optionally substituted —[(C$_1$-C$_6$ alkylene)-O—(C$_1$-C$_6$ alkylene)]$_p$—H moiety, optionally substituted heterocyclyl, and optionally substituted aryl; wherein p is an integer from 1-6.

Additionally R$^1$ may be covalently linked to X$^-$ to form a betaine-type structure. R$^1$, X$_1$ and X$_2$ or a part thereof may be linked to one another or to linker Z to form one or more ring structures.

Suitably, R$^1$ has a molecular weight of less than 5000 Da, suitably less than 1000 Da, most suitably less than 500 Da. The group R$^1$ preferably comprises no more than 50 atoms, preferably no more than 30 atoms.

In one preferred embodiment of the invention R$^1$ is selected from optionally substituted C$_1$-C$_{20}$ alkyl, optionally substituted C$_3$-C$_{20}$ alkenyl, optionally substituted C$_3$-C$_{20}$ alkynyl, optionally substituted C$_3$-C$_8$ cycloalkyl, optionally substituted —[(C$_1$-C$_6$ alkylene)-O—(C$_1$-C$_6$ alkylene)]$_p$—H moiety, optionally substituted heterocyclyl, and optionally substituted aryl; wherein p is an integer from 1-2.

In another preferred embodiment of the invention $R^1$ is selected from optionally substituted $C_1$-$C_{20}$ alkyl, optionally substituted $C_3$-$C_{20}$ alkenyl, optionally substituted $C_3$-$C_{20}$ alkynyl, and optionally substituted —[($C_1$-$C_6$ alkylene)-O—($C_1$-$C_6$ alkylene)]$_p$—H moiety; wherein p is an integer from 1-2.

In a specifically preferred embodiment of the invention $R^1$ is selected from optionally substituted $C_6$-$C_{20}$ alkyl, optionally substituted $C_6$-$C_{20}$ alkenyl, optionally substituted $C_6$-$C_{20}$ alkynyl, and optionally substituted —[($C_3$-$C_6$ alkylene)-O—($C_3$-$C_6$ alkylene)]$_p$—H moiety; wherein p is an integer from 1-2, and alkyl, alkylene, alkenyl or alkynyl are linear. More preferably the alkyl, alkylene, alkenyl or alkynyl are unsubstituted.

The linkers Z, Za, Zb, $R^1$, $X_1$, and $X_2$ are selected such that N is a quartenary ammonium (i.e. so that the atom adjacent N is a saturated carbon atom, or an aryl carbon atom). Preferably, at least two of the groups Z, Za, Zb, $R^1$, $X_1$ and $X_2$ attached to the ammonium group are alkyl.

End Groups, $W_1$, $W_2$

The end groups $W_1$ and $W_2$ in Formula (I) allow the photoinitiator monomer to be incorporated into a growing polymer chain, such as e.g. a polyurethane chain. $W_1$ and $W_2$ are therefore selected from those functional groups which are reactive in polymerization reactions and which then are able to bond to other monomers. When the intended polymer is a polyurethane the monomers may therefore have reactive $W_1$ and $W_2$ groups in the form of —OH or —NCO, as these are able to bond to other polyurethane monomers to thus form polyurethane.

$W_1$ and $W_2$ are each independently selected from —OH (forming a secondary alcohol), —CH$_2$OH (forming a primary alcohol), —NH$_2$, —NHR$^6$, —SH, —Si(OR$^6$)$_2$—H, —SiH(R$^6$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^5$, —NH—C(O)—OR$^5$, and —OC(O)—NHR$^5$, wherein $R^5$ is H or $C_1$-$C_6$ alkyl, and wherein $R^6$ is $C_1$-$C_6$ alkyl.

Preferably, $W_1$ and $W_2$ may independently be selected from the group consisting of —OH, —CH$_2$OH, —NH$_2$, —NHR$^5$, —SH, —NCO, —NCS, and —COOH. More preferably, selected from the group consisting of —CH$_2$OH, —NH$_2$, —NHR$^5$, and —SH.

Care should be taken when selecting suitable $X_1$ and $X_2$ groups, such that $W_1$ and $W_2$ fulfil these criteria. For example, $X_1$ and $X_2$ may independently be selected from optionally substituted $C_1$-$C_{12}$ alkylene, when $W_1$ and $W_2$ are —OH.

In the definitions of $W_1$ and $W_2$, —CH$_2$OH denotes primary alcohol attached onto $X_1$ or $X_2$. In the same manner in the definitions of $W_1$ and $W_2$, —OH is to be understood as—forming a secondary alcohol with $X_1$ or $X_2$.

Secondary amines may have the formula —NHR$^5$, where $R^5$ is $C_1$-$C_6$ alkyl.

$R^5$ and $R^6$ may independently be $C_1$-$C_6$ alkyl, such as e.g. methyl, ethyl, propyl, butyl, pentyl or hexyl. $R^5$ may additionally be H.

$W_1$ and $W_2$ are selected according to the design of the polymer. If desired, $W_1$ and $W_2$ may be different end groups. It is preferably for ease of synthesis of the photoinitiator, however, that $W_1$ and $W_2$ are the same.

When $W_1$ and $W_2$ are a two alcohol groups, it is preferred that these are attached at $X_1$ and $X_2$ so as both form a primary alcohol (i.e. —CH$_2$OH), or both form a secondary alcohol (i.e. —OH in the definition of $W_1$ and $W_2$). Hereby allowing for symmetric growth of the polymer chain. In the same manner, it is preferred that when $W_1$ and $W_2$ are two amine groups, i.e. —NH$_2$ or —NHR$^6$, they are either two primary amine groups or two secondary amine groups.

Accordingly, in one embodiment of the present invention $W_1$ and $W_2$ are selected from the group consisting of —OH (forming a secondary alcohol), —CH$_2$OH (forming a primary alcohol), —NH$_2$, —NHR$^6$, —SH, —Si(OR$^6$)$_2$—H, —SiH(R$^5$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^6$, —NH—C(O)—OR$^5$, and —OC(O)—NHR$^5$, wherein $R^5$ is H or $C_1$-$C_6$ alkyl, $R^6$ is $C_1$-$C_6$ alkyl, and wherein $W_1$ and $W_2$ are the same.

In a preferred embodiment of the invention $W_1$ and $W_2$ are selected from the group consisting of —OH (forming a secondary alcohol), —CH$_2$OH (forming a primary alcohol), —NH$_2$, —NHR$^6$, —SH, —NCO, —NCS, and —COOH; and more preferably from the group consisting of —OH, —CH$_2$OH, —NH$_2$, —NHR$^6$, and —SH; wherein $W_1$ and $W_2$ are the same.

A preferred embodiment of the invention relates to photoinitiator monomers of general formula (I), or subformulas thereof, where $W_1$ and $W_2$ are the same and either —OH or —CH$_2$OH. Likewise, a preferred embodiment of the second aspect of the invention relates to a polymeric photoinitiator which is a co-polymer of at least one monomer (A) with at least one monomer (B), where the polymer is a polyurethane and photoinitiator monomer (A) is of general formula (I), or subformulas thereof, where $W_1$ and $W_2$ are the same and either —OH or —CH$_2$OH.

In that only two end groups $W_1$ and $W_2$ are present, the photoinitiator monomer does not promote branching of the polyurethane. Instead, the photoinitiator monomers of Formula (I) are incorporated partly into the polymer chain, while the photoinitiator moieties are pendant from the chain via the linkers Z or -Za-Zb-.

Specific Photoinitiator Monomers

Suitable photoinitiator monomers according to the invention include:

4-({[(4-benzoylphenyl)methyl]bis(2-hydroxyethyl) ammoniumyl}methyl)benzoate;

[(4-benzoylphenyl)methyl]bis[2-(2-hydroxyethoxy)ethyl] methylammonium bromide;

[2-(4-benzoylphenyl)-2-oxoethyl]bis(2-hydroxyethyl)methylammonium bromide;

[2-(2-benzoylbenzoyloxy)ethyl]bis(2-hydroxyethyl)methylammonium bromide;

[3-(4-benzoylphenoxy)propyl]bis(2-hydroxyethyl)methylammonium bromide;

[3-(4-benzoylphenoxy)propyl](benzyl)bis(2-hydroxyethyl) ammonium bromide;

3-{[3-(4-benzoylphenoxy)propyl]bis(2-hydroxyethyl) ammonium}propane-1-sulfonate;

{2-[(4-benzoylphenyl)sulfanyl]ethyl}(ethyl)bis(2-hydroxyethyl)ammonium iodide;

[2-(4-benzoylphenoxy)ethyl]bis(2-hydroxypropyl)methylammonium 4-methylbenzene-1-sulfonate;

2-{[2-(4-benzoylphenoxy)ethyl]bis(2-hydroxyethyl) ammoniumyl}ethane-1-sulfonate;

2-[bis(2-aminoethyl) [3-(4-benzoylphenoxy)propyl]ammoniumyl]acetate;

{3-[(1-chloro-9-oxo-9H-thioxanthen-4-yl)oxy]propyl}bis (2-hydroxyethyl)methylammonium bromide;

{3-[(1-chloro-9-oxo-9H-thioxanthen-4-yl)oxy]propyl}bis (2-hydroxyethyl)ethylammonium iodide;

2-({3-[(1-chloro-9-oxo-9H-thioxanthen-4-yl)oxy]
propyl}bis(2-hydroxyethyl)ammoniumyl)ethane-1-sulfonate;
bis(2-hydroxyethyl)methyl[2-({2-[(9-oxo-9H-thioxanthen-2-yl)oxy]acetyl}oxy)ethyl]ammonium chloride;
(cyanomethyl)({2-[4-(2-hydroxy-2-methylpropanoyl)phenoxy]ethyl})bis(2-hydroxyethyl)ammonium 4-bromobenzene-1-sulfonate; or
benzyl({3-[(1-chloro-9-oxo-9H-thioxanthen-4-yl)oxy]propyl})bis(2-hydroxyethyl)ammonium bromide.

Preferred photoinitiator monomers according to the invention include:
[3-(4-benzoylphenoxy)propyl]bis(2-hydroxyethyl)methylammonium bromide;
[3-(4-benzoylphenoxy)propyl](benzyl)bis(2-hydroxyethyl)ammonium bromide;
3-{[3-(4-benzoylphenoxy)propyl]bis(2-hydroxyethyl)ammonium}propane-1-sulfonate;
4-({[(4-benzoylphenyl)methyl]bis(2-hydroxyethyl)ammoniumyl}methyl)benzoate;
{3-[(1-chloro-9-oxo-9H-thioxanthen-4-yl)oxy]propyl}bis(2-hydroxyethyl)methylammonium bromide; or
benzyl({3-[(1-chloro-9-oxo-9H-thioxanthen-4-yl)oxy]propyl})bis(2-hydroxyethyl)ammonium bromide.

Polymeric Photoinitiators

A second aspect of the invention relates to a polymeric photoinitiators, being a co-polymer of at least one monomer (A) with at least one monomer (B), wherein:
monomer (A) is a photoinitiator monomer (A) of the general formula (I):

(I)

wherein general formula (I), or subformulas (II), (III), (IIIa), (IV), (IVa), (IVb), (IVc), (V), and (Va), including preferred options, is as defined herein for the photoinitiator monomers of general formula (I);
monomer (B) comprises at least two functional groups $W_3$ and $W_4$, said $W_3$ and $W_4$ being independently selected from halogen, —OH (forming a secondary alcohol), —CH$_2$OH (forming a primary alcohol), —NH$_2$, —NHR$^{10}$, —SH, —Si(OR$^{10}$)$_2$—H, —SiH(R$^{10}$)$_2$, —C(=O)—OSi(R$^{10}$)$_3$, —NCO, —NCS, —COOH, —COOR$^{10}$, —COO-aryl, —C(=O)—Cl, —O—C(=O)—Cl, —C(O)—NH$_2$, —C(O)—NHR$^9$, —NH—C(O)—OR$^9$, and —OC(O)—NHR$^9$, wherein R$^9$ is H or C$_1$-C$_6$ alkyl, and wherein R$^{10}$ is C$_1$-C$_6$ alkyl;
wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

Preferred options of R$^9$ and R$^{10}$ are as described herein for R$^5$ and R$^6$, mutatis mutandis.

In a preferred embodiment of the invention $W_3$ and $W_4$ are independently selected from halogen, —OH, —CH$_2$OH, —NH$_2$, —NHR$^{10}$, —SH, —C(=O)—OSi(R$^{10}$)$_3$, —NCO, —NCS, —COOH, —COOR$^{10}$, —COO-aryl, —C(=O)—Cl, —O—C(=O)—Cl, —C(O)—NH$_2$, —C(O)—NHR$^9$, —NH—C(O)—OR$^9$, and —OC(O)—NHR$^9$, wherein R$^9$ is H or C$_1$-C$_6$ alkyl, and wherein R$^{10}$ is C$_1$-C$_6$ alkyl.

Accordingly, the definitions of Pi, Z, n, $X_1$, $X_2$, $W_1$, $W_2$, $R^1$, $R^2$, $R^3$, $R^4$, $R^5$, $R^6$, $R^7$, and $R^8$, as described herein in connection with the first aspect of the invention, apply for the second aspect of the invention as well. Polymerization of the polymeric photoinitiator is achieved by step-growth co-polymerization of monomers (A) and (B). The physical, chemical and photocatalytic properties of the polymeric photoinitiator can be varied depending on the nature and relative amounts of the monomers (A) and (B).

Accordingly, the definitions of Pi, Z, Za, Zb, $R^1$, $X_1$, $X_2$, $W_1$, $W_2$, $R^2$, $R^3$, $R^4$, $R^5$, $R^6$, $R^7$, and $R^8$, as described herein in connection with the first aspect of the invention, applies for the second aspect of the invention as well. Polymerization of the polymeric photoinitiator is achieved by step-growth co-polymerization of monomers (A) and (B). The physical, chemical and photocatalytic properties of the polymeric photoinitiator can be varied depending on the nature and relative amounts of the monomers (A) and (B).

Monomer (B) may have a structure of formula (VI):

(VI)

wherein $W_3$ and $W_4$ are defined above and wherein Q is selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl, —[O—(C$_1$-C$_{12}$ alkylene)]$_m$—, —[S—(C$_1$-C$_{12}$ alkylene)]$_m$—, where m is an integer from 1-1000, and combinations thereof. Q could also comprise one of the photoinitiator moieties (Pi) set out above.

As an example, Q may for instance be a dicyclohexylmethylene and would then, in the above definition correspond to a (C$_3$-C$_8$ cycloalkyl)-(C$_1$-C$_{12}$ alkylene)-(C$_3$-C$_8$ cycloalkyl) moiety.

Q may be selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl and combinations thereof.

Q may be selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, and optionally substituted biaryl. Q may be selected from the group consisting of optionally substituted aryl and optionally substituted biaryl.

Preferably $W_3$ and $W_4$ may each independently be selected from isocyanate and thioisocyanate groups (i.e. —NCO and —NCS). Preferably $W_3$ and $W_4$ may be the same functional groups.

In particular embodiments, monomer (B) is a polyisocyanate, preferably a diisocyanate. Suitable polyisocyanates have an average of about two or more isocyanate groups, preferably an average of about two to about four isocyanate groups and include aliphatic, cycloaliphatic, aralkyl and aromatic polyisocyanates, used alone or in mixtures of two or more. Diisocyanates are preferred; this is for example the case where the polymeric photoinitiator is a polyurethane.

Specific examples of suitable aliphatic polyisocyanates include alpha, omega-alkylene diisocyanates having from 5 to 20 carbon atoms, such as hexamethylene-1,6-diisocyanate, 1,12-dodecane diisocyanate, 2,2,4-trimethyl-hexamethylene diisocyanate, 2,4,4-trimethyl-hexa methylene diisocyanate, 2-methyl-1,5-pentamethylene diisocyanate and the like. Polyisocyanates having fewer than 5 carbon atoms can be used but are less preferred because of their high volatility and toxicity. Preferred aliphatic polyisocyanates include hexa methylene-1,6-diisocyanate, 2,2,4-trimethyl-hexa methylene-diisocyanate and 2,4,4-trimethyl-hexamethylene diisocyanate.

Specific examples of suitable cycloaliphatic polyisocyanates include dicyclohexylmethane diisocyanate, isophorone diisocyanate, 1,4-cyclohexane diisocyanate, 1,3-bis-(isocyanatomethyl)cyclohexane and the like. Preferred cycloaliphatic polyisocyanates include dicyclohexylmethane diisocyanate and isophorone diisocyanate.

Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate, and the like. A preferred araliphatic polyisocyanate is tetramethyl xylylene diisocyanate.

Examples of suitable aromatic polyisocyanates include 4,4'-diphenylmethylene diisocyanate, toluene diisocyanate, their isomers, naphthalene diisocyanate and the like. A preferred aromatic polyisocyanate is toluene diisocyanate.

Monomer (B) may be selected from the group consisting of: 1,4-phenylene diisocyanate (PPDI), toluene diisocyanate (TDI) as both its 2,4 and 2,6 isomers, methylene diphenyl diisocyanate (MDI) as both its 4,4' and 2,4' isomers, 1,5-naphthalene diisocyanate (NDI), 3,3'-bitolylene-4,4'-diisocyanate (TODI), 1,3-xylylenediisocyanate (XDI), tetra methyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI) and 1,3-bis(isocyanato-methyl)cyclohexane (HXDI).

Importantly, $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety. In a preferred embodiment of the second aspect of the invention $W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety. Of most interest is the situation in which $W_1$ reacts with $W_3$ to form a urethane, or thiourethane moiety, and $W_2$ reacts with $W_4$ to form a urethane or thiourethane moiety.

Given a particular $W_1$ or $W_2$, the skilled person will be able to select the appropriate $W_3$ or $W_4$ to provide the polymeric photoinitiator monomers of the invention.

Preferably, the polymeric photoinitiator is a polyurethane photoinitiator. In this case, $W_1$ and $W_2$ are selected to be alcohol functional groups, and $W_3$ and $W_4$ are selected as isocyanate groups to provide urethane moieties when monomer (A) reacts with monomer (B). A polyurethane photoinitiator will thus be formed. The reverse arrangement ($W_1$ and $W_2$ are isocyanate functional groups, while $W_3$ and $W_4$ are alcohol groups) will also provide a polyurethane. In this case in a preferred embodiment of monomer (A) $W_1$ and $W_2$ are selected so as both the alcohol functional groups are either primary (—CH$_2$OH) or secondary alcohol (i.e. —OH in the definition of $W_1$ and $W_2$) groups.

Similarly, if $W_1$ and $W_2$ are thiol functional groups, selection of $W_3$ and $W_4$ as isocyanate groups will provide thiourethane moieties when monomer (A) reacts with monomer (B). The reverse arrangement is also possible.

To form urea moieties from $W_1$-$W_4$, it is possible to select $W_1$ and $W_2$ as amine functional groups and $W_3$ and $W_4$ as isocyanate functional groups. Polyurea photoinitiators will thus be formed. The reverse situation is also possible ($W_1$ and $W_2$ are isocyanate functional groups, while $W_3$ and $W_4$ are amine functional groups). In this case in a preferred embodiment of monomer (A), $W_1$ and $W_2$ are selected so as both the amine functional groups are either primary or secondary amine groups.

Suitably, $W_3$ and $W_4$ are the same functional groups, as are $W_1$ and $W_2$. However, it is possible that $W_1$ and $W_2$ are different, as long as $W_3$ and $W_4$ are selected such that a polymer may be formed.

More than one type of monomer (A) and more than one type of monomer (B) may be used in the polymeric photoinitiators of the invention. As well as the regular structure . . . ABABABAB . . . , the polymeric photoinitiators may therefore also have a structure which incorporates variations of monomers A and B, e.g. . . . A'BABA'B'A-'B'A'BABA'B' . . . .

One or more additional monomers (C) may also be present in the polymeric photoinitiators of the invention. Each of said one or more additional monomers (C) comprises at least two functional groups $W_5$ and $W_6$, said $W_5$ and $W_6$ being independently selected from —OH (forming a secondary alcohol), —CH$_2$OH (forming a primary alcohol), —NH$_2$, —NHR$^{12}$, —SH, —Si(OR$^{12}$)$_2$—H, —C(=O)—OSi(R$^{12}$)$_3$, —SiH(R$^{12}$)$_2$, —NCO, —NCS, —COOH, —COOR$^{12}$, —COO-aryl, —C(=O)—Cl, —O—C(=O)—Cl, —C(O)—NH$_2$, —C(O)—NHR$^{11}$, —NH—C(O)—OR$^{11}$, and —OC(O)—NHR$^{11}$, wherein R$^{11}$ is H or C$_1$-C$_6$ alkyl, and wherein R$^{12}$ is C$_1$-C$_6$ alkyl; and wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety. Suitably, $W_5$ reacts with $W_1$ or $W_3$ to form a urethane, thiourethane, urea, thiourea, ester or amide moiety, and $W_6$ reacts with $W_2$ or $W_4$ to form a urethane, thiourethane, urea, thiourea, ester, or amide moiety. Preferred options of R$^1$ and R$^{12}$ are as described herein for R$^5$ and R$^6$, mutatis mutandis.

In a preferred embodiment of the invention $W_5$ and $W_6$ are independently selected from halogen, —OH, —CH$_2$OH, —NH$_2$, —NHR$^{12}$, —SH, —C(=O)—OSi(R$^{12}$)$_3$, —NCO, —NCS, —COOH, —COOR$^{12}$, —COO-aryl, —C(=O)—Cl, —O—C(=O)—Cl, —C(O)—NH$_2$, —C(O)—NHR$^{11}$, —NH—C(O)—OR$^{11}$, and —OC(O)—NHR$^{11}$, wherein R$^{11}$ is H or C$_1$-C$_6$ alkyl, and wherein R$^{12}$ is C$_1$-C$_6$ alkyl.

In one embodiment of the invention, where one or more additional monomers (C) are present, these may be a macromonomer selected from polyether, polyester, polycarbonate, polyamine, and polydisulfide having the herein above or below described two functional groups $W_5$ and $W_6$. Suitably, polyether macromonomer (C) may be of a molecular weight between 200 and 20,000, more suitably between 200 and 15,000, even more suitably between 200 and 10,000, yet even more suitable between 1000 and 8,000, such as e.g. a polyethylene glycol (PEG), polypropylene glycol (PPG), random or block poly(ethylene glycol)-poly(propylene glycol) copolymer or poly(tetramethylene glycol) (PTMG). Suitably, polyester macromonomer (C) may be of a molecular weight between 200 and 10,000, such as e.g. 200 and 8,000, these being e.g. diol end-capped poly(1,4-butanediol adipate), poly(ethanediol 1,4-butanediol adipate), poly(caprolacton) diol or poly(ethylene terephthalate) diol. Suitably, polycarbonate macromonomer (C) may be of a molecular weight between 500 and 10,000, such as e.g. poly(hexamethylene carbonate) diol. Suitably, polyamine macromonomer (C) may be of a molecular weight between 500 and 10,000, such as e.g. a hydroxyl end-functionalised poly(2-methyl-2-oxazoline). Suitably, polydisulfide macromonomer (C) may be of a molecular weight between 1000 and 10,000, such as e.g. Thiokol® LP thiol end-capped polymer (e.g. Thiokol® LP-32 or Thiokol® LP-33).

Depending on the choice of $W_5$ and $W_6$, and the relative amounts of monomers (A), (B) and (C), the polymeric photoinitiator may have a variety of repeating structures such as e.g.:

...ABABABABCBABABCBAB... (if $W_5$ and $W_6$ react with $W_3$ and $W_4$).

...ABABACACABABABACAC... (if $W_5$ and $W_6$ react with $W_1$ and $W_2$)

Monomer (C) may have a structure of formula (VII):

$$W_5\text{-}T\text{-}W_6 \quad (VII)$$

wherein $W_5$ and $W_6$ are defined above, and wherein T is selected from the group consisting of optionally substituted $C_1$-$C_{12}$ alkylene, optionally substituted $C_1$-$C_{12}$ alkenylene, optionally substituted $C_3$-$C_8$ cycloalkyl, optionally substituted $C_3$-$C_{12}$ heterocyclyl, optionally substituted aryl, optionally substituted biaryl, $-[O-(C_1\text{-}C_{12}\text{ alkylene})]_m-$, $-[S-(C_1\text{-}C_{12}\text{ alkylene})]_m-$, where m is an integer from 1-1000, and combinations thereof. T may be selected from the group consisting of $-[O-(C_1\text{-}C_{12}\text{ alkylene})]_m-$, $-[S-(C_1\text{-}C_{12}\text{ alkylene})]_m-$, where m is an integer from 1-1000.

Suitably, $W_5$ and $W_6$ are independently selected from —OH (forming a secondary alcohol), —CH$_2$OH (forming a primary alcohol), —NH$_2$, —NHR$^{12}$, and —SH; preferably —OH or —CH$_2$OH. Typically, $W_5$ and $W_6$ are the same functional groups. In one embodiment of the invention where monomer C is a polyether macromonomer, one of $W_5$ and $W_6$ are —OH (forming a secondary alcohol), and the other is —CH$_2$OH (forming a primary alcohol).

Monomer (C) may be used to determine the physical properties of the polymeric photoinitiator. Monomer (C) may e.g. promote water solubility. Suitably, monomer (C) may be a macromonomer, i.e. a polymer or oligomer that has a functional group that can take part in further polymerization. As such, monomer (C) may be selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly(ethanediol 1,4-butanediol adipate), poly(caprolacton) diol, poly(1,6-hexanediol carbonate) and poly(ethylene terephthalate) diol. Monomer (C) may also comprise diols of other poly($C_1$-$C_6$) alkylene oxides.

Monomer (C) could also be a low molecular weight monomer, such as a $C_1$-$C_{10}$ diol, e.g. 1,2-ethanediol, 1,3-propanediol or 1,4-butanediol.

The weight ratio of monomers (A):(B) is suitably 1:99-99:1, preferably 1:99-50:50. The weight ratio of monomers (A):(C) is suitably 1:99-99:1, preferably 1:99-50:50. The weight of the photoinitiator monomer (A) used to prepare polymeric photoinitiators may be between 0.1% and 99% of the total mass of other monomers, suitably between 0.2% and 10%, most suitably 0.5% to 5%.

Suitably, the polymeric photoinitiator has a molecular weight of more than 1 kDa, suitably between 10 kDa and 1000 kDa, most suitably between 20 kDa and 100 kDa.

In the polymeric photoinitiator, the photoinitiator moiety Pi is pendant from the polymer backbone. As such, it is not able to leach from the polymer matrix. In addition, radical bond-forming reactions between the photoinitiator moiety and other components of the polymerization mixture will cause cross-linking, rather than forming undesirable low molecular weight compounds.

One or more additional monomers (D) may also be present in the polymeric photoinitiators of the invention. Monomer (D) may be selected from $R^{10}$—PCl$_2$, $Ar^3$—PCl$_2$, $R^{10}$—P($=$O)Cl$_2$, $Ar^3$—P($=$O)Cl$_2$, $R^{10}$—O—P($=$O)Cl$_2$, $Ar^3$—O—P($=$O)Cl$_2$, wherein $R^{10}$ is optionally substituted $C_1$-$C_{12}$ alkyl and $Ar^3$ is optionally substituted aryl. Examples of such monomers include, but are not limited to, phenyldichlorophosphine ($C_6H_5$—PCl$_2$), methylphosphonic dichloride (CH$_3$—P($=$O)Cl$_2$) and methyl dichlorophosphate (CH$_3$—O—P($=$O)Cl$_2$). These monomers (D) may be used in preparing polymeric photoinitiators of the invention by co-polymerization with monomer (A) alone or together with other monomers (B) or (C), such as are described herein in relation to the second aspect of the invention. Monomers (D) may furthermore be used in polymeric photoinitiators of the invention incorporated into a polyacrylate according to the third aspect of the invention. Monomers (D) are suitable for making polyphosphonites, polyphosphonates and polyphosphates.

Further Aspects of the Invention Relating to Polymeric Photoinitiators

The invention further relates to a method for producing a polymeric photoinitiator, said method comprising step-growth co-polymerization of at least one monomer (A) with at least one monomer (B), wherein (A) and (B) have the structures described herein above. Preferably the polymeric photoinitiator is a polyurethane photoinitiator. The co-polymerization reaction may additionally comprise one or more additional monomers (C), having the structure described herein above. Co-polymerization of monomers (A) and (B) may take place using any suitable reaction conditions, catalysts or reagents known to the skilled person. For instance, amines such as DABCO are known to catalyse polyurethane formation.

A variant of the second aspect of the invention is accordingly a method of preparing a polymeric quaternary ammonium photoinitiator comprising the following steps:

i) providing a monomer (A) of the general formula (I):

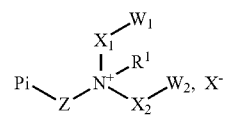

wherein general formula (I), or subformulas (II), (III), (IIIa), (IV), (IVa), (IVb), (IVc), (V), and (Va), including preferred options, is as defined herein for the photoinitiator monomers of general formula (I);

ii) providing a monomer (B);

wherein monomer (B) comprises at least two functional groups $W_3$ and $W_4$, said $W_3$ and $W_4$ being independently selected from halogen, —OH (forming a secondary alcohol), —CH$_2$OH (forming a primary alcohol), —NH$_2$, —NHR$^{10}$, —SH, —Si(OR$^{10}$)$_2$—H, —SiH(R$^{10}$)$_2$, —C($=$O)—OSi(R$^{10}$)$_3$, —NCO, —NCS, —COOH, —COOR$^{10}$, —COO-aryl, —C($=$O)—Cl, —O—C($=$O)—Cl, —C(O)—NH$_2$, —C(O)—NHR$^9$, —NH—C(O)—OR$^9$, and —OC(O)—NHR$^9$, wherein $R^9$ is H or $C_1$-$C_6$ alkyl, and $R^{10}$ is $C_1$-$C_6$ alkyl; and iii) preparing a co-polymer of at least one monomer (A) with at least one monomer (B), wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

The polymeric photoinitiators (e.g. polyurethane photoinitiators) of the present invention form radical species upon exposure to radiation and/or heat. Application of radiation (as described in the section above entitled "Curing") excites the photoinitiator moiety, Pi, which then extracts protons from neighbouring functionalities, forming reactive radicals.

If the polymeric photoinitiator is the only component when irradiated, it will cross-link with itself, providing a cured polymer. The invention thus provides a method of cross-linking the polymeric photoinitiator of the invention, said method comprising exposing the polymeric photoinitiator as described herein to UV radiation and/or heat.

If the polymeric photoinitiator of the invention is mixed with monomers which can undergo radical polymerization (e.g. alkene monomers or acrylate monomers), rapid curing (=polymerization and cross-linking) of such monomers can occur. The present invention thus provides the use of a polymeric photoinitiator as described herein as a photoinitiator of radical polymerization.

It has been found that the polymeric photoinitiators of the present invention act to cure polymer matrices, at least as effectively, if not more effectively than known photoinitiators.

Additionally, the present invention relates to use of a photoinitiator monomer according to the first aspect of the invention of formula (I), or subformulas thereof, in preparation of a polymeric photoinitiator. When used in this manner the photoinitiator monomers of formula (I) becomes incorporated by covalent bonds as monomers into the polymer via the two functional groups ($W_1$ and $W_2$). Accordingly, the present invention provides the use of photoinitiator monomers of formula (I) for incorporation as monomers into a polymer backbone via the functional groups $W_1$ and $W_2$. Preferably, said polymer may be a polyurethane, such as e.g. a polyalkyletherurethane, a polyurea, a polythiourethane, a polythiourea, a polydithiourethane, a polyester, a polycarbonate, a polyphosphonite, a polyphosphonate, or a polyphosphate; more preferably said polymer may be a polyurethane, a polyurea, a polyester, or polycarbonate; even more preferably a polyurethane, a polyurea, or a polyester; and yet even more preferably a polyurethane, such as e.g. a polyalkyletherurethane. Further details about the different types of polymers, or suitable W1 and W2 groups for such types of polymers, are described herein elsewhere and applies in full for this aspect of the invention.

Polyacrylate Polymers

The third aspect of the present invention provides a polyacrylate. A polyacrylate is a polymer based on acrylate monomers (Ac) comprising the moiety C=C—C(=O)—O—, which polymerize at the alkene functional group.

The polyacrylate is obtained by radical polymerization of at least one acrylate monomer (Ac) in the presence of a polymeric photoinitiator. The polymeric photoinitiator is a co-polymer of at least one monomer (A) with at least one monomer (B):

monomer (A) is a photoinitiator monomer of the formula (I):

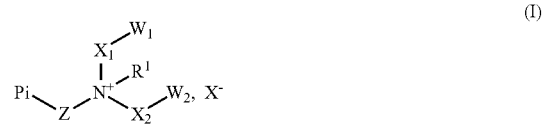

wherein general formula (I), or subformulas (I). (II), (III), (IIIa), (IV), (IVa), (IVb), (IVc), (V), or (Va), including preferred options of these, is as defined herein for the photoinitiator monomers of general formula (I);

monomer (B) is as defined herein for the second aspect of the invention.

wherein—in the co-polymerization of monomers (A) and (B) in the polymeric photoinitiator —$W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

Accordingly, the definitions of Pi, Z, Za, Zb, $R^1$, $X_1$, $X_2$, $W_1$, $W_2$, $R^2$, $R^3$, $R^4$, $R^5$, $R^6$, $R^7$, and $R^8$, and preferred options of these, as described herein in connection with the first aspect of the invention, applies for the third aspect of the invention as well. Additionally the definitions of monomer (B), (C), and (D), and preferred options of these, together with the polymeric photoinitiator of the second aspect of the invention, applies for the third aspect of the invention mutatis mutandis. For example in a preferred embodiment both $W_1$ and $W_2$ are alcohol functional groups and both $W_3$ and $W_4$ are isocyanate functional groups.

Polymerization is achieved by step-growth co-polymerization of monomers (A) and (B). The physical, chemical and photocatalytic properties of the polymeric photoinitiator can be varied depending on the nature and relative amounts of the monomers (A) and (B).

In the polymeric photoinitiator, the photoinitiator moiety Pi is pendant from the polymer backbone. As such, it is not able to leach from the polymer matrix or the polyacrylate. In addition, radical bond-forming reactions between the photoinitiator moiety and the acrylate monomer (Ac) will cause cross-linking between these components, rather than forming undesirable low molecular weight compounds.

The polymeric photoinitiators (e.g. polyurethane photoinitiators) form radical species upon exposure to radiation and/or heat. Application of radiation (as described in the section above entitled "Curing") excites the photoinitiator moiety, Pi, which then extracts protons from neighbouring functionalities, forming reactive radicals.

When the polymeric photoinitiator of the invention is mixed with acrylate monomers (Ac), these reactive radicals undergo chain propagation with the acrylate monomers (Ac), and rapid curing of such monomers can occur. As growth is initiated from the polymeric photoinitiator, the polymeric photoinitiator will itself be incorporated by means of covalent bonds into the growing polyacrylate. Scheme 2 gives an example of how the polymeric photoinitiator of the invention may be used in preparing a polyacrylate and especially how the polymeric photoinitiator itself becomes an integral part of the thereby formed polyacrylate.

Scheme 2

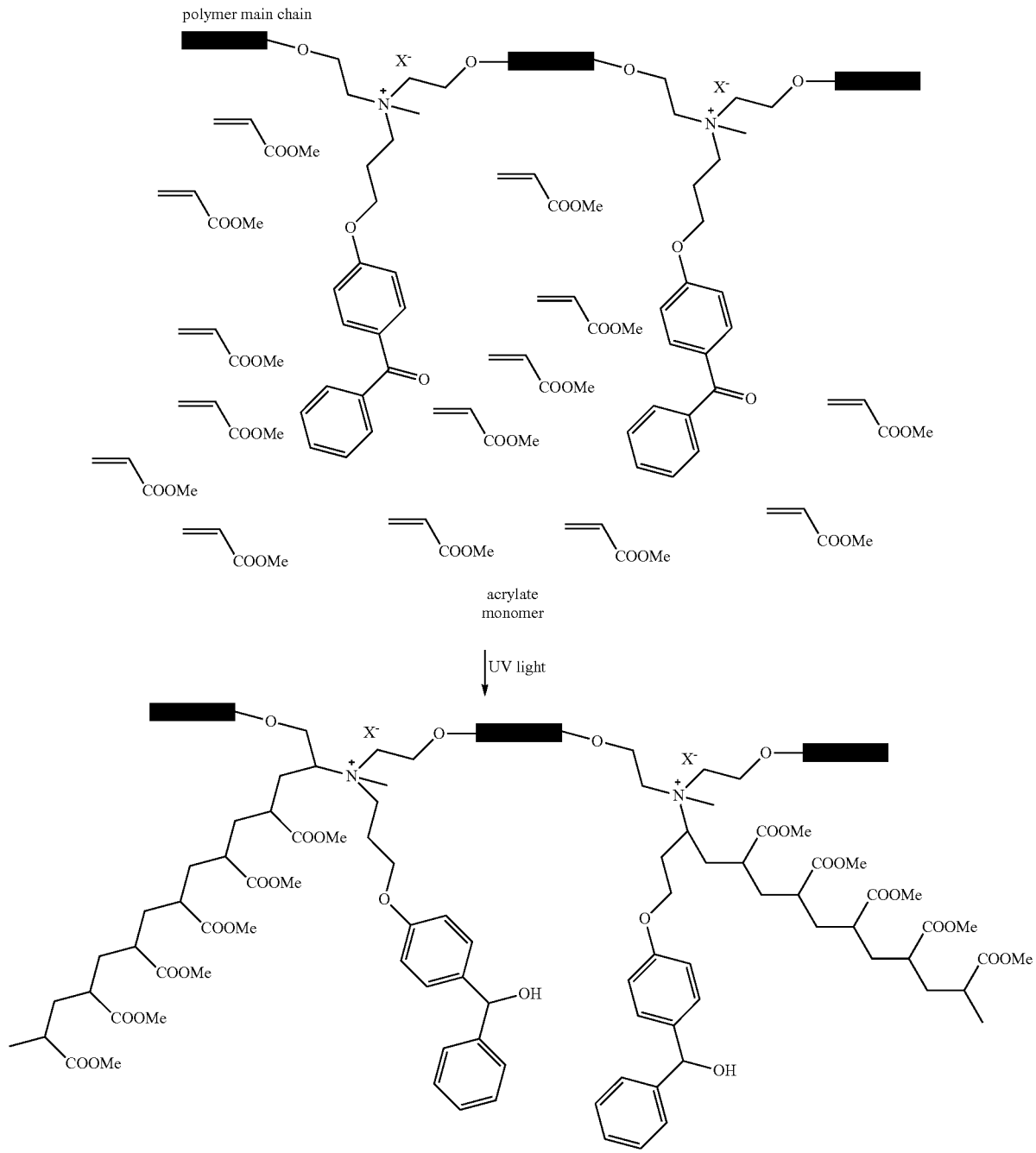

When polyacrylates are made in accordance with the invention, no amine synergists are necessarily required as the quaternary ammonium group of the polymeric photoinitiator may provide this effect in itself. The acrylate monomer (Ac) used in the invention may be a mono-, di- or tri-acrylate (i.e. comprising one, two or three C=C—C(=O)—O— moieties, respectively, or the corresponding N derivative C=C—C(=O)—N—). Preferably, the acrylate monomer is a mono-acrylate.

Examples of acrylate monomers (Ac) useful in the present invention include ethylenically unsaturated monocarboxylic and dicarboxylic acids, such as acrylic acid, methacrylic acid, itaconic acid, maleic acid and fumaric acid, and monoalkyl esters of dicarboxylic acids of the type mentioned above with alkanols, preferably alkanols having from 1 to 4 carbon atoms and their N-substituted derivatives (amides), amides of unsaturated carboxylic acids, such as acrylamide, methacrylamide, N-methoxyacrylamide or methacrylamide, and N-alkylacrylamides, ethylenic monomers containing a sulphonic acid group and ammonium or alkali metal salts thereof, for example vinylsulphonic acid, vinylbenzenesulphonic acid, alpha-acrylamidomethylpropanesulphonic acid and 2-sulphoethylene methacrylate, amides of vinylamine, especially vinylformamide or vinylacetamide, and unsaturated ethylenic monomers containing a secondary, tertiary or quaternary amino group, or a heterocyclic group containing nitrogen, such as, for example, vinylpyridines, vinylimidazole, aminoalkyl (meth)acrylates and aminoalkyl (meth)acrylamides such as dimethylaminoethyl acrylate or methacrylate, di-tert-butylaminoethyl acrylate or methacrylate, dimethylaminoacrylamide or dimethylaminomethacrylamide, and 2-{[2-(acryloyloxy)ethyl](dimethyl)ammonio}-ethanesulfonate.

In addition to the above (meth)acrylates with a hydrophilic pendant chain such as poly(ethylene glycol) methyl ether acrylate may be useful.

Examples of difunctional acrylate monomers useful in the present invention include oligomers having two acrylate, methacrylate, acrylamide, or methacrylamide groups. Each of these monomers may comprise the same two functional groups or different functional groups. The difunctional acrylate monomers may preferably be selected from bisphenol A dimethacrylate, ethoxylated bisphenol A diacrylates (e.g., ethoxylated bisphenol A diacrylate with EO/phenol 1.0, 1.5, 2, 4, 10 or 15), ethoxylated bisphenol A dimethacrylates (e.g., ethoxylated bisphenol A dimethacrylate with EO/phenol 2 or 15), bisphenol A glycerolate dimethacrylate (e.g., bisphenol A glycerolate dimethacrylate with glycerol/phenol 1), polyethylene glycol diacrylates (e.g., polyethylene glycol diacrylate with average $M_n$ of 250, 575, 700, 1000, 2000, 6000 and 10000), ethylene glycol dimethacrylate, diethylene glycol dimethacrylate, triethylene glycol dimethacrylate, tetraethylene glycol dimethacrylate, polyethylene glycol dimethacrylates (e.g., polyethylene glycol dimethacrylate with average $M_n$ of 330, 550, 750, 2000, 6000 and 10000), dipropyleneglycol diacrylate, tripropyleneglycol diacrylate, polypropylene glycol diacrylates (e.g., polypropylene glycol diacrylate with $M_n$ of 800), dipropylene glycol dimethacrylate, tripropyleneglycol dimethacrylate and polypropylene glycol dimethacrylates (e.g., polypropylene glycol dimethacrylate with $M_n$ of 560), tetramethylene dimethacrylate, methylenebisacrylamide, methacryloxyethyl vinyl carbonate, methacryloxyethyl vinyl urea, divinyl benzene, diallyl itaconate, allyl methacrylate, diallyl phtalate, and polysiloxanylbisalkyl methacrylate. $M_n$ is number average molecular weight value. It is defined as arithmetic mean of the molecular weights of the individual macromolecules.

It may also be important to include zwitterionic monomers such as, for example, sulphopropyl(dimethyl)-aminopropyl acrylate.

Suitable di- or multifunctional cross-linking agents may be, but not being limited to, ethylene glycol dimethacrylate, triethylene glycol dimethacrylate, tetraethylene glycol dimethacrylate, trimethylopropane trimethacrylate, bisphenol A dimethacrylate, ethoxylate bisphenol A dimethacrylate, pentaerythritol tri- and tetrametacrylate, tetramethylene dimethacrylate, methylenebisacrylamide, methacryloxyethyl vinyl carbonate, triallylcyanurate, methacryloxyethyl vinyl urea, divinyl benzene, diallyl itaconate, allyl methacrylate, diallyl phtalate, polysiloxanylbisalkyl methacrylate and polyethylene glycol dimethacrylate.

Examples of multifunctional acrylate monomers useful in the present invention include oligomers having three or more acrylate, methacrylate, acrylamide, or methacrylamide groups. Each of these monomers may comprise the same two functional groups or different functional groups. The multifunctional acrylate monomers may preferably be selected from trimethylolpropane triacrylate, trimethylolpropane ethoxylate triacrylate (e.g., trimethylolpropane ethoxylate triacrylate with average $M_n$ of 400, 700 or 900), trimethylolpropane propoxylate triacrylate, trimethylolpropane trimethacrylate, pentaerythritol triacrylate, pentaerythritol propoxylate triacrylate, glycerol propoxylate triacrylate, triallylcyanurate, pentaerythritol tetraacrylate, pentaerythritol tetramethacrylate, di(trimethylolpropane) tetraacrylate, dipentaerythritol pentaacrylate and dipentaerythritol hexaacrylate.

Oligo- or macromeric structures of a non-toxic nature are preferred. Of these, PEG containing di- or multifunctional oligo- or macromers may be of special interest. In the present invention, polyethylene glycol dimethacrylate of an approximately molecular weight of 400 (PEG-DMA 400) and an approximately molecular weight of 1000 (PEG-DMA 1000) may be preferred as cross-linking agent.

Suitably, the acrylate monomer (Ac) is an acrylate ester of the formula (VIII):

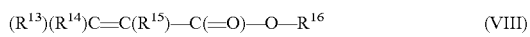
$$(R^{13})(R^{14})C=C(R^{15})-C(=O)-O-R^{16} \quad (VIII)$$

wherein $R^{13}$-$R^{15}$ are independently selected from the group consisting of H, optionally substituted $C_1$-$C_{12}$ alkyl, optionally substituted $C_1$-$C_{12}$ alkenyl, optionally substituted $C_3$-$C_{12}$ heterocyclyl and optionally substituted aryl;

and $R^{16}$ is selected from the group consisting of optionally substituted $C_1$-$C_{12}$ alkyl, optionally substituted $C_1$-$C_{12}$ alkenyl, optionally substituted $C_3$-$C_{12}$ heterocyclyl and optionally substituted aryl.

Suitably, $R_{13}$ and $R_{14}$ are independently selected from H, methyl or ethyl.

Alternatively, the acrylate monomer (Ac) may comprise a polyurethane, a polyester or a polyether oligomer having terminal acrylate groups, preferably a polyurethane oligomer having terminal acrylate groups.

The polyacrylate of the invention may comprise two or more different acrylate monomers (Ac). Different acrylate monomers (Ac) can be mixed in various ratios, depending on the desired properties of the resulting polyacrylate.

The polyacrylate of the invention may comprise additional monomers. In this way, a copolymer of the acrylate monomer(s) (Ac) with other monomers may be obtained. For example, the polymeric photoinitiator of the invention may be used to initiate the copolymerization between acrylate monomers (Ac) and monomers such as vinylethers, vinylpyrrolidone and vinyllactams, vinyl acetates and vinylalcohol, vinylamines or mixtures of these. The additional monomers should be compatible with the acrylate monomers and the polymeric photoinitiator, and should polymerize via a radical mechanism, so that they can be incorporated with the acrylate monomer (Ac). Such additional monomers provide the skilled person with further opportunities to vary the physical and chemical properties of the resulting polyacrylate.

The polymeric photoinitiators of the invention with the photoinitiator moieties incorporated as pendant groups on the polymeric backbone are capable of self-cross linking under UV light. In the presence of acrylate monomers (Ac), self-cross linking of original polymer chains and radical chain propagation of the acrylate monomers (Ac) take place. Particularly when suitable di- and/or multifunctional acrylate monomers are used, a densely cross-linked material is obtained that shows increased hardness.

Further Aspects of the Invention Relating to Polyacrylates

The present invention further provides a method for producing a polyacrylate, said method comprising the steps of:

a. combining one or more acrylate monomers with a polymeric photoinitiator, said polymeric photoinitiator being as defined herein;

b. subjecting the mixture from step a. to UV radiation and/or heat.

The present invention also provides the use of a polymeric photoinitiator as described herein as a photoinitiator of radical polymerization of acrylate monomers (Ac).

Polymeric Quaternary Ammonium Photoinitiators Prepared from Polymerized Tert-Amines A fourth aspect of the invention relates to polymeric quaternary ammonium photoinitiators obtained by preparing a polymeric photoinitiator being a co-polymer of at least one monomer (A') with at least one monomer (B), and thereafter alkylating a tertiary amine moiety of polymerized (A') with an alkylating agent.

Monomer (A') is of formula (I'), which corresponds to formula (I) as described herein above, where $R^1$ is absent and the quaternary ammonium $N^+$ atom is replaced by a tertiary amine group. Accordingly, formula (I'):

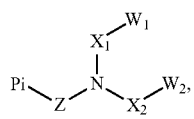

(I')

wherein Pi, Z, $X_1$, $X_2$, $W_1$, and $W_2$, each independently are as described for formula (I), mutatis mutandis.

Additionally, monomer (A') is of subformulas of formula (I'), which corresponds to the subformulas of (I), i.e. (II), (III), (IIIa), (IV), (IVa), (IVb), (IVc), (V), and (Va), where $R^1$ is absent and the quaternary ammonium $N^+$ atom is replaced by a tertiary amine group.

Monomer (B) corresponds to monomer (B), and the details of same, described herein for the second aspect of the invention.

Accordingly, the present invention relates to a polymeric quarternary ammonium photoinitiator obtained by:

i) preparing a polymeric photoinitiator being a co-polymer of at least one monomer (A') with at least one monomer (B), wherein monomer (A') is a photoinitiator monomer of formula (I'):

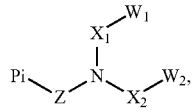

(I')

wherein

Pi is a photoinitiator moiety:

Z is a linker moiety;

$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;

$X_1$ and $X_2$ or a part thereof may be linked to one another or to linker Z, to form one or more ring structures;

Z, $X_1$ and $X_2$ are selected such that N is a tertiary amine;

$R^3$ is H or optionally substituted $C_1$-$C_{12}$ alkyl;

$R^4$ is optionally substituted $C_1$-$C_{12}$ alkyl;

$W_1$ and $W_2$ are each independently selected from —OH (forming a secondary alcohol), —$CH_2OH$ (forming a primary alcohol), —$NH_2$, —$NHR^6$, —SH, —Si($OR^6$)$_2$—H, —SiH($R^6$)$_2$, —C(=O)—OSi($R^6$)$_3$, —NCO, —NCS, —COOH, —$COOR^6$, —COO-aryl, —C(=O)—Cl, —O—C(=O)—Cl, —C(O)—$NH_2$, —C(O)—$NHR^5$, —NH—C(O)—$OR^5$, and —OC(O)—$NHR^5$;

$R^5$ is H or $C_1$-$C_6$ alkyl; and $R^6$ is $C_1$-$C_6$ alkyl; and

Monomer (B) comprises at least two functional groups $W_3$ and $W_4$, said $W_3$ and $W_4$ being independently selected from halogen, —OH, —$CH_2OH$, —$NH_2$, —$NHR^{10}$, —SH, —Si($OR^{10}$)$_2$—H, —SiH($R^{10}$)$_2$, —C(=O)—OSi($R^{10}$)$_3$, —NCO, —NCS, —COOH, —$COOR^{10}$, —COO-aryl, —C(=O)—Cl, —O—C(=O)—Cl, —C(O)—$NH_2$, —C(O)—$NHR^9$, —NH—C(O)—$OR^9$, and —OC(O)—$NHR^9$, wherein $R^9$ is H or $C_1$-$C_6$ alkyl, and wherein $R^{10}$ is $C_1$-$C_6$ alkyl;

wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety; and ii) providing an alkylating agent of formula (XII):

$$R^1\text{-LG} \qquad (XII)$$

wherein $R^1$ is selected from optionally substituted $C_1$-$C_{30}$ alkyl, optionally substituted $C_3$-$C_{30}$ alkenyl, optionally substituted $C_3$-$C_{30}$ alkynyl, optionally substituted $C_3$-$C_{12}$ cycloalkyl, optionally substituted —[($C_1$-$C_6$ alkylene)-O—($C_1$-$C_6$ alkylene)]$_p$—H moiety, optionally substituted heterocyclyl, and optionally substituted aryl, wherein p is an integer from 1-6; and LG is a leaving group;

iii) reacting said polymeric photoinitiator from step i) with alkylating agent (XII) from step ii), whereby tertiary amine moieties of the polymeric photoinitiator are alkylated by the alkylating agents, and one $R^1$ moiety become covalently linked to one tertiary amine moiety and thus forming a polymeric quaternary ammonium photoinitiator. This type of reaction is described, for example, by Król et al. in Colloid Polym. Sci. 2010 August; 288(12-13): 1255-1269 or by Frisch et al. in J. Polym. Sci. Part A: Polym. Chem. 1988, Vol 26, Issue 6, 1609-1620.

A fifth aspect of the invention relates to polymeric quaternary ammonium photoinitiators obtained by preparing a polymer being a co-polymer of at least one monomer (A") with at least one monomer (B), and thereafter alkylating a tertiary amine moiety of polymerized (A") with an alkylating agent comprising a photoinitiator.

Monomer (A") is of formula (I"), which corresponds to formula (I) as described herein above, except that Pi-Z— is absent and the quaternary ammonium $N^+$ atom is replaced by a tertiary amine group. Accordingly, formula (I"):

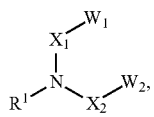

(I")

wherein $R^1$, $X_1$, $X_2$, $W_1$, and $W_2$, each independently are as described for formula (I), mutatis mutandis.

Monomer (B) corresponds to monomer (B), and the details of same, described herein for the second aspect of the invention.

Accordingly, the present invention relates to a polymeric quarternary ammonium photoinitiator obtained by:

i) preparing a polymer being a co-polymer of at least one monomer (A') with at least one monomer (B), wherein monomer (A") is a of formula (I"):

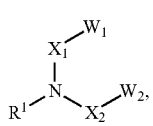

wherein
R$^1$ is selected from optionally substituted C$_1$-C$_{30}$ alkyl, optionally substituted C$_3$-C$_{30}$ alkenyl, optionally substituted C$_3$-C$_{30}$ alkynyl, optionally substituted C$_3$-C$_{12}$ cycloalkyl, optionally substituted —[(C$_1$-C$_6$ alkylene)-O—(C$_1$-C$_6$ alkylene)]$_p$—H moiety, optionally substituted heterocyclyl, and optionally substituted aryl;
p is an integer from 1-6;
X$_1$ and X$_2$ are each independently selected from optionally substituted C$_1$-C$_{12}$ alkylene, optionally substituted C$_2$-C$_{12}$ alkenylene, —O—, —S—, —NR$^4$—, —C(=O)—, —C(=NR$^3$)—, —Si(R$^3$)$_2$—O—, optionally substituted C$_3$-C$_8$ cycloalkyl, optionally substituted heterocyclyl, optionally substituted aryl, and combinations thereof;
X$_1$ and X$_2$ or a part thereof may be linked to one another or to linker Z, to form one or more ring structures;
R$^1$, X$_1$ and X$_2$ are selected such that N is a tertiary amine;
R$^3$ is H or optionally substituted C$_1$-C$_{12}$ alkyl;
R$^4$ is optionally substituted C$_1$-C$_{12}$ alkyl;
W$_1$ and W$_2$ are each independently selected from —OH (forming a secondary alcohol), —CH$_2$OH (forming a primary alcohol), —NH$_2$, —NHR$^6$, —SH, —Si(OR$^6$)$_2$—H, —SiH(R$^6$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^5$, —NH—C(O)—OR$^5$, and —OC(O)—NHR$^5$;
R$^5$ is H or C$_1$-C$_6$ alkyl; and
R$^6$ is C$_1$-C$_6$ alkyl; and
Monomer (B) comprises at least two functional groups W$_3$ and W$_4$, said W$_3$ and W$_4$ being independently selected from halogen, —OH, —CH$_2$OH, —NH$_2$, —NHR$^{10}$, —SH, —Si(OR$^{10}$)$_2$—H, —SiH(R$^{10}$)$_2$, —C(=O)—OSi(R$^{10}$)$_3$, —NCO, —NCS, —COOH, —COOR$^{10}$, —COO-aryl, —C(=O)—Cl, —O—C(=O)—Cl, —C(O)—NH$_2$, —C(O)—NHR$^9$, —NH—C(O)—OR$^9$, and —OC(O)—NHR$^9$, wherein R$^9$ is H or C$_1$-C$_6$ alkyl, and wherein R$^{10}$ is C$_1$-C$_6$ alkyl;
wherein W$_1$, W$_2$, W$_3$ and W$_4$ are selected such that—in the co-polymerization of monomers (A) and (B)—W$_1$ reacts with W$_3$ to form a urethane, thiourethane, urea, thiourea, ester, ether, amide, carbonate, allophanate or biuret moiety, and W$_2$ reacts with W$_4$ to form a urethane, thiourethane, urea, thiourea, ester, ether, amide, carbonate, allophanate or biuret moiety; and ii) providing an alkylating agent comprising a photoinitiator of formula (XIV):

Pi-Z-LG          (XIV), wherein
Pi is a photoinitiator moiety;
Z is a linker moiety; and
LG is a leaving group;
iii) reacting said polymer from step i) with alkylating agent (XIV) from step ii),
whereby tertiary amine moieties of the polymeric are alkylated by the alkylating agents, and one Pi-Z— moiety become covalently linked to one tertiary amine moiety and thus forming a polymeric quaternary ammonium photoinitiator.

Pi and Z of the alkylating agent, and the details thereof, are as described herein for the first aspect of the invention. Additionally, Pi-Z— of (XIV) may further be as described for the subformulas of (I), i.e. (II), (III), (IIIa), (IV), (IVa), (IVb), (IVc), (V), and (Va), mutatis mutandis. This corresponding to those subformulas where the moiety —N$^+$(X$_1$W$_1$)(X$_2$W$_2$)(R$^1$) is absent and replaced by a LG moiety.

In the fourth and the fifth aspect of the invention, the polymeric quaternary ammonium photoinitiator additionally comprises a counterion X'$^-$, which is a negatively charged moiety. Non-limiting examples of such counterions include fluoride, chloride, bromide, iodide, sulfate, carbonate, phosphate, tetrafluoroborate, tetraarylborate (e.g. tetraphenylborate), hexafluorophosphate, alkyl carboxylate (e.g. acetate), aryl carboxylate (e.g. benzoate), alkyl sulfonate (e.g. mesylate) and aryl sulfonate (e.g. tosylate). Preferably X'$^-$ may be selected from chloride, bromide, iodide, sulfate, tetrafluoroborate, hexafluorophosphate, acetate, benzoate, mesylate, triflate and tosylate, and more preferably X'$^-$ may be selected from chloride, bromide and iodide. Additionally X'$^-$ may be covalently bound to any carbon atom of Pi, Z, Za, Zb, R$^1$, X$_1$, X$_2$ or their optional substituents, and thereby balance the positive charge of the quaternary ammonium moiety. Non-limiting examples of such negatively-charged moieties include —SO$_3^-$, —COO$^-$, —OSO$_3^-$ and —O—P(=O)(O-alkyl)O$^-$.

The alkylating agent (XII) or (XIV) comprises a leaving group LG, which will be displaced during the alkylation of the polymeric photoinitiator. LG may be the same as X'$^-$ or different. LG-R$^1$ is for example a haloalkane, in this case R$^1$ could be e.g. an C$_1$-C$_{12}$ alkyl.

In the fourth and fifth aspect of the invention, when reacting the polymeric photoinitiator from step i) (or iii) as appropriate) with the alkylating agent provided in step ii) (or iv) as appropriate) the reaction may typically be performed in dipolar-aprotic solvents such as dimethyl sulfoxide (DMSO), sulfolane, N,N-dimethylformamide (DMF), N,N-dimethyl acetamide (DMAc), N-methylpyrrolidone (NMP) by adding C$_1$-C$_{12}$ haloalkane to the polymer solution in a concentration of from 0.1 mol per mole of tertiary amino group to 0.5 mol per mole of tertiary amino group. During evaporation of the solvent at elevated temperatures between 80° C. and 150° C., the haloalkane reacts with the tertiary amino groups on the polymer backbone with the simultaneous formation of quaternary ammonium groups.

The ratio of alkylating agent (XII) to tertiary amine moieties of the polymeric photoinitiator from step i) may be 1:99-50:50, such as e.g. 10:90, 15:85, 20:80, 25:75, 30:70, 35:65, 40:60, or 45:55, preferably 40:60-50:50.

The ratio of alkylating agent (XIV) to tertiary amine moieties of the polymer from step i) may be 1:99-50:50, such as e.g. 10:90, 15:85, 20:80, 25:75, 30:70, 35:65, 40:60, or 45:55, preferably 40:60-50:50.

By the ratio of alkylating agent to tertiary amine moieties is meant the ratio of the number of moles of the alkylating agent of formula (XII) or (XIV) to the number of moles of tertiary amine units in the polymer chain.

Accordingly, in the polymeric quaternary ammonium photoinitiator of the invention all, or only some, of the moieties arising from monomer (A') carry a quaternary ammonium moiety.

The polymeric quaternary ammonium photoinitiators of the fourth and fifth aspect of the invention, may for example be synthesised according to Schemes 4 and 5, described herein below.

A further aspect of the invention relates to a method of producing a polymeric quaternary ammonium photoinitiator, said method comprises steps i), ii), and iii), and the details of these, as described for the fourth aspect of the invention.

A variant of the fourth aspect of the invention is accordingly a method of preparing a polymeric quaternary ammonium photoinitiator comprising the following steps:

i) providing at least one monomer (A') of formula (I'):

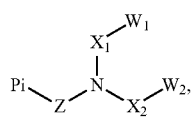

(I')

wherein
Pi is a photoinitiator moiety:
Z is a linker moiety;
$X_1$ and $X_2$ are each independently selected from optionally substituted $C_1$-$C_{12}$ alkylene, optionally substituted $C_2$-$C_{12}$ alkenylene, —O—, —S—, —NR$^4$—, —C(=O)—, —C(=NR$^3$)—, —Si(R$^3$)$_2$—O—, optionally substituted $C_3$-$C_8$ cycloalkyl, optionally substituted heterocyclyl, optionally substituted aryl, and combinations thereof;
$X_1$ and $X_2$ or a part thereof may be linked to one another or to linker Z, to form one or more ring structures;
Z, $X_1$ and $X_2$ are selected such that N is a tertiary amine;
$R^3$ is H or optionally substituted $C_1$-$C_{12}$ alkyl;
$R^4$ is optionally substituted $C_1$-$C_{12}$ alkyl;
$W_1$ and $W_2$ are each independently selected from —OH (forming a secondary alcohol), —CH$_2$OH (forming a primary alcohol), —NH$_2$, —NHR$^6$, —SH, —Si(OR$^6$)$_2$—H, —SiH(R$^6$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^5$, —NH—C(O)—OR$^5$, and —OC(O)—NHR$^5$;
$R^5$ is H or $C_1$-$C_6$ alkyl; and $R^6$ is $C_1$-$C_6$ alkyl;
ii) providing at least one monomer (B),
wherein monomer (B) comprises at least two functional groups $W_3$ and $W_4$, said $W_3$ and $W_4$ being independently selected from halogen, —OH, —CH$_2$OH, —NH$_2$, —NHR$^{10}$, —SH, —Si(OR$^{10}$)$_2$—H, —SiH(R$^{10}$)$_2$, —C(=O)—OSi(R$^{10}$)$_3$, —NCO, —NCS, —COOH, —COOR$^{10}$, —COO-aryl, —C(=O)—Cl, —O—C(=O)—Cl, —C(O)—NH$_2$, —C(O)—NHR$^9$, —NH—C(O)—OR$^9$, and —OC(O)—NHR$^9$, wherein $R^9$ is H or $C_1$-$C_6$ alkyl, and $R^{10}$ is $C_1$-$C_6$ alkyl;
wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety;

iii) preparing a polymeric photoinitiator being a co-polymer of at least one monomer (A') with at least one monomer (B);

iv) providing an alkylating agent of formula (XII):

$R^1$-LG (XII), wherein $R^1$ is selected from optionally substituted $C_1$-$C_{30}$ alkyl, optionally substituted $C_3$-$C_{30}$ alkenyl, optionally substituted $C_3$-$C_{30}$ alkynyl, optionally substituted $C_3$-$C_{12}$ cycloalkyl, optionally substituted —[(C$_1$-C$_6$ alkylene)-O—(C$_1$-C$_6$ alkylene)]$_p$—H moiety, optionally substituted heterocyclyl, and optionally substituted aryl, wherein p is an integer from 1-6; and
LG is a leaving group; and v) reacting said polymeric photoinitiator from step iii) with alkylating agent (XII) from step iv);

whereby tertiary amine moieties of the polymeric photoinitiator are alkylated by the alkylating agents, and one $R^1$ moiety become covalently linked to one tertiary amine moiety and thus forming a polymeric quaternary ammonium photoinitiator. In this variant of the fourth aspect of the invention monomer (A'), formula (I'), monomer (B) and formula (XII), including any details and preferred embodiments of these or specific moieties thereof, are as for the first, second and fourth aspect of the invention.

Yet another aspect of the invention relates to a method of producing a polymeric quaternary ammonium photoinitiator, said method comprises steps i), ii), and iii), and the details of these, as described for the fifth aspect of the invention.

A variant of the fifth aspect of the invention is accordingly a method of preparing a polymeric quaternary ammonium photoinitiator comprising the following steps:

i) providing at least one monomer (A") of formula (I"):

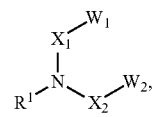

(I")

wherein
$R^1$ is selected from optionally substituted $C_1$-$C_{30}$ alkyl, optionally substituted $C_3$-$C_{30}$ alkenyl, optionally substituted $C_3$-$C_{30}$ alkynyl, optionally substituted $C_3$-$C_{12}$ cycloalkyl, optionally substituted —[(C$_1$-C$_6$ alkylene)-O—(C$_1$-C$_6$ alkylene)]$_p$—H moiety, optionally substituted heterocyclyl, and optionally substituted aryl;
p is an integer from 1-6;
$X_1$ and $X_2$ are each independently selected from optionally substituted $C_1$-$C_{12}$ alkylene, optionally substituted $C_2$-$C_{12}$ alkenylene, —O—, —S—, —NR$^4$—, —C(=O)—, —C(=NR$^3$)—, —Si(R$^3$)$_2$—O—, optionally substituted $C_3$-$C_8$ cycloalkyl, optionally substituted heterocyclyl, optionally substituted aryl, and combinations thereof;
$X_1$ and $X_2$ or a part thereof may be linked to one another or to linker Z, to form one or more ring structures;
$R^1$, $X_1$ and $X_2$ are selected such that N is a tertiary amine;
$R^3$ is H or optionally substituted $C_1$-$C_{12}$ alkyl;
$R^4$ is optionally substituted $C_1$-$C_{12}$ alkyl;
$W_1$ and $W_2$ are each independently selected from —OH (forming a secondary alcohol), —CH$_2$OH (forming a primary alcohol), —NH$_2$, —NHR$^6$, —SH, —Si(OR$^6$)$_2$—H, —SiH(R$^6$)$_2$, —C(=O)—OSi(R$^6$)$_3$, —NCO, —NCS, —COOH, —COOR$^6$, —COO-aryl, —C(=O)—Cl, —O—C(=O)—Cl, —C(O)—NH$_2$, —C(O)—NHR$^5$, —NH—C(O)—OR$^5$, and —OC(O)—NHR$^5$;

R$^5$ is H or C$_1$-C$_6$ alkyl; and R$^6$ is C$_1$-C$_6$ alkyl;

ii) providing at least one monomer (B), wherein monomer (B) comprises at least two functional groups W$_3$ and W$_4$, said W$_3$ and W$_4$ being independently selected from halogen, —OH, —CH$_2$OH, —NH$_2$, —NHR$^{10}$, —SH, —Si(OR$^{10}$)$_2$—H, —SiH(R$^{10}$)$_2$, —C(=O)—OSi(R$^{10}$)$_3$, —NCO, —NCS, —COOH, —COOR$^{10}$, —COO-aryl, —C(=O)—Cl, —O—C(=O)—Cl, —C(O)—NH$_2$, —C(O)—NHR$^9$, —NH—C(O)—OR$^9$, and —OC(O)—NHR$^9$, wherein R$^9$ is H or C$_1$-C$_6$ alkyl, and R$^{10}$ is C$_1$-C$_6$ alkyl;

wherein W$_1$, W$_2$, W$_3$ and W$_4$ are selected such that—in the co-polymerization of monomers (A) and (B)—W$_1$ reacts with W$_3$ to form a urethane, thiourethane, urea, thiourea, ester, ether, amide, carbonate, allophanate or biuret moiety, and W$_2$ reacts with W$_4$ to form a urethane, thiourethane, urea, thiourea, ester, ether, amide, carbonate, allophanate or biuret moiety;

iii) preparing a polymer being a co-polymer of at least one monomer (A') with at least one monomer (B);

iv) providing an alkylating agent comprising a photoinitiator of formula (XIV):

Pi-Z-LG  (XIV), wherein
Pi is a photoinitiator moiety;
Z is a linker moiety; and
LG is a leaving group;

v) reacting said polymer from step iii) with alkylating agent (XIV) from step iv);

whereby tertiary amine moieties of the polymeric are alkylated by the alkylating agents, and one Pi-Z— moiety become covalently linked to one tertiary amine moiety and thus forming a polymeric quaternary ammonium photoinitiator. In this variant of the fifth aspect of the invention monomer (A″), formula (I″), monomer (B) and formula (XIV), including any details and preferred embodiments of these or specific moieties thereof, are as for the first, second and fifth aspect of the invention.

Synthesis of Photoinitiator Monomers of General Formulas (I) and (II)

Monomeric quaternary ammonium photoinitiator monomers of the present invention according to general formula (I) can be readily synthesised by the following methods:

The first method comprises the steps of
a. providing a photoinitiator compound of general formula (IXa) containing a tertiary amine moiety:

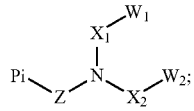
(IXa)

b. providing an alkylating agent of formula (Xa):

LG-R$^1$  (Xa); and c. reacting said photoinitiator compound (IXa) from step a. with the alkylating agent (Xa) from step b. such that the tertiary amine moiety of the photoinitiator compound becomes covalently linked to the group R$^1$ from the alkylating agent thus forming a quaternary ammonium salt of formula (I);

wherein in the formulas (IXa) and (Xa) Pi, Z, R$^1$, X$_1$, X$_2$, W$_1$, and W$_2$, are as defined for general formula (I) herein, and LG is a leaving group forming X$^-$ of formula (I).

The first method is typically a nitrogen alkylation reaction, carried out in polar solvents such as tetrahydrofuran, dioxane, dimethylformamide or alcohols such as methanol, ethanol or isopropylalcohol at temperatures typically ranging from 50° C. to 120° C. A detailed discussion of all aspects of this type of reaction can be found in a review by Abboud et al. (Progr. Phys. Org. Chem. 19, 1 (1993)).

The second method comprises the steps of:
a. providing a photoinitiator compound of general formula (Xb) containing a leaving group:

Pi-Z-LG  (Xb);

b. providing a tertiary amine of general formula (IXb):

(IXb)

and c. reacting said photoinitiator compound (Xb) from step a. with the tertiary amine (IXb) from step b. such that the tertiary amine moiety of (IXb) displaces the leaving group in the photoinitiator compound (Xb) thus forming a quaternary ammonium salt of formula (I);

wherein in the formulas (Xb) and (IXb) Pi, Z, R$^1$, X$_1$, X$_2$, W$_1$, and W$_2$, are as defined for general formula (I) herein, and LG is a leaving group forming X$^-$ of formula (I).

The second method is typically a nitrogen alkylation reaction, carried out in polar solvents such as tetrahydrofuran, dioxane, dimethylformamide or alcohols such as methanol, ethanol or isopropylalcohol at temperatures typically ranging from 50° C. to 120° C. A detailed discussion of all aspects of this type of reaction can be found in a review by Abboud et al. (Progr. Phys. Org. Chem. 19, 1 (1993)).

The third method comprises the steps of
a. providing a photoinitiator compound of general formula (IXc) containing a secondary amine moiety:

Pi-Z—NH—R$^1$  (IXc);

b. providing two alkylating agents, which may be the same or different, of general formulas (Xc) and (Xd):

LG-X$_1$—W$_1$  (Xc)

and

LG-X$_2$—W$_2$  (Xd); and c. reacting said photoinitiator compound (IXc) from step a. with both alkylating agents from step b. either simultaneously or consecutively such that both groups —X$_1$—W$_1$ and —X$_2$—W$_2$ of the two alkylating agents become covalently linked to the secondary amine moiety in the photoinitiator compound thus forming a quaternary ammonium salt of formula (I);

wherein in the formulas (IXc), (Xc), and (Xd), Pi, Z, R$^1$, X$_1$, X$_2$, W$_1$, and W$_2$, are as defined for general formula (I) herein, and LG is a leaving group, forming X$^-$ of formula (I).

The third method is typically a nitrogen alkylation reaction. This reaction is typically carried out in polar solvents such as tetrahydrofuran, dioxane, dimethylformamide or alcohols such as methanol, ethanol or isopropylalcohol at temperatures typically ranging from 50° C. to 120° C. A discussion of nitrogen alkylation reactions can be found in M. B. Smith, J. March; March's Advanced Organic Chemistry: Reactions, Mechanisms, and Structure, Sixth Edition, John Wiley & Sons 2007, ISBN 10: 0-471-72091-7, Chapter 10, Section 10-31.

The fourth method is for preparing photoinitiator monomers of formula (II) comprising the steps of:

a. providing a photoinitiator compound of general formula (IXd) containing a reactive group $RG_1$:

Pi-Za-$RG_1$ (IXd);

b. providing a quaternary ammonium salt of general formula (Xe) containing a reactive group $RG_2$:

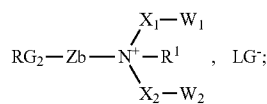

The fourth method is typically a nitrogen or oxygen acylation reaction. These reactions may typically be carried out in solvents such as tetrahydrofuran, dioxane, toluene or dichloromethane at temperatures typically ranging from 0° C. to 80° C. Reaction in which one of the groups $RG_1$ or $RG_2$ is a —COOH or —COOR$^2$ are typically carried out in the presence of an acid catalyst such as sulfuric acid or p-toluenesulfonic acid. Reaction in which one of the groups $RG_1$ or $RG_2$ is a —COCl is typically carried out in the presence of a tertiary amine base such as triethylamine. A collection of methods for the formation of ester can be found, for example, in J. Otera; Esterification Methods, Reactions, and Applications; Wiley-VCH Verlag 2003, ISBN 3-527-30490-8. Suitable nitrogen acylation methods can be found in M. B. Smith, J. March; March's Advanced Organic Chemistry: Reactions, Mechanisms, and Structure, Sixth Edition, John Wiley & Sons 2007, ISBN 10: 0-471-72091-7, Chapter 16, Sections 16-72 and 16-73.

Synthetic methods one, two and three are shown in Scheme 3, and synthetic method four is shown in Scheme 4.

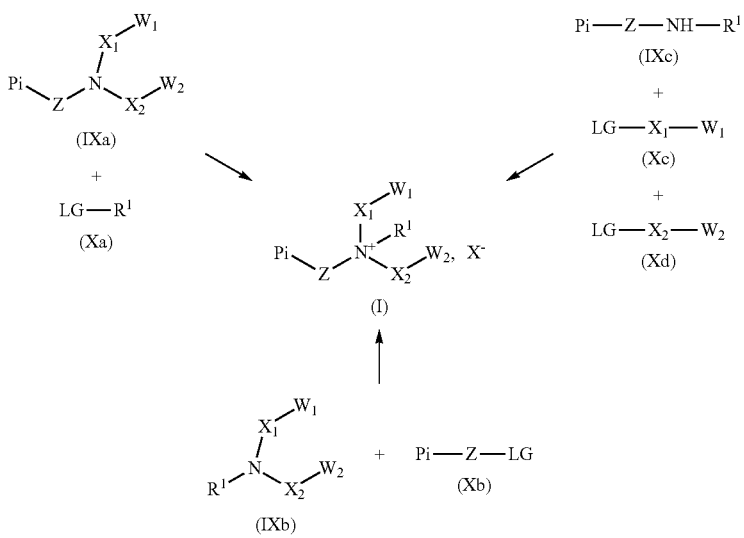

Scheme 3:

and c. reacting said photoinitiator compound (IXd) from step a. with the quaternary ammonium salt (Xe) from step b. such that the photoinitiator compound becomes covalently attached to the quaternary ammonium through a new chemical bond formed between reactive groups $RG_1$ and $RG_2$ thus forming a quaternary ammonium salt of formula (II);

wherein in the formulas (IXd) and (Xe) Pi, Za, Zb, $R^1$, $X_1$, $X_2$, $W_1$, and $W_2$, are as defined for formula (II) herein, LG is a leaving group, corresponding to $X^-$ of formula (II).

$RG_1$ denotes a reactive group which for example may be —OH, —NH$_2$, —NHR$^2$, —SH, —COOH, COOR$^2$ and —COCl. $RG_2$ denotes a reactive group selected from the same groups as $RG_1$, so as to be complementary to these. For example, if $RG_1$ is selected as —OH, —NH$_2$, —NHR$^2$, $RG_2$ is selected from —COOH, —COOR$^2$ and —COCl.

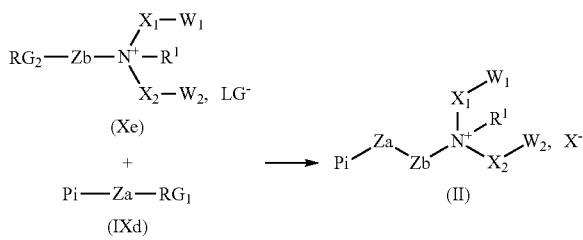

Scheme 4

Preparation of Polymeric Photoinitiators

The photoinitiator monomers of general formula (I) can be used directly as a monomer in a polymerization of e.g. polyurethane polymers. To carry this out, the photoinitiator monomers are mixed with one or more suitable monomers, such as monomer (B) and (C), optionally with further catalyst. Cationic self-crosslinkable polymers of the present invention can be synthesised as described in the following.

Polyurethanes, polythiourethanes and polydithiourethanes are typically prepared from their respective monomers in solvents or in bulk. For solvent-based procedures, the typical solvents include tetrahydrofuran, toluene and chlorobenzene at temperatures ranging from 20° C. to 100° C. Catalysts such as dibutyltin dilaurate (DBTDL) or 1,4-diazabicyclo[2.2.2]octane (DABCO) may be used to accelerate the reactions. Under bulk conditions, all components are reacted without solvent as a homogeneous reaction melt at temperatures typically between 50° C. to 120° C. Polyureas and polythioureas are typically prepared by analogous solvent-based or bulk procedures, but no catalyst is required since the polymerisation is typically very rapid at temperatures ranging from 20° C. to 100° C.

Polyurethane formation in the absence of a transition metal compound or a tertiary amine can be 10-500 times slower compared to the same reaction in the presence of a catalyst. The reaction times/reaction temperature can be increased accordingly to achieve the same degree of polymerisation. For general reference to polyurethane formation, see, for example, Encyclopedia of Polymer Science and Technology, John Wiley & Sons, Volume 4, p. 26.

Polyesters are typically prepared from their respective monomers in solvents such as toluene or xylenes in the presence of strong acid catalysts and with azeotropic removal of water or low molecular weight aliphatic alcohol by-product. Typical temperatures range from 80° C. to 150° C.

Polycarbonates are typically prepared in a solvent such as dichloromethane using a tertiary amine catalyst, while maintaining pH via the addition of NaOH. A melt transesterification process can also be used, which simply involves base-catalyzed reaction of a diol with diphenyl carbonate.

Polyphosphonites, polyphosphonates and polyphosphates are typically prepared from the appropriate phosphorus-based reagents bearing —$PCl_2$, —$P(=O)Cl_2$ or —O—$P(=O)Cl_2$ function group, respectively, and a diol. The reactions can be conveniently carried out in aromatic solvents such as toluene at temperatures ranging from 0° C. to 80° C. in the presence of tertiary amines.

Scheme 5 is a general scheme for the formation of polymeric photoinitiators of the invention, using a photoinitiator monomer (A), having the subformula (II) of formula (I):

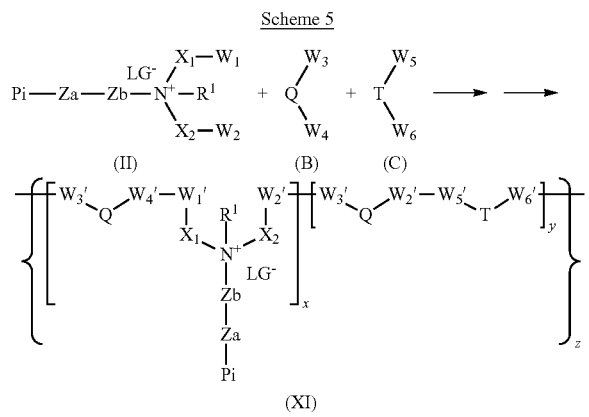

Scheme 5

In Scheme 5, formula (II), monomer (B) and (C), and preferred options thereof are as described herein above. Formula (XI) is an example of a polymeric photoinitiator of the invention formed by co-polymerization of photoinitiator monomers of formula (I). $LG^-$ represents a counterion, corresponding to $X^-$ as otherwise herein described in relation to formula (I) and subformulas thereof. Formulae (II) and (XI) have been exemplified with ZaZb, no limitation is hereby intended, the method applies for Z as well.

This method provides cationic self-crosslinkable polymers, where all photoinitiator monomer units carry a quaternary ammonium moiety. As set out above, the photoinitiator monomers of the present invention are incorporated into the polymer chain, as the end groups $W_1$, $W_2$, $W_5$ and $W_6$ react with the end groups $W_3$, $W_4$ of other monomers. The nomenclature $W_1'$, $W_2'$, $W_3'$, $W_4'$, $W_5'$ and $W_6'$ depict the corresponding end groups $W_1$-$W_6$ after being reacted. In formula (XI) immediately herein above, x, y, z represent the repetitions of the monomers. Pi, Z, Za, Zb, $X^-$ (represented by $LG^-$ in this specific case), $X_1$, $X_2$, $W_1$, and $W_2$, and preferred option of these, are as defined for general formula (I) herein.

The photoinitiator moiety becomes pendant from the polymer backbone. As such, it is not able to leach from the polymer matrix. In addition, radical bond-forming reactions between the photoinitiator moiety and other components of the polymerization mixture will cause cross-linking, rather than forming undesirable low molecular weight compounds.

End groups $W_3$ and $W_4$ are independently selected from the same end groups as $W_1$ and $W_2$. $W_3$ and $W_4$ are selected so as to be complementary to $W_1$ and $W_2$. For instance, if the end groups $W_1$, $W_2$ comprise alcohol, amine or thiol groups, suitable $W_3$ and $W_4$ will comprise isocyanate or isothiocyanate groups, and vice-versa, so that a polyurethane or a polyurethane like chain is formed. When for example a polyurethane is to be formed $W_1$, $W_2$ may comprise alcohol and $W_3$ and $W_4$ may comprise isocyanate.

Additional monomers may be introduced into the polyurethane according to the above scheme, as desired by the person skilled in the art. The additional monomers may be other monomers (A) having the structure of photoinitiator monomers of Formula I, or other monomers.

The weight of the photoinitiator monomer (I) used to prepare a suitable cationic self-crosslinkable polymer, i.e. a polymeric photoinitiator, of the invention may be between 0.1% and 99% of the total mass of other monomers, suitably between 0.2% and 10%, most suitably 0.5% to 5%. Suitably, the polymeric photoinitiator has a molecular weight of more than 1 kDa, suitably between 10 kDa and 1000 kDa, most suitably between 20 kDa and 100 kDa.

In addition, polyurethane films comprising the photoinitiator monomers of the present invention exhibit good adhesion in film form to polar surfaces, such as aromatic polyurethanes, polyesters and PVC.

Schemes 4 and 5 are general schemes for the formation of polymeric quaternary ammonium photoinitiators of the invention. Scheme 6 depicts the use of a photoinitiator monomer (A') having formula (I'), where linker Z is a linker ZaZb:

Scheme 6:

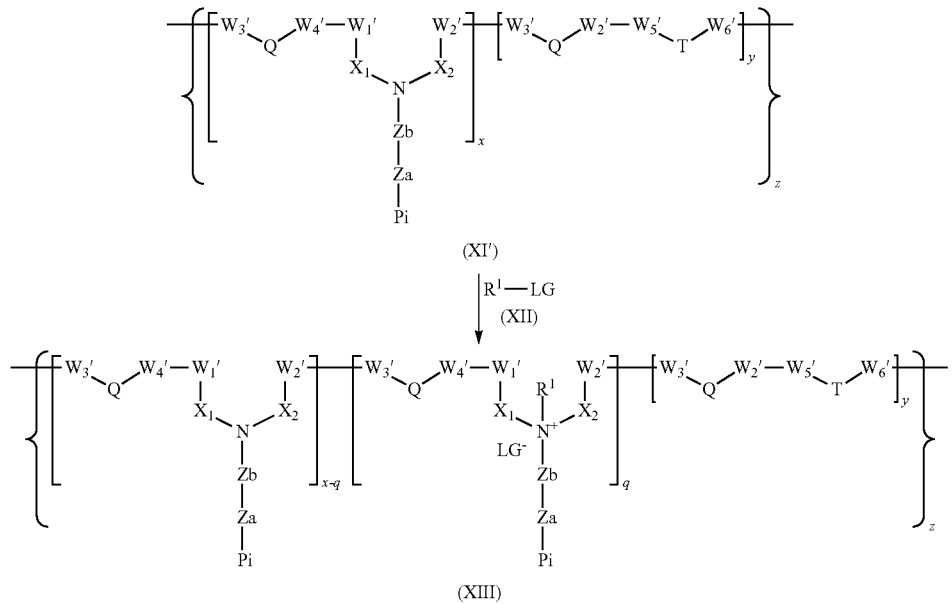

(XI')

In Scheme 6, formula (XII) represents alkylating agent $R^1$-LG and preferred options thereof are as described herein above. Formula (XI') is an example of a polymeric photoinitiator formed by co-polymerization of photoinitiator monomer (A') having formula (I') and monomers (B) and (C) as described herein above. Formulas (XI') and (XIII) have been exemplified with ZaZb, no limitation is hereby intended, the method is applies for Z as well.

Scheme 7 depicts the use of a photoinitiator monomer (A") having formula (I"), and an alkylating agent comprising a photoinitiator moiety (XIV), where linker Z is a linker ZaZb:

herein above. Formula (XI") is an example of a polymer formed by co-polymerization of monomer (A") and monomers (B) and (C) as described herein above. Formulas (XIV) and (XIII) have been exemplified with ZaZb, no limitation is hereby intended, the method applies for Z as well.

This method provides cationic self-crosslinkable polymers, where some or all photoinitiator monomer units carry a quaternary ammonium moiety. As set out above, the photoinitiator monomers of the present invention are incorporated into the polymer chain, as the end groups $W_1$, $W_2$, $W_5$ and $W_6$ react with the end groups $W_3$, $W_4$ of other monomers. The nomenclature $W_1'$, $W_2'$, $W_3'$, $W_4'$, $W_5'$ and Scheme 7:

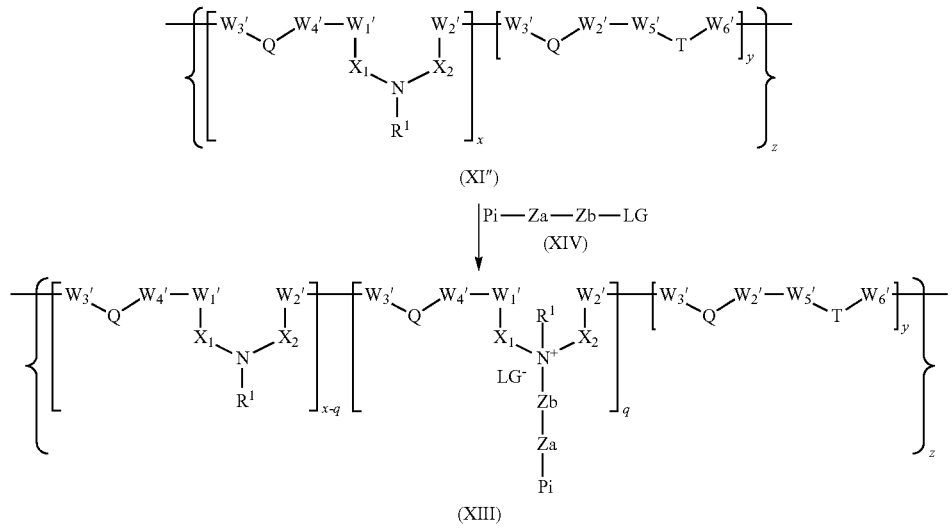

In Scheme 7, formula (XIV) represents alkylating agent Pi-Za-Zb-LG and preferred options thereof are as described $W_6'$ depict the corresponding end groups $W_1$-$W_6$ after being reacted. In formula (XIII) herein above, x, y, z, q and x-q represent the repetitions of the monomers. Assuming quantitative conversion, the ratio of alkylating agent (XII) or (XIV) to tertiary amine moieties in polymer (XI') or (XI") is equal to q:x.

Pi, Z, Za, Zb, $X^-$ (represented by $LG^-$ in this specific case), $X_1$, $X_2$, $W_1$, and $W_2$, and preferred option of these, are as defined for general formula (I) herein.

EXPERIMENTAL SECTION

Preparatory Examples of Photoinitiator Monomers of Formula (I') and Intermediates (IXa)

Preparatory Example 1: 4-{3-[bis(2-hydroxyethyl)amino]propoxy}benzophenone

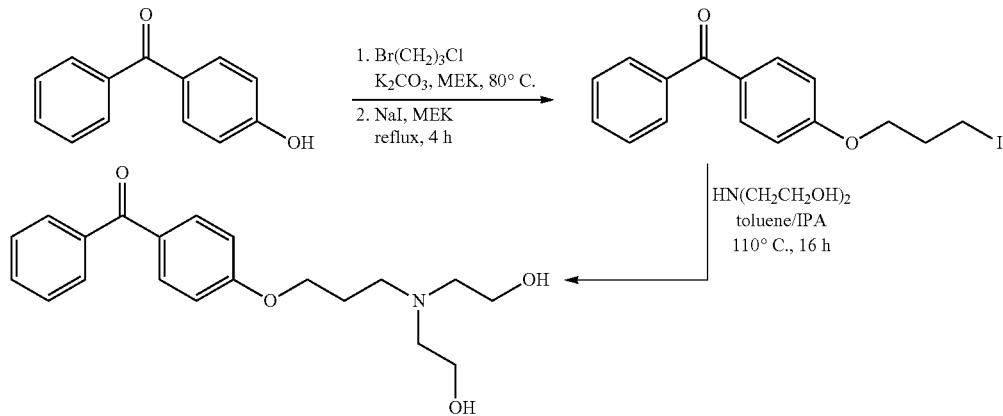

Relevant Literature

J. Med. Chem. 2001, 3810-3820; J. Med. Chem. 1998, 3976-3986; J. Med. Chem. 1989, 105-118.

Small Scale:

A 1000 mL three-neck flask was charged with 4-hydroxybenzophenone (50.00 g; 252.2 mmol), 1-bromo-3-chloropropane (79.41 g; 504.4 mmol) and 2-butanone (500 mL). After flushing with nitrogen, anhydrous potassium carbonate (104.6 g; 756.5 mmol) was added and the reaction mixture was stirred at reflux for 24 h. Full consumption of the starting 4-hydroxybenzophenone was confirmed by TLC. The reaction mixture was filtered, the filtrate evaporated, the oily residue dissolved in dichloromethane (300 mL) and extracted with water (3×100 mL). The organic phase was separated, evaporated, and the unreacted 1-bromo-3-chloropropane was removed by heating to 70° C. in vacuo. The residue was dissolved in 2-butanone (500 mL) and sodium iodide (45.36 g; 302.6 mmol) was added. The reaction mixture was refluxed for 6 h. The reaction mixture was filtered, the filtrate evaporated, the oily residue dissolved in dichloromethane (300 mL) and extracted with water (3×100 mL). The organic phase was separated, evaporated, the light brown oily residue dried in vacuo to give crude 4-(3-iodopropoxy)benzophenone (light brown solid; 83.2 g).

To the crude product from the previous step (83.2 g; 227.2 mmol) was added toluene (100 mL), 2-propanol (200 mL) and diethanolamine (179.2 g; 1.704 mol). The reaction mixture was refluxed (110° C.) for 16 h. After evaporation of ethanol and toluene, water (2000 mL) was added to precipitate the oily product. The emulsion obtained was thoroughly extracted with diethyl ether (6×300 mL). The aqueous phase was discarded and the organic phase was extracted with hydrochloric acid (6M, 3×200 mL). The pH of the strongly acidic aqueous phase was adjusted to 12-13 by slow addition of 35% aq. ammonia to reprecipitate the product. The aqueous phase was reextracted with dichloromethane (3×300 mL), the organic phase dried (MgSO$_4$), evaporated and the light brown oily product dried in vacuo. This provides 4-{3-[bis(2-hydroxyethyl)amino]propoxy}benzophenone (57.7 g; 74% yield).

$^1$H-NMR (400 MHz, chloroform-d): 7.80 (d, J=8.8 Hz, 2H), 7.73 (d, J=8.3 Hz, 2H), 7.55 (m, 1H), 7.46 (t, J=7.8 Hz, 2H), 6.95 (d, J=8.8 Hz, 2H), 4.12 (t, J=6.0 Hz, 2H), 3.62 (t, J=5.3 Hz, 4H), 2.87 (bs, 2H), 2.75 (t, J=6.9 Hz, 2H), 2.67 (t, J=5.3 Hz, 4H), 1.96 (apparent quintet, J=6.4 Hz, 2H). UV (MeCN): $\lambda_{max}$=286 nm.

Large Scale:

A 5000 mL three-neck flask was charged with 4-hydroxybenzophenone (800.0 g; 4.036 mol), 1-bromo-3-chloropropane (832.5 g; 5.288 mol) and 2-butanone (3300 mL). Anhydrous potassium carbonate (673.6 g; 4.874 mol) was added and the reaction mixture was stirred at reflux for 100 h. Full consumption of the starting 4-hydroxybenzophenone was confirmed by HPLC. The reaction mixture was filtered, the inorganic solids were washed with 2-butanone (3×100 mL). The filtrate was evaporated, and the unreacted 1-bromo-3-chloropropane was removed by heating to 70° C. in vacuo. The residue was dissolved in acetonitrile (2000 mL) and sodium iodide (650.0 g; 4.337 mol) was added. The reaction mixture was refluxed for 8 h. The reaction mixture was filtered to give a solution of crude 4-(3-iodopropoxy)benzophenone.

The crude acetonitrile solution from the previous stage was charged over a period of 6 hours into neat diethanolamine (2800 g; 26.63 mol) heated to 70° C. After the end of the feed, the reaction mixture heated to reflux for a further 2 h. Full consumption of the starting material was confirmed by TLC. The reaction mixture was poured into water (10 L) and the resulting suspension extracted with dichloromethane (3×1500 mL). The organic phase was separated and extracted with 1 M aq. HCl (4000 mL). The organic phase was discarded and the aqueous phase was made strongly alkaline (pH 12) by slow addition of 50% aq. NaOH. The resulting suspension was extracted with dichloromethane (3×1000 mL). The organic layer was dried (MgSO$_4$), filtered and evaporated. The light brown oil was dried in high vacuo at 80° C. This provides 4-{3-[bis(2-hydroxyethyl)amino]propoxy}benzophenone (1180 g; 85.1% yield over 3 steps).

Alternative Procedure:

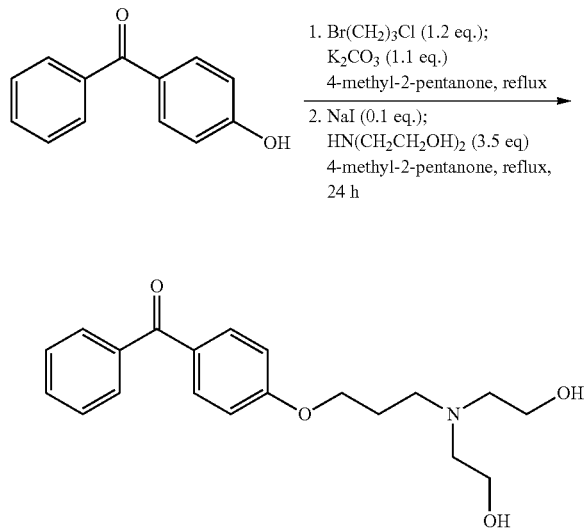

A 500 mL three-neck flask was charged with 4-hydroxybenzophenone (80.00 g; 0.4036 mol), 1-bromo-3-chloropropane (76.25 g; 0.4843 mol) and 4-methyl-2-pentanone (330 mL).

Anhydrous potassium carbonate (61.36 g; 0.4440 mol) was added and the reaction mixture was stirred at reflux (120° C.) for 4 h. HPLC analysis shows that the reaction mixture contains 90.0% 4-(3-chloropropoxy)benzophenone; 7.0% 1,3-bis(4-benzoylphenoxy)propane and 0.8% 4-hydroxybenzophenone. The reaction mixture was filtered hot and the inorganic solids were washed with 4-methyl-2-pentanone (100 mL). The filtrate was charged into a mixture of diethanolamine (148.5 g; 1.412 mol), sodium iodide (6.05 g; 0.0404 mol) and 4-methyl-2-pentanone (150 mL). The reaction mixture heated to reflux (122° C.) for 24 h. The reaction mixture was cooled to room temperature and extracted with water (500 mL). The organic phase was extracted with 1 M HCl (500 mL) at 70° C. to prevent crystallisation of the 1,3-bis(4-benzoylphenoxy)propane byproduct. The aqueous phase was separated, cooled to room temperature and taken to pH 12 with 50% aqueous NaOH. The resulting emulsion was extracted with 4-methyl-2-pentanone (3×200 mL). The organic phase was separated, dried (MgSO₄), filtered and the solvent removed in vacuo. This provides 4-{3-[bis(2-hydroxyethyl)amino]propoxy}benzophenone (123.2 g; 89% yield over 3 steps).

Preparatory Example 2: 4-{3-[bis(2-hydroxyethyl)amino]propoxy}-1-chloro-9H-thioxanthen-9-one

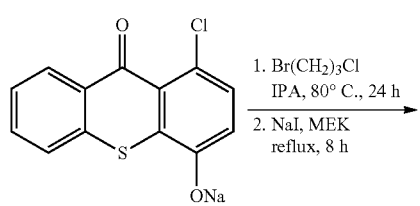

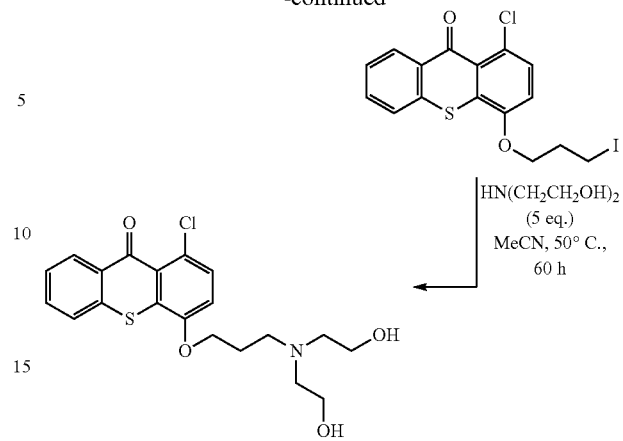

Small Scale:
A 500 mL flask was charged with the sodium salt of 1-chloro-4-hydroxy-9H-thioxanthen-9-one (28.5 g; 0.100 mol), 1-bromo-3-chloropropane (17.4 g; 0.111 mol) and isopropyl alcohol (280 mL). The turbid reaction mixture was refluxed for 24 h. The hot solution was diluted with isopropyl alcohol (130 mL), drowned out in water (1400 mL) and the resulting suspension was extracted with dichloromethane (3×250 mL). The organic phase was separated, dried (MgSO₄), filtered and solvent removed in vacuo to give 1-chloro-4-(3-chloropropoxy)-9H-thioxanthen-9-one (24.4 g; 72% yield).

$^1$H-NMR (400 MHz, CDCl$_3$): 8.39 (ddd, J=8.1, 1.5, 0.6 Hz, 1H), 7.54 (m, 1H), 7.48 (ddd, J=8.1, 1.4, 0.6 Hz), 7.41 (m, 1H), 7.33 (d, J=8.6 Hz, 1H), 6.92 (d, J=8.6 Hz, 1H), 4.23 (t, J=5.8 Hz, 2H), 3.83 (t, J=6.3 Hz, 2H), 2.32 (apparent quintet, J=6.0 Hz, 2H).

The crude product from the previous step (26.44 g; 77.94 mmol) was suspended in 2-butanone (250 mL) and sodium iodide (14.02 g; 93.52 mmol) was added. The reaction mixture was refluxed for 16 h. The reaction mixture was filtered, the solids were washed with boiling 2-butanone (2×50 mL), the filtrate evaporated, the oily residue dissolved in dichloromethane (300 mL) and extracted with water (2×100 mL). The organic phase was separated, evaporated and dried in vacuo to give crude 1-chloro-4-(3-iodopropoxy)-9H-thioxanthen-9-one (30.51 g; yellow solid; 91% yield).

$^1$H-NMR (400 MHz, CDCl$_3$): 8.53 (dd, J=9.0, 1.4 Hz, 1H), 7.59 (m, 1H), 7.53 (dd, J=8.9, 1.5 Hz, 1H), 7.45 (m, 1H), 7.37 (d, J=9.6 Hz, 1H), 6.91 (d, J=9.6 Hz, 1H), 3.83 (t, J=6.3 Hz, 2H), 3.03 (t, J=7.4 Hz, 2H), 1.81 (apparent quintet, J=6.9 Hz, 2H).

Crude 1-chloro-4-(3-iodopropoxy)-9H-thioxanthen-9-one (10.0 g; 23.22 mmol) from the previous step was slowly charged into a solution of diethanolamine (14.65 g; 139.3 mmol) in acetonitrile (100 mL) heated to 50° C. The reaction mixture was stirred vigorously and heated to 50° C. for 60 h. The solvent was removed in vacuo and water (500 mL) was added. The mixture was extracted with dichloromethane (3×250 mL). The aqueous phase was discarded and the organic phase was extracted with hydrochloric acid (2M, 3×100 mL). The pH of the strongly acidic aqueous phase was adjusted to 12-13 by slow addition of 50% aq. NaOH to reprecipitate the product. The aqueous phase was reextracted with dichloromethane (4×100 mL), the organic phase dried (MgSO$_4$), evaporated to give 4-{3-[bis(2-hydroxyethyl)amino]propoxy}-1-chloro-9H-thioxanthen-9-one (5.31 g; 56% yield).

$^1$H-NMR (400 MHz, CDCl$_3$): 8.29 (ddd, J=8.1, 1.5, 0.6 Hz, 1H), 7.45 (ddd, J=8.2, 6.8, 1.4 Hz, 1H), 7.39 (ddd, J=8.1, 1.4, 0.6 Hz, 1H), 7.34 (ddd, J=8.2, 6.8, 1.4 Hz, 1H), 7.21 (d, J=8.6 Hz, 1H), 6.81 (d, J=8.6 Hz, 1H), 4.04 (t, J=6.1 Hz, 2H), 3.64 (bs, 2H), 3.59 (t, J=5.2 Hz, 4H), 2.73 (t, J=6.8 Hz, 2H), 2.63 (t, J=5.2 Hz, 4H), 1.94 (apparent quintet, J=6.4 Hz, 2H).

Large Scale Prep:

A 1000 mL three-neck flask was charged with 1-chloro-4-hydroxy-9H-thioxanthen-9-one (100.0 g; 0.381 mol), 1-bromo-3-chloropropane (71.9 g; 0.457 mol), anhydrous potassium carbonate (63.1 g; 0.457 mol) and 2-butanone (500 mL). The mixture was stirred at reflux for 60 h. Full conversion was confirmed by TLC. The reaction mixture was filtered through a glass sinter, the inorganic solids were washed with warm dichloromethane (4×100 mL). The filtrate was evaporated to dryness to give a bright yellow solid. The crude 1-chloro-4-(3-chloropropoxy)-9H-thioxanthen-9-one (129.1 g) was dissolved in 2-butanone (400 mL) and sodium iodide (62.8 g; 0.419 mol) was added. The reaction mixture was refluxed for 16 h, filtered hot, the solids were washed with boiling 2-butanone (2×100 mL) and the filtrate evaporated to dryness.

The crude product from the previous step was suspended in THF (300 mL) and the suspension was charged over 30 min to neat diethanolamine (240.1 g; 2.28 mol) at 60° C. The reaction was heated to reflux for 3 h. The clear yellow-brown solution was poured into water (2000 mL) and extracted with ethyl acetate (3×750 mL). The aqueous phase was discarded and the organic phase was extracted with hydrochloric acid (1M, 3×500 mL). The pH of the strongly acidic aqueous phase was adjusted to 12-13 by slow addition of 50% aq. NaOH to reprecipitate the product. The aqueous phase was reextracted with dichloromethane (4×500 mL), the organic phase dried (MgSO$_4$) and evaporated to dryness to give 4-{3-[bis(2-hydroxyethyl)amino]propoxy}-1-chloro-9H-thioxanthen-9-one (99.8 g; 64% yield).

Preparatory Example 3: {4-[bis(2-hydroxyethyl)amino]phenyl}(phenyl)methanone

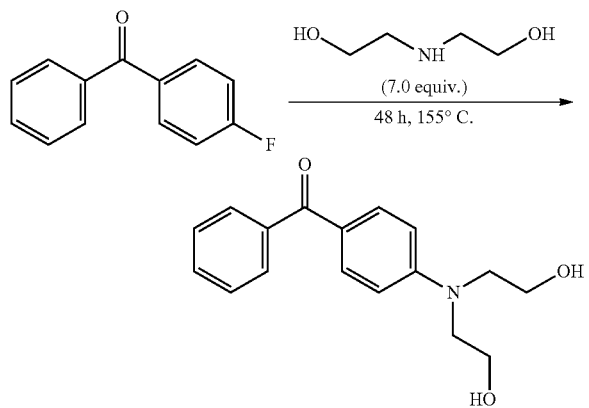

Relevant Literature

*J. Phys. Org. Chem.* 2001, 14, 247-255; *J. Med. Chem.* 1991, 34, 1552-1560.

A 100 mL two-neck flask was charged with 4-fluorobenzophenone (15.0 g; 74.9 mmol) and diethanolamine (55.1 g; 524 mmol). The flask was flushed with nitrogen, fitted with a reflux condenser and heated to 155° C. for 48 h under a gentle stream of nitrogen. Complete conversion of the starting 4-fluorobenzophenone was confirmed by TLC. After cooling to ambient temperature, the dark viscous reaction mixture was poured into water (2000 mL). The resulting suspension was thoroughly extracted with diethyl ether (6×250 mL). The aqueous phase was discarded and the organic phase was extracted with hydrochloric acid (2M, 5×200 mL). The pH of the strongly acidic aqueous phase was adjusted to 12-13 by slow addition of 35% aq. ammonia to reprecipitate the product. The aqueous phase was then reextracted with dichloromethane (3×300 mL). The crude organic extract was purified by passing through a short silica gel column (eluent: ethyl acetate). The eluted yellow solution was evaporated and the oily residue dried in vacuo to provide {4-[bis(2-hydroxyethyl)amino]phenyl}(phenyl)methanone (yellow-brown solid; 13.176 g; 62% yield).

$^1$H-NMR (400 MHz, CDCl$_3$): 7.72 (d, J=10.0 Hz, 2H), 7.69-7.66 (m, 2H), 7.53 (tt, J=8.2, 1.4 Hz, 1H), 7.42 (t, J=8.3 Hz, 2H), 6.55 (d, J=10.0 Hz, 2H), 4.22 (bs, 2H), 3.43 (t, J=5.4 Hz, 4H), 3.20 (t, J=5.4 Hz, 4H).

$^{13}$C-NMR (100 MHz, CDCl$_3$): 195.5, 151.5, 138.7, 132.8, 131.4, 129.4, 128.0, 124.8, 111.0, 60.1, 54.9.

Preparatory Example 4: 4-{[bis(2-hydroxyethyl)amino]methyl}benzophenone

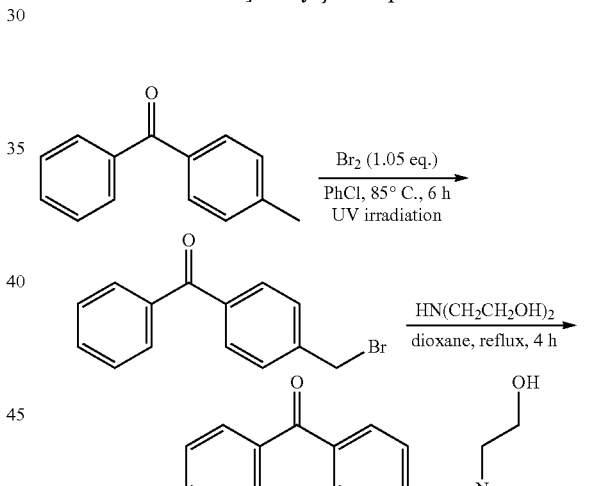

Relevant Literature

Tetrahedron 2009, 4429-4439.

A 5000 mL three-neck flask was charged with 4-methylbenzophenone (1100 g; 5.605 mol). The starting material was dissolved in chlorobenzene (2500 mL) and the reaction mixture warmed to 75° C. A solution of bromine (302 mL; 5.886 mol) in chlorobenzene (500 mL) was added to the reaction vessel in 100 mL portions over 6 hours. The reaction temperature was maintained at 85° C. and the reaction vessel was irradiated with a 240 W incandescent bulb. Hydrogen bromide gas evolved during the reaction was neutralised with an aqueous KOH scrubber system. After complete disappearance of orange coloration, the reaction mixture was cooled to ambient temperature and all volatiles removed in vacuo. The residue was dried under oil pump vacuum for 4 h at 60° C. Pale yellow-orange solid was obtained upon cooling (1500 g). 1H-NMR indicates that the crude product contains 20% 4-methylbenzophenone, 71% 4-(bromomethyl)benzophenone and 9% 4-(dibromomethyl) benzophenone. The crude product was used directly in the next step.

A 10000 mL three-neck flask was charged with diethanolamine (4400 g; 41.85 mol). After warming to 90° C., a slurry of crude material from the previous step (1500 g) in dioxane (2000 mL) was added to the oily reaction mixture in 6 portions over a period of 2 hours. After the addition was complete, the reaction was taken to gentle reflux (100° C.) and heated for a further 2 hours. Complete conversion of 4-(bromomethyl)benzophenone was confirmed by TLC. Dioxane was removed from the reaction by evaporation under reduced pressure. The oily orange residue was poured into water (20 L) and extracted with ethyl acetate (3×1500 mL). The aqueous phase was discarded and the organic phase was extracted with hydrochloric acid (1.2M, 3×1000 mL). The pH of the strongly acidic aqueous phase was adjusted to 12-13 by slow addition of 50% aq. NaOH to reprecipitate the product. Most of the product separated out as an orange oil. The residual aqueous phase was reextracted with dichloromethane (3×500 mL), combined organic phases were dried (Na$_2$SO$_4$), volatiles were evaporated under reduced pressure and the light brown oily product dried under oil pump vacuum (6 h, 60° C.).

This provides 4-{[bis(2-hydroxyethyl)amino] methyl}benzophenone (1170 g; 70.0% yield over 2 steps).

$^1$H-NMR (400 MHz, chloroform-d): 7.80-7.75 (m, 4H), 7.58 (tt, J=7.4, 1.4 Hz, 1H), 7.50-7.44 (m, 4H), 3.79 (s, 2H), 3.65 (t, J=5.4 Hz, 4H), 2.74 (t, J=5.4 Hz, 4H), 2.59 (bs, 2H). UV (MeCN): $\lambda_{max}$=255 nm.

Preparatory Example 5: (2-{3-[bis(2-hydroxyethyl) amino]propoxy}-4-methoxyphenyl)(phenyl)methanone

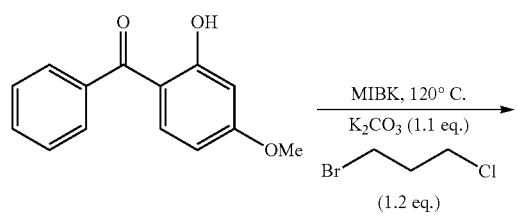

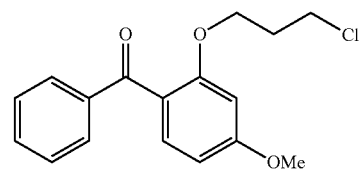

crude MIBK filtrate carried straight through
NaI (0.1 eq.), HN(CH$_2$CH$_2$OH)$_2$ (3.5 eq.),
MIBK, reflux -continued

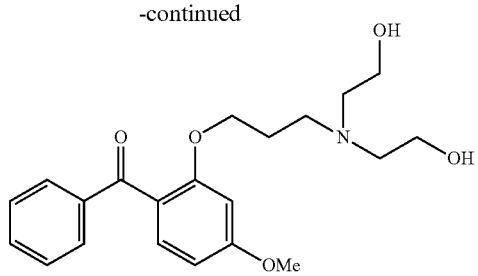

Large Scale Prep:

A 500 mL three-neck flask was charged with (2-hydroxy-4-methoxyphenyl)(phenyl) methanone (100.0 g; 0.4381 mol), 1-bromo-3-chloropropane (82.78 g; 0.5258 mol) and 4-methyl-2-pentanone (250 mL). Anhydrous potassium carbonate (66.61 g; 0.4819 mol) was added and the reaction mixture was stirred at reflux (120° C.) for 10 h. The reaction mixture was filtered hot and the inorganic solids were washed with 4-methyl-2-pentanone (2×100 mL). The filtrate was charged into a mixture of neat diethanolamine (161.2 g; 1.533 mol) and sodium iodide (6.57 g; 43.81 mmol). The reaction mixture heated to reflux (122° C.) for 24 h. The reaction mixture was cooled to room temperature and diluted with water (500 mL). The resulting emulsion was extracted with 4-methyl-2-pentanone (2×200 mL). The aqueous phase was discarded and the organic phase was extracted with 1 M HCl (2×500 mL). The aqueous phase was taken to pH 12 with 50% aqueous NaOH. The resulting emulsion was extracted with 4-methyl-2-pentanone (3×200 mL). The organic phase was separated, dried (MgSO$_4$), filtered and the solvent removed in vacuo. This provides (2-{3-[bis(2-hydroxyethyl)amino]propoxy}-4-methoxyphenyl)(phenyl)methanone (light yellow oil; 90.4 g; 55% yield over 3 steps).

$^1$H-NMR (400 MHz, CDCl$_3$): 7.68-7.66 (m, 2H), 7.44 (tt, J=7.4, 1.4 Hz, 1H), 7.37 (d, J=8.4 Hz, 1H), 7.35-7.32 (m, 2H), 6.48 (dd, J=8.5, 2.3 Hz, 1H), 6.42 (d, J=2.3 Hz, 1H), 3.83 (t, J=5.8 Hz, 2H), 3.77 (s, 3H), 3.57 (bs, 2H), 3.39 (t, J=5.3 Hz, 4H), 2.37 (t, J=5.3 Hz, 4H), 2.18 (t, J=7.1 Hz, 2H), 1.49 (apparent quintet, J=6.5 Hz, 2H).

Preparatory Examples for the Preparation of Intermediate Polymeric Photoinitiators from Photoinitiator Monomers of Formula (I')

Preparatory Example 6: General Procedure for Preparation of Polyurethanes in Solvent A glass vial was charged with a reactive photoinitiator monomer ((PI), Preparatory examples and a reactive polyether (amounts given in Table 1)). The reaction vessel was heated to 120-130° C. under vacuum for 1 h to remove all moisture. The reaction vessel was then allowed to cool under vacuum, fitted with a reflux condenser and flushed with nitrogen. Dry chlorobenzene was added and the reaction was stirred at 60° C. to obtain a homogeneous clear solution with 30 wt % of solids. Appropriate amount of diisocyanate was added via syringe and the reaction mixture was heated under reflux for 16 h. The viscous yellow mixture was evaporated in vacuo, residual chlorobenzene was removed by co-evaporation with MeOH-water. The resulting gummy solid was dried in vacuo for 4-6 h at 75° C. This provided the appropriate polyurethane polymer as a light yellow-brown gummy solid.

TABLE 1

Composition and GPC characterisation of photoinitiator polyurethanes
prepared by general procedure in Preparatory Example 6 in solvent

| Entry | PI (I'), Preparatory Example No.: | wt % | Reactive polyether | wt % | Diisocyanate | wt % | Polymer Mw | Mw/Mn |
|---|---|---|---|---|---|---|---|---|
| 1  | 1 | 2  | PEG-2000        | 85 | HMDI | 13 | 76 kDa | 1.92 |
| 2  | 1 | 10 | PEG-2000        | 73 | HMDI | 17 | 78 kDa | 2.27 |
| 3  | 1 | 2  | Jeffamine D-4000 | 91 | HMDI | 7  | 35 kDa | 2.19 |
| 4  | 2 | 2  | PEG-2000        | 85 | HMDI | 13 | 43 kDa | 1.76 |
| 5  | 2 | 10 | PEG-2000        | 74 | HMDI | 16 | 29 kDa | 1.62 |
| 6  | 2 | 2  | Jeffamine D-4000 | 91 | HMDI | 7  | 32 kDa | 2.06 |
| 7  | 3 | 2  | PEG-2000        | 85 | HMDI | 13 | 37 kDa | 1.87 |
| 8  | 3 | 10 | PEG-2000        | 71 | HMDI | 19 | 34 kDa | 1.77 |
| 9  | 3 | 2  | Jeffamine D-4000 | 90 | HMDI | 8  | 33 kDa | 2.09 |
| 10 | 4 | 2  | PEG-2000        | 85 | HMDI | 13 | 43 kDa | 2.37 |
| 11 | 4 | 10 | PEG-2000        | 72 | HMDI | 18 | 76 kDa | 2.12 |
| 12 | 4 | 2  | Jeffamine D-4000 | 90 | HMDI | 8  | 27 kDa | 1.75 |
| 13 | 1 | 57 | None            | 0  | HMDI | 43 | 56 kDa | 2.37 |

Preparatory Example 7: Solvent-Free Procedure for Preparation of Polyurethanes A glass vial was charged with a reactive photoinitiator monomer and a reactive polyether (amounts given in Table 2). The reaction vessel was heated to 120-130° C. under vacuum for 1 h to remove all moisture. The flask was allowed to cool to 70° C. and charged with the appropriate amount of diisocyanate (given in Table 2). The reaction melt was then heated with stirring to 70° C. for 16 h. This provided the appropriate photochromic polymer as a white to light yellow solid.

TABLE 2

Composition and GPC characterisation of photoinitiator
polyurethanes prepared by solvent solvent-free
procedure of Preparatory Example 7

| Entry | PI (I'), Preparatory Example No.: | wt % | Reactive polyether | wt % | Diisocyanate | wt % | Polymer Mw |
|---|---|---|---|---|---|---|---|
| 1 | 1 | 2 | PPG-2000 | 89 | HDI  | 9  | 50 kDa |
| 2 | 1 | 2 | PPG-4000 | 93 | HDI  | 5  | 45 kDa |
| 3 | 1 | 2 | PPG-2000 | 85 | HMDI | 13 | 24 kDa |
| 4 | 1 | 2 | PPG-4000 | 91 | HMDI | 7  | 21 kDa |
| 5 | 1 | 2 | PEG-2000 | 89 | HDI  | 9  | 53 kDa |
| 6 | 1 | 2 | PEG-4600 | 94 | HDI  | 4  | 62 kDa |
| 7 | 4 | 2 | PEG-2000 | 89 | HDI  | 9  | 54 kDa |
| 8 | 4 | 2 | PEG-4600 | 93 | HDI  | 5  | 50 kDa |

Preparatory Example 8: Polyurethane Photoinitiator Prepared in DMF Solvent

PEG 2000 (5.00 g; 2.50 mmol) was melted and heated to 90° C. for 2 hours under vacuum to remove residual moisture. The reaction mixture was cooled to ambient temperature and 4-{3-[bis(2-hydroxyethyl)amino]propoxy}benzophenone (1.9304 g; 5.62 mmol) and anhydrous DMF (10 mL) were added. The reaction mixture was fully homogenised by mixing at 60° C. and then hexamethylene diisocyanate (1.3659 g; 8.12 mmol) was added followed by dibutyltin dilaurate (0.01 g; 15.8 μmol). The reaction vial was sealed, the content was thoroughly mixed and the mixture was heated to 90° C. for 2.5 h. The highly viscous liquid reaction mass was dissolved in methanol (25 mL), transferred to a round bottom flask and all solvents were removed in vacuo at 90° C. to provide the product as a white tough elastic solid.

Example 1: [3-(4-benzoylphenoxy)propyl]bis(2-hydroxyethyl)methylammonium iodide

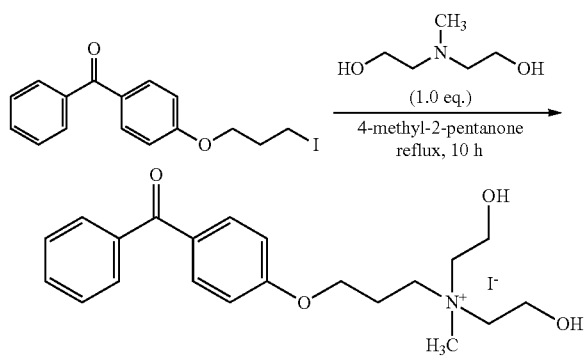

A two neck flask was charged with 4-(3-iodopropoxy)benzophenone (10.0 g; 27.3 mmol), N-methyldiethanolamine (3.25 g; 27.3 mmol) and 4-methyl-2-pentanone (100 mL). The reaction mixture was stirred vigorously and heated to reflux (118° C.) for 10 h. The solvent was evaporated and the residue was purified by chromatography on silica (eluent: methanol). This provided the desired [3-(4-benzoylphenoxy)propyl]bis(2-hydroxyethyl)methylammonium iodide as off-white solid (10.86 g; 82%). The product can be further repurified by crystallization from 2-butanone/isopropylalcohol.

$^1$H-NMR (400 MHz, DMSO-$d_6$): 7.75 (d, J=8.9 Hz, 2H), 7.69-7.63 (m, 3H), 7.55 (t, J=7.4 Hz, 2H), 7.10 (d, J=8.9 Hz, 2H), 5.27 (t, J=5.0 Hz, 2H), 4.17 (t, J=6.1 Hz, 2H), 3.87 (m, 4H), 3.62-3.58 (m, 2H), 3.53 (dd, J=6.7, 4.1 Hz, 4H), 3.16 (s, 3H), 2.25 (m, 2H).

$^{13}$C-NMR (100 MHz, DMSO-$d_6$): 194.3, 161.7, 137.5, 132.1, 132.0, 129.5, 129.1, 128.4, 114.3, 65.1, 63.3, 59.6, 54.7, 49.2, 22.0.

m.p. 97-99° C.

Example 2: Solvent-Free Procedure for the Preparation of Polyurethanes

A glass vial is charged with a reactive photoinitiator monomer of formula (I) and polyethylene glycol. The reaction vessel is heated to 120-130° C. under vacuum for 1 h to remove all moisture. The flask is allowed to cool to 70° C. and charged with the appropriate equimolar amount of diisocyanate. The reaction melt is then heated with stirring to 70° C. for 10 h. This provides the appropriate UV photocrosslinkable polyurethane polymer as a solid.

Example 3: UV Photocrosslinking of Polyurethanes

A polyurethane prepared in Example 2 is processed to a plate using a heat press. A disc is cut from this plate (Ø25 mm) and placed in a plate-plate rheometer, where the bottom plate consists of a quartz window. Rheological properties are measured at 1 Hz at 120° C., where a UV-light source irradiating the polyurethane sample through the quartz plate is turned on at t=0 s. After approximately 60 s the sample passes a transition from a liquid state to a solid state, i.e. a gel-point, which demonstrates that the photoinitiator moieties within the polyurethane are actually responsible for photocrosslinking the sample when exposed to UV light.

Example 4: UV Curing of Acrylics—Route to Polymerized n-Butyl Acrylate

A solution of 500 mg of a copolymer prepared in Example 2 in 10 mL THF is prepared. This solution is added to 10 mL of n-butylacrylate and mixed thoroughly. A film of this solution spread out on a flat substrate is subjected to UV irradiation and cured to provide a sticky solid.

Example 5: benzyl({3-[(1-chloro-9-oxo-9H-thioxanthen-4-yl)oxy]propyl})bis(2-hydroxyethyl)ammonium bromide

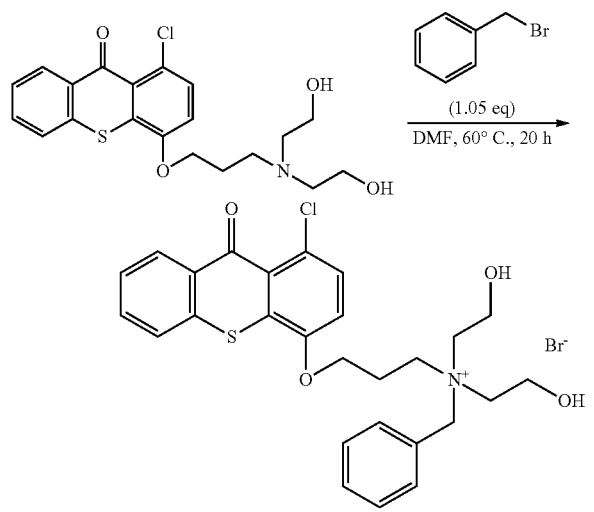

4-{3-[bis(2-hydroxyethyl)amino]propoxy}-1-chloro-9H-thioxanthen-9-one (1.00 g; 2.45 mmol) was dissolved in anhydrous DMF (3 mL) and benzyl bromide (0.4402 g; 2.57 mmol) was added. The homogeneous solution was heated to 60-65° C. for 20 h. After this time, a bright yellow solid precipitates in the reaction mixture. The solvent was removed in vacuo and the crude product was triturated with a hot mixture of 2-butanone (10 mL) and isopropylalcohol (10 mL). After cooling to room temperature, the solid product was filtered off, washed with 2-butanone (10 mL) and dried in vacuo. This provided the desired benzyl({3-[(1-chloro-9-oxo-9H-thioxanthen-4-yl)oxy]propyl})bis(2-hydroxyethyl)ammonium bromide (1.1195 g; 79%) as a yellow solid.

$^1$H-NMR (400 MHz, DMSO-d$_6$): 8.26 (d, J=8.1 Hz, 1H), 7.78-7.67 (m, 4H), 7.58-7.50 (m, 5H), 7.39 (d, J=8.9 Hz, 1H), 5.48 (t, J=4.9 Hz, 2H), 4.85 (s, 2H), 4.33 (t, J=5.7 Hz, 2H), 4.03 (m, 4H), 3.59 (m, 2H), 3.50 (m, 4H), 2.47 (m, 2H).

$^{13}$C-NMR (100 MHz, DMSO-d$_6$): 179.6, 152.1, 135.0, 133.8, 133.3, 130.8, 130.5, 130.3, 129.7, 129.6, 129.3, 128.4, 127.6, 126.9, 126.6, 126.0, 115.1, 67.4, 63.9, 60.7, 57.0, 55.2, 22.7.

Example 6: {3-[(1-chloro-9-oxo-9H-thioxanthen-4-yl)oxy]propyl}bis(2-hydroxyethyl)methylammonium iodide

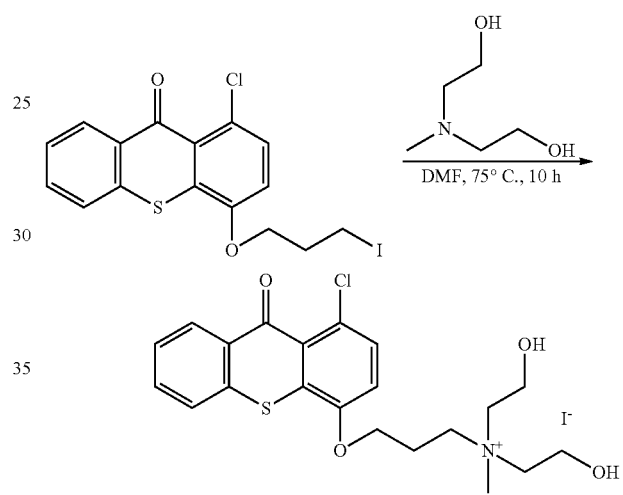

1-chloro-4-(3-iodopropoxy)-9H-thioxanthen-9-one (2.00 g; 4.64 mmol) and N-methyldiethanolamine (0.664 g; 5.57 mmol) were dissolved in anhydrous DMF (10 mL) at 60° C. The reaction mixture was heated to 75° C. for 10 h. Near complete conversion of the starting iodide was checked by TLC (eluent dichloromethane/isopropylalcohol 2:1). The solvent was removed in vacuo and the crude product was triturated with a hot mixture of 2-butanone (10 mL) and isopropylalcohol (10 mL). After cooling to ambient temperature, the crude product was filtered off. The material was further repurified by filtration through a silica plug (eluent methanol and methanol-water 1:1). The collected eluent was evaporated to provide the desired {3-[(1-chloro-9-oxo-9H-thioxanthen-4-yl)oxy]propyl}bis(2-hydroxyethyl)methylammonium iodide as a yellow solid (1.20 g; 47%).

$^1$H-NMR (400 MHz, DMSO-d$_6$): 8.27 (ddd, J=8.1, 1.4, 0.5 Hz, 1H), 7.80 (ddd, J=8.1, 1.5, 0.4 Hz, 1H), 7.76 (ddd, J=8.1, 6.8, 1.4 Hz, 1H), 7.57 (m, 1H), 7.56 (d, J=8.8 Hz, 1H), 7.40 (d, J=8.8 Hz, 1H), 5.32 (t, J=4.9 Hz, 2H), 4.30 (t, J=6.0 Hz, 2H), 3.91 (m, 4H), 3.69-3.65 (m, 2H), 3.57 (m, 4H), 3.21 (s, 3H), 2.32 (m, 2H).

$^{13}$C-NMR (100 MHz, DMSO-d$_6$): 179.0, 151.6, 134.5, 132.7, 129.9, 129.7, 129.2, 128.7, 127.1, 126.4, 125.9, 125.5, 114.5, 66.8, 63.5, 59.5, 54.8, 49.3, 22.0.

Example 7: [3-(4-benzoylphenoxy)propyl]bis(2-hydroxyethyl)methylammonium p-toluenesulfonate

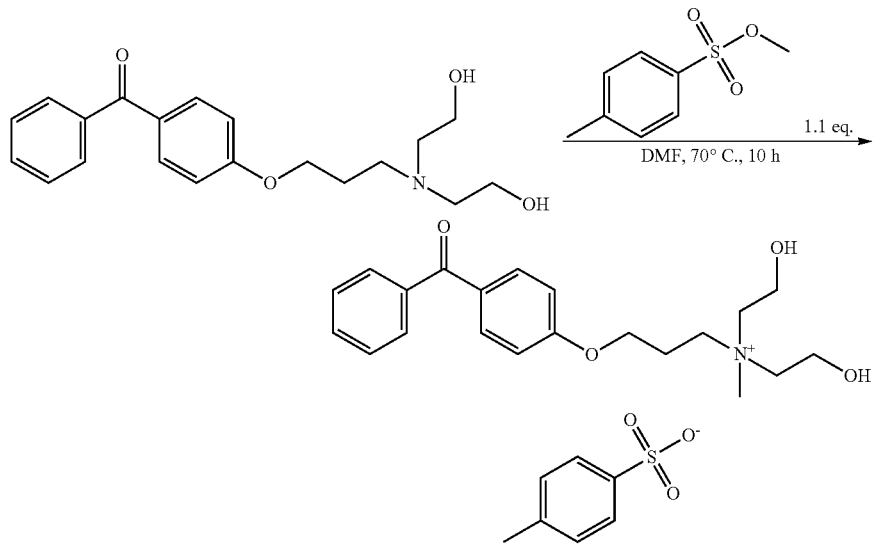

(4-{3-[bis(2-hydroxyethyl)amino]propoxy}phenyl)(phenyl)methanone (5.00 g; 14.6 mmol) and methyl p-toluenesulfonate (2.98 g; 16.0 mmol) were dissolved in anhydrous DMF (25 mL). The reaction mixture was heated to 70° C. for 10 h. The solvent was removed in vacuo to give the crude product as an off-white crystalline mass. The material was recrystallised twice from a hot mixture of 2-butanone (25 mL) and isopropylalcohol (5 mL) to give the desired [3-(4-benzoylphenoxy)propyl]bis(2-hydroxyethyl)methylammonium p-toluenesulfonate (4.79 g; 62%) as white crystals.

$^1$H-NMR (400 MHz, DMSO-$d_6$): 7.75 (d, J=8.8 Hz, 2H), 7.69-7.63 (m, 3H), 7.57-7.51 (m, 4H), 7.12-7.07 (m, 4H), 5.36 (bs, 2H), 4.13 (t, J=6.1 Hz, 2H), 3.87 (m, 4H), 3.62-3.58 (m, 2H), 3.53 (m, 4H), 3.16 (s, 3H), 2.26 (s, 3H), 2.26-2.20 (m, 2H).

$^{13}$C-NMR (100 MHz, DMSO-$d_6$): 194.4, 161.8, 145.3, 137.8, 137.6, 132.14, 132.10, 129.5, 129.2, 128.4, 128.1, 125.4, 114.3, 65.1, 63.4, 59.6, 54.8, 49.1, 22.0, 20.7.

m.p. 136-137° C.

Example 8: Cationic Polyurethane with 10 wt % Photoinitiator Monomer Incorporation A polyurethane polymer was prepared according to method given in Example 2 starting from PEG 600, 4,4'-Methylenebis(cyclohexyl isocyanate) and {3-[bis(2-hydroxyethyl)amino]propoxy}benzophenone (from Preparatory Example 1) so that the content of {3-[bis(2-hydroxyethyl)amino]propoxy}benzophenone in the polyurethane polymer was 10% by weight.

$^{13}$C-NMR (100 MHz, DMSO-$d_6$): 194.2, 162.4, 155.4, 137.7, 132.0, 129.1, 128.2, 114.1, 69.7, 65.9, 61.7, 59.2, 56.5, 52.9, 50.7, 49.8, 47.1, 33.2, 32.5, 31.6, 30.2, 28.8, 27.5, 26.7. 10.0 g of the polyurethane polymer was dissolved in anhydrous DMF (30 mL) and methyl p-toluenesulfonate (2.00 g) was added. The viscous reaction mixture was heated to 90-95° C. for 32 h. DMF was removed on rotary evaporator at 70° C. under oil pump vacuum to leave a highly viscous semisolid. The crude product was dispersed in water (50 mL) and the resulting emulsion was extracted with dichloromethane (3×25 mL) in order to remove unreacted methyl p-toluenesulfonate. The aqueous emulsion was separated and evaporated under oil pump vacuum to leave the desired cationic polyurethane product as a yellow semisolid.

ATR-IR (Ge crystal): 1714, 1657, 1601, 1497, 1468, 1344, 1281, 1221, 1171, 1116, 1033, 1010.

Example 9: Cationic Polyurethane with 30 wt % Photoinitiator Incorporation

A polyurethane polymer was prepared according to method given in Example 2 starting from PEG 600, 4,4'-Methylenebis(cyclohexyl isocyanate) and {3-[bis(2-hydroxyethyl)amino]propoxy}benzophenone (from Preparatory Example 1) so that the content of {3-[bis(2-hydroxyethyl)amino]propoxy}benzophenone in the polyurethane polymer was 30% by weight.

$^{13}$C-NMR (100 MHz, DMSO-$d_6$): 194.2, 162.4, 155.4, 155.3, 137.7, 132.1, 131.9, 129.1, 129.1, 128.3, 114.1, 72.3, 69.8, 66.0, 66.0, 61.7, 60.7, 59.2, 56.7, 56.5, 53.1, 52.9, 50.8, 50.6, 49.8, 47.1, 33.2, 32.4, 31.7, 31.4, 30.3, 28.8, 27.5, 26.7.

10.0 g of the polyurethane polymer was dissolved in anhydrous DMF (30 mL) and methyl p-toluenesulfonate (3.50 g) was added. The viscous reaction mixture was heated to 90-95° C. for 32 h. DMF was removed on rotary evaporator at 70° C. under oil pump vacuum to leave a highly viscous semisolid. The crude product was dispersed in water (50 mL) and the resulting emulsion was extracted with dichloromethane (3×25 mL) in order to remove unreacted methyl p-toluenesulfonate. The aqueous emulsion was separated and evaporated under oil pump vacuum to leave the desired cationic polyurethane product as a yellow semisolid.

ATR-IR (Ge crystal): 1717, 1656, 1600, 1531, 1495, 1470, 1448, 1281, 1223, 1171, 1121, 1033, 1010.

Example 10: Cationic Polyurethane with 3 wt % Photoinitiator Monomer Incorporation Prepared in Solvent PEG 2000 (5.00 g; 2.50 mmol) was melted and heated to 90° C. for 2 hours under vacuum to remove residual moisture. The reaction mixture was cooled to ambient temperature and [3-(4-benzoylphenoxy)propyl]bis(2-hydroxyethyl)methylammonium iodide (0.1695 g; 0.349 mmol) and anhydrous DMF (5 mL) were added. The reaction mixture was fully homogenised by mixing at 60° C. and then hexamethylene diisocyanate (0.4792 g; 2.849 mmol) was added followed by dibutyltin dilaurate (0.01 g; 15.8 mol). The reaction vial was sealed, the content was thoroughly mixed and the mixture was heated to 90° C. for 2.5 h. A highly viscous liquid is obtained. Upon cooling to ambient temperature, the reaction mass was dissolved in methanol (25 mL), transferred to a round bottom flask and all solvents were removed in vacuo to provide the product as a white elastic solid.

ATR-IR (Ge crystal; cm$^{-1}$): 2878, 1718, 1672, 1545, 1533, 1468, 1389, 1280, 1253, 1242, 1146, 1105, 1062, 962, 948, 843.

Example 11: Cationic Polyurethane with 30 wt % Photoinitiator Monomer Incorporation Prepared in Solvent PEG 2000 (5.00 g; 2.50 mmol) was melted and heated to 90° C. for 2 hours under vacuum to remove residual moisture. The reaction mixture was cooled to ambient temperature and [3-(4-benzoylphenoxy)propyl]bis(2-hydroxyethyl)methylammonium iodide (2.7282 g; 5.62 mmol) and anhydrous DMF (10 mL) were added. The reaction mixture was fully homogenised by mixing at 60° C. and then hexamethylene diisocyanate (1.3659 g; 8.12 mmol) was added followed by dibutyltin dilaurate (0.01 g; 15.8 mol). The reaction vial was sealed, the content was thoroughly mixed and the mixture was heated to 90° C. for 2.5 h. The highly viscous liquid reaction mass was dissolved in methanol (25 mL), transferred to a round bottom flask and all solvents were removed in vacuo to provide the product as an off-white tough elastic solid.

ATR-IR (Ge crystal; cm$^{-1}$): 2877, 1720, 1668, 1600, 1531, 1467, 1441, 1389, 1346, 1281, 1254, 1145, 1096, 941.

Example 12: UV Photocrosslinking of a Cationic Polyurethane Coating

Cationic polyurethane prepared in Example 10 (250 mg) was dissolved in methanol (2.0 mL). The solution was coated onto a sheet of PVC using a K-bar (200 μm thickness). The obtained film was dried at 80° C. for 5 minutes to remove the solvent. Rub test prior to UV irradiation indicated that the film is fully soluble in methanol and water. The film was UV cross-linked by passing under 900 W high pressure mercury lamp (Dymax UV-5 conveyor curing system, UV light intensity 7.5 W/cm$^2$, conveyor belt speed 16.5 m/s). The results in Table 3 show the effects of UV curing. Film resistance was tested with tissue paper double rubs (i.e. a rub back and fort) using methanol and water. The numbers indicate double rubs required for failure or breakthrough of the film to occur.

TABLE 3

Solvent resistance of a UV cured cationic polyurethane film

| Number of | MeOH double | water double |
|---|---|---|
| 0 lamp passes | soluble | soluble |
| 2 lamp passes | 20 | >200 |
| 4 lamp passes | 40 | >200 |
| 8 lamp passes | 50 | >200 |

Example 13: Acrylate Polymerisation Initiated by Cationic Polyurethane Photoinitiators A vial was charged with 2.0 g trimethylolpropane ethoxylate triacrylate (avg. Mn~912; 14/3 EO/OH), 2.0 g water and 100 mg of cationic polyurethane photoinitiator. The mixture was stirred vigorously until a stable emulsion was obtained. The emulsion was coated onto an acrylic panel using a K-bar (100 μm thickness). The obtained aqueous film was directly cured by passing under 900 W high pressure mercury lamp (Dymax UV-5 conveyor curing system, UV light intensity 7.5 W/cm$^2$, conveyor belt speed 16.5 m/s). The qualitative results for different cationic polyurethane photoinitiator are shown in Table 4.

TABLE 4

Results of acrylate polymerisation using polyurethane photoinitiators.

| Polymeric Photoinitiator | number of passes | result |
|---|---|---|
| control (no photoinitiator) | 20 | no cure |
| Polymer from Example 11 | 20 | acetone insoluble film |
| Polymer from Example 9 | 10 | acetone insoluble film |
| Polymer from Example 8 | 10 | acetone insoluble film |

It was noted during the experiments that the polymer solution of example 11 was more viscous than the ones for examples 8 or 9. It is believed that the higher the molecular weight of the polymer, the more viscous solution and the less mobility during acrylate polymerization. Example 8 and 9, which are made by quaternising the already formed polymeric photoinitiator, seem to provide an advantage of lower molecular weight with more mobility leading to a higher double bond conversion during the acrylate polymerization, and hence requires less UV irradiation. When the quaternary polymeric photoinitiators are prepared from quaternisation of already prepared tertiary amine polymeric photoinitiators (as examples 8 and 9) these may therefore advantageously be used for acrylate polymerization when an insoluble acrylate film is desired.

Example 14: UV Self-Crosslinking of Cationic Polyurethanes

A sample of polyurethane cationomer (0.5 g) was dissolved/dispersed in methanol (2.5 g). The liquid mixture was coated onto an acrylic panel using a K-bar (100 μm thickness). The coated panels were warmed to 90° C. for 2 minutes in order to remove solvent from the coated films. The films were irradiated by passing under 900 W high pressure mercury lamp (Dymax UV-5 conveyor curing system, UV light intensity 7.5 W/cm$^2$, conveyor belt speed 16.5 m/s). The results in Table 5 show the effects of UV curing.

TABLE 5

Results of self-crosslinking of polyurethanes under UV light

| Polymer sample | number of passes | result |
|---|---|---|
| Example 11 | 2 | water and acetone insoluble film |
| Example 9 | 8 | soft partially water soluble film |
| Example 8 | 8 | soft partially water soluble film |
| Polymer from Table 2, entry 6 | 2 | water and acetone insoluble film |

TABLE 5-continued

Results of self-crosslinking of polyurethanes under UV light

| Polymer sample | number of passes | result |
|---|---|---|
| Polymer from Example 8 before quaternisation | 8 | water and acetone insoluble film |
| Polymer from Example 9 before quaternisation | 8 | soft partially water soluble film |

As noted in Example 13, the polymer from Example 11 is more viscous, indicating a higher molecular weight. Even if the percentage of photoinitiator monomer in Example 11 and Example 9 are both 30%, then Example 11 having a higher molecular weight will have more photoinitiators on each polymer molecule and hence more sites where crosslinking can occur during UV irradiation. Therefore less irradiation is needed to provide an insoluble film as opposed to a smaller molecule with less photoinitiator sites. When the quaternary polymeric photoinitiators are prepared from quaternary monomers (as example 11) these therefore advantageously can be used when self-crosslinking is to be relied upon for insoluble film formation.

Example 15: Solubility Comparison 100 mg of polyurethane sample was placed in a vial and appropriate amount of solvent was added. The vial was stirred at ambient temperature (20° C.) overnight or warmed with a hot air gun to 60° C. for 10 minutes. The qualitative solubility of the sample was then judged based on residual undissolved material in the vial. The results are given in Table 6.

Table 6 also gives the molar fraction of content of the —C(=O)—NH— moiety in millimoles per gram as part of the polyurethane polymer.

TABLE 6

Qualitative solubility comparison

| Polyurethane sample | methanol solubility | water solubility | —C(=O)—NH— moiety content |
|---|---|---|---|
| Polymer from Example 11 | soluble at 20 wt % at 20° C. | soluble at 10 wt % at 20° C. | 1.79 mmol/g |
| Polymer from Table 1, entry 13 | insoluble | insoluble | 3.28 mmol/g |
| Polymer from Preparatory Example 8 | sparingly soluble at 60° C. | insoluble | 1.96 mmol/g |
| Polymer from Example 9 | sparingly soluble at 60° C. | sparingly soluble at 60° C. | 2.84 mmol/g |
| Polymer from Example 8 | soluble at 20 wt % at 60° C. | soluble at 20 wt % at 20° C. | 2.49 mmol/g |

It can be noted that the polymer from Example 11 (Table 6, Entry 1), which contains 30 wt % of quaternary ammonium photoinitiator monomer, shows much higher solubility in both methanol and water compared to polymer from Preparatory Example 8 (Table 6, Entry 3). Both polymers were prepared under identical conditions, and the molar ratios of the monomers were kept the same (the —C(=O)—NH— moiety content differs slightly for the two, this is due to an increased total Mw of Ex. 11 due to the extra $R^1$ moiety on the ammonium group). The solubility increase can therefore be attributed to the presence of quaternary ammonium moieties in the polymer chain.

Typically, the urethane moieties of PU polymers will engage in strong intermolecular hydrogen bonding which in turn tends to reduce solubility of the polymer. From Table 6 the —C(=O)—NH— moiety content can be seen; when comparing the polymer from Example 8 (quaternary) it is noted that, even if it has a higher urethane moiety content compared to the polymer from Preparatory Example 8 (non-quaternary), it shows a much higher solubility in both methanol and water. The solubility difference may therefore be attributed to the presence of quaternary ammonium moieties in the polymer from Example 8 as opposed to the polymer from Preparatory Example 8, which has no cationic moieties.

Example 16: Solubility Comparison of Monomeric Photoinitiators 100 mg of photoinitiator monomer sample was placed in a vial and appropriate amount of solvent was added. The vial was stirred at ambient temperature (20° C.) overnight or warmed with a hot air gun to 60° C. for 10 minutes. The qualitative solubility of the sample was then judged based on residual undissolved material in the vial.

TABLE 7

Qualitative solubility comparison

| Photoinitator monomer sample | water solubility |
|---|---|
| Photoinitiator monomer from Preparatory Example 1 | sparingly soluble at 100° C. |
| Photoinitiator monomer from Preparatory Example 2 | sparingly soluble at 100° C. |
| Photoinitiator monomer from Example 1 | soluble at 10 wt % at 20° C. |
| Photoinitiator monomer from Example 7 | soluble at 10 wt % at 40° C. |
| Photoinitiator monomer from Example 6 | soluble at 5 wt % at 60° C. |

Although the invention has been described with reference to a number of examples and reaction schemes, it should not be considered as limited by the above description. The full scope of the invention is defined by the appended claims.

The invention claimed is:

1. A polymeric photoinitiator, comprising a co-polymer of at least one monomer (A) with at least one monomer (B), wherein:

monomer (A) is a photoinitiator monomer (A) comprising formula (I):

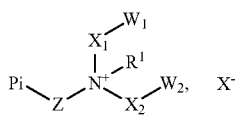

(I)

wherein:
Pi is a photoinitiator moiety;
Z is a linker moiety, wherein Z is selected from the group consisting of a single bond, an optionally substituted $C_1$-$C_{12}$ alkylene, an optionally substituted $C_2$-$C_{12}$ an alkenylene, —O—, —S—, —$NR^2$—, —C(=O)—, —C(=O)—$NR^7$—, —$NR^7$—C(=O)—, —C(=$NR^7$)—, —$SO_2$—, —P(=O)($OR^7$)—, an optionally substituted —$C_3$-$C_8$ cycloalkyl, an optionally substituted heterocyclyl, an optionally substituted aryl, —[O—($C_1$-$C_{12}$ alkylene)]$_n$-, —[$NR^2$—($C_1$-$C_{12}$ alkylene)]$_n$-, —[S—($C_1$-$C_{12}$ alkylene)]$_n$-, and combinations thereof, wherein $R^2$ is an optionally substituted $C_1$-$C_{12}$ alkyl, $R^7$ is H or an optionally substituted $C_1$-$C_{12}$ alkyl, and n is an integer from 1-20;
$R^1$ is selected from an optionally substituted $C_1$-$C_{30}$ alkyl, an optionally substituted $C_3$-$C_{30}$ alkenyl, an optionally substituted $C_3$-$C_{30}$ alkynyl, an optionally substituted $C_3$-$C_{12}$ cycloalkyl, an optionally substituted —[($C_1$-$C_6$ alkylene)-O—($C_1$-$C_6$ alkylene)]$_p$-H moiety, an optionally substituted heterocyclyl, and an optionally substituted aryl;
p is an integer from 1-6;
$X_1$ and $X_2$ are each independently selected from an optionally substituted $C_1$-$C_{12}$ alkylene, an optionally substituted $C_2$-$C_{12}$ alkenylene, —O—, —S—, —$NR^4$—, —C(=O)—, —C(=$NR^3$)—, —Si($R^3$)$_2$—O—, an optionally substituted $C_3$-$C_8$ cycloalkyl, an optionally substituted heterocyclyl, an optionally substituted aryl, and combinations thereof;
$X_1$ and $X_2$ or a part thereof may be linked to one another or to linker Z or $R^1$, to form one or more ring structures;
Z, $R^1$, $X_1$ and $X_2$ are selected such that N is a quaternary ammonium;
$R^3$ is H or an optionally substituted $C_1$-$C_{12}$ alkyl;
$R^4$ is an optionally substituted $C_1$-$C_{12}$ alkyl;
$X^-$ is a counterion, or a negatively charged moiety that is associated with any carbon atom of Pi, Z, $R^1$, $X_1$, $X_2$ or their optional substituents, to form a betaine-type structure;
$W_1$ and $W_2$ are each independently selected from —OH, —$CH_2OH$, —$NH_2$, —$NHR^6$, —SH, —Si($OR^6$)$_2$—H, —SiH($R^6$)$_2$, —C(=O)—OSi($R^6$)$_3$, —NCO, —NCS, —COOH, —$COOR^6$, —COO-aryl, —C(=O)—Cl, —O—C(=O)—Cl, —C(O)—$NH_2$, —C(O)—$NHR^5$, —NH—C(O)—$OR^5$, and —OC(O)—$NHR^5$;
$R^5$ is H or a $C_1$-$C_6$ alkyl;
$R^6$ is a $C_1$-$C_6$ alkyl;
monomer (B) comprises formula (VI):

$W_3$-Q-$W_4$ (VI)

wherein $W_3$ and $W_4$ are each independently selected from halogen, —OH, —$CH_2OH$, —$NH_2$, —$HNR^{10}$, —SH, Si($OR^{10}$)$_2$—H, —SiH($R^{10}$)$_2$, —C(=O)—OSi($R^{10}$)$_3$, —NCO, —NCS, —COOH, $COOR^{10}$, —C)—)aryl, —C(=O)—Cl, —O—C=O—)Cl, —C(O)—$NH_2$, —C(O)—$NHR^9$, —NH—C(O)—$OR^9$ and —OC(O)—$NHR^9$, wherein $R^9$ is H or a $C_1$-$C_6$ alkyl and $R^{10}$ is a $C_1$-$C_6$ alkyl;
Q is selected from the group consisting of an optionally substituted $C_1$-$C_{12}$ alkylene, an optionally substituted $C_2$-$C_{12}$ alkenylene, an optionally substituted $C_3$-$C_8$ cycloalkyl, an optionally substituted $C_3$-$C_{12}$ heterocyclyl, an optionally substituted aryl, an optionally substituted biaryl, and combinations thereof, or optionally Q can be a Pi; and
wherein $W_1$, $W_2$, $W_3$ and $W_4$ are selected such that (A) and (B) react such that $W_1$ reacts with $W_3$ to from a urethane, a thiourethane, a urea, a thiourea, an ester, an ether, an amide, a carbonate, an allophanate, or a biuret moiety and $W_2$ reacts with $W_4$ to form a urethane, a thiourethane, a urea, a thiourea, an ester, an ether, an amide, a carbonate, an allophanate, or a biuret moiety.

2. The polymeric photoinitiator according to claim 1, wherein n is an integer from 1-10.

3. The polymeric photoinitiator according to claim 1, wherein Z is selected from a single bond, an optionally substituted $C_1$-$C_{12}$ alkylene, an optionally substituted $C_2$-$C_{12}$ alkenylene, —O—, —S—, —$NR^2$—, —C(=O)—, —C(=O)—$NR^7$—, —$NR^7$—C(=O)—, —C(=$NR^7$)—, an optionally substituted —$C_3$-$C_8$ cycloalkyl, an optionally substituted heterocyclyl, an optionally substituted aryl, —[O—($C_1$-$C_{12}$ alkylene)]$_n$—, —[$NR^2$—($C_1$-$C_{12}$ alkylene)]$_n$-, —[S—($C_1$-$C_{12}$ alkylene)]$_n$-, and combinations thereof, wherein $R^2$ is an optionally substituted $C_1$-$C_{12}$ alkyl, $R^7$ is H or an optionally substituted $C_1$-$C_{12}$ alkyl, and n is an integer from 1-20.

4. The polymeric photoinitiator, according to claim 1, wherein formula (I) comprises formula (II) wherein Z is -Za-Zb-:

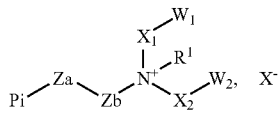

(II)

wherein:
Pi is a photoinitiator moiety;
Za and Zb together form a single bond, or a linker in which Za is selected from an optionally substituted —[O—($C_1$-$C_{12}$ alkylene)]$_n$-, an optionally substituted —[$NR^2$—($C_1$-$C_{12}$ alkylene)]$_n$-, and an optionally substituted —[S—($C_1$-$C_{12}$ alkylene)]$_n$-, wherein Za is joined to Pi via the O, N or S atom in Za, and Zb is a linker moiety;
Zb is selected from a single bond, an optionally substituted $C_1$-$C_{12}$ alkylene, an optionally substituted $C_2$-$C_{12}$ alkenylene, —O—, —S—, —$NR^2$—, —C(=O)—, —C(=O)—$NR^7$—, —$NR^7$—C(=O)—, —C(=$NR^7$)—, —$SO_2$—, —P(=O)($OR^7$)—, an optionally substituted $C_3$-$C_8$ cycloalkyl, an optionally substituted heterocyclyl, an optionally substituted aryl, an optionally substituted —[O—($C_1$-$C_{12}$ alkylene)]$_n$-, an optionally substituted —[$NR^2$—($C_1$-$C_{12}$ alkylene)]$_n$-, an optionally substituted;

—[S—($C_1$-$C_{12}$ alkylene)]$_n$-, and combinations thereof, wherein $R^2$ is an optionally substituted $C_1$-$C_{12}$ alkyl, $R^7$ is H or an optionally substituted $C_1$-$C_{12}$ alkyl, and n is an integer from 1-20

$R^1$ is selected from an optionally substituted $C_1$-$C_{30}$ alkyl, an optionally substituted $C_3$-$C_{30}$ alkenyl, an optionally substituted $C_3$-$C_{30}$ alkynyl, an optionally substituted $C_3$-$C_{12}$ cycloalkyl, an optionally substituted —[($C_1$-$C_6$ alkylene)-O—($C_1$-$C_6$ alkylene)]$_p$-H moiety, an optionally substituted heterocyclyl, and an optionally substituted aryl;

$R^2$ is an optionally substituted $C_1$-$C_{12}$ alkyl;

n is an integer from 1-20;

p is an integer from 1-6;

$X_1$ and $X_2$ are each independently selected from an optionally substituted $C_1$-$C_{12}$ alkylene, an optionally substituted $C_2$-$C_{12}$ alkenylene, —O—, —S—, —$NR^4$—, —C(=O)—, —C(=$NR^3$)—, —Si($R^3$)$_2$—O—, an optionally substituted $C_3$-$C_8$ cycloalkyl, an optionally substituted heterocyclyl, an optionally substituted aryl, and combinations thereof;

$X_1$ and $X_2$ or a part thereof may be linked to one another or to linkers Za or Zb, or $R^1$ to form one or more ring structures;

Za, Zb, $R^1$, $X_1$ and $X_2$ are selected such that N is a quaternary ammonium;

$R^3$ is H or an optionally substituted $C_1$-$C_{12}$ alkyl;

$R^4$ is an optionally substituted $C_1$-$C_{12}$ alkyl;

$X^-$ is a counterion, or a negatively charged moiety that is associated with any carbon atom of Pi, Za, Zb, $R^1$, $X_1$, $X_2$ or their optional substituents to form a betaine-type structure;

$W_1$ and $W_2$ are each independently selected from —OH, —$CH_2OH$, —$NH_2$, —$NHR^6$, —SH, —Si($OR^6$)$_2$—H, —SiH($R^6$)$_2$, —C(=O)—OSi($R^6$)$_3$, —NCO, —NCS, —COOH, —$COOR^6$, —COO-aryl, —C(=O)—Cl, —O—C(=O)—Cl, —C(O)—$NH_2$, —C(O)—$NHR^5$, —NH—C(O)—$OR^5$, and —OC(O)—$NHR^5$;

$R^5$ is H or a $C_1$-$C_6$ alkyl; and $R^6$ is a $C_1$-$C_6$ alkyl.

5. The polymeric photoinitiator according to claim 4, wherein n is an integer from 1-10.

6. The polymeric photoinitiator according to claim 4, wherein Za is selected from —[O—($C_1$-$C_6$ alkylene)]$_n$-, —[$NR^2$—($C_1$-$C_6$ alkylene)]$_n$-, —[S—($C_1$-$C_6$ alkylene)]$_n$-, —O—($C_1$-$C_6$ alkylene)-$NR^2$—($C_1$-$C_6$ alkylene)-, —$NR^2$—($C_1$-$C_6$ alkylene)-O—($C_1$-$C_6$ alkylene)-, —S—($C_1$-$C_6$ alkylene)-O—($C_1$-$C_6$ alkylene)-, —O—($C_1$-$C_6$ alkylene)-S—($C_1$-$C_6$ alkylene)-, —S—($C_1$-$C_6$ alkylene)-$NR^2$—($C_1$-$C_6$ alkylene)-, and —$NR^2$—($C_1$-$C_6$ alkylene)-S—($C_1$-$C_6$ alkylene)-, wherein the $C_1$-$C_6$ alkylene optionally is substituted with one or more substituents, wherein the $R^2$ is $C_1$-$C_6$ alkyl, and n is an integer from 1-2.

7. The polymeric photoinitiator according to claim 1, wherein $W_1$ and $W_2$ are independently selected from —OH, —$CH_2OH$, —$NH_2$, —$NHR^5$, —SH, —NCO, —NCS, and —COOH.

8. The polymeric photoinitiator according to claim 1, wherein $W_1$ and $W_2$ are the same.

9. The polymeric photoinitiator according to claim 1, wherein $R^1$ is selected from an optionally substituted $C_1$-$C_{20}$ alkyl, an optionally substituted $C_3$-$C_{20}$ alkenyl, an optionally substituted $C_3$-$C_{20}$ alkynyl, and an optionally substituted —[($C_1$-$C_6$ alkylene)-O—($C_1$-$C_6$ alkylene)]$_p$-H moiety; wherein p is an integer from 1-2.

10. The polymeric photoinitiator according to claim 1, wherein $X^-$ is a counterion selected from fluoride, chloride, bromide, iodide, sulfate, carbonate, phosphate, tetrafluoroborate, tetraarylborate, hexafluorophosphate, alkyl carboxylate, aryl carboxylate, alkyl sulfonate and aryl sulfonate.

11. The polymeric photoinitiator according to claim 1, wherein $X^-$ is a negatively charged moiety that is associated with any carbon atom of Pi, Z, Za, Zb, $R^1$, $X_1$, $X_2$ or their optionally substituents to form a betaine-type structure.

12. The polymeric photoinitiator according to claim 1, wherein $X_1$ and $X_2$ are each independently an optionally substituted $C_1$-$C_{12}$ alkylene.

13. The polymeric photoinitiator according to claim 1, wherein $X_1$ and/or $X_2$ is attached to the N atom of the quaternary ammonium branching group through a —$CH_2$— group.

14. The polymeric photoinitiator according to claim 1, wherein $X_1$ and $X_2$ are the same.

15. The polymeric photoinitiator according to claim 1, wherein $X_1$ and $X_2$ are independently selected from an optionally substituted $C_1$-$C_{12}$ alkylene, and $W_1$ and $W_2$ are —$CH_2OH$.

16. The polymeric photoinitiator according to claim 1, wherein one or more optional substituents are selected from the group consisting of —F, —Cl, —Br, —I, —CN, —$NO_2$, —$C_1$-$C_6$ alkyl, —$C_2$-$C_6$ alkenyl, —$C_3$-$C_6$ cycloalkyl, aryl, heterocyclyl, —O—($C_1$-$C_6$ alkyl), —O—$C_3$-$C_8$ cycloalkyl, —O-aryl, —C(O)—($R^8$), —C(O)-aryl, —C(O)O—($C_1$-$C_6$ alkyl), —C(O)O-aryl, —O—C(O)-aryl, —O—C(O)—O—($C_1$-$C_6$ alkyl), —O—C(O)—O-aryl, —N($C_1$-$C_6$alkyl)$_2$, —N($C_1$-$C_6$alkyl)($C_3$-$C_6$ cycloalkyl), —N($C_1$-$C_6$alkyl)(aryl), —N(aryl)$_2$, —N($R^8$)—C(O)—($C_1$-$C_6$ alkyl), —N($R^8$)—C(O)-aryl, —C(O)—N(R)$_2$, —C(O)—N($R^8$)-aryl, —C(O)—N(aryl)$_2$, —O—C(O)—N(R)$_2$, —O—C(O)—NH—($C_1$-$C_6$aryl), —N($R^8$)—C(O)—O—($C_1$-$C_6$alkyl), —NH—C(O)—O—($C_1$-$C_6$aryl), —S(O)—($C_1$-$C_6$ alkyl), —S(O)-aryl, —$SO_2$—($C_1$-$C_6$ alkyl), —$SO_2$-aryl, —S—($C_1$-$C_6$ alkyl) and —S-aryl; wherein $R^8$ is H or $C_1$-$C_6$ alkyl.

17. The polymeric photoinitiator according to claim 1, wherein Pi is a photoinitiator moiety selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, camphorquinones, silane and derivatives thereof, and maleimides.

18. The polymeric photoinitiator according to claim 1, wherein Pi is a photoinitiator moiety selected from benzophenones, thioxanthones, benzilketals and phenyl hydroxyalkyl ketones.

19. The polymeric photoinitiator according to claim 1, wherein Pi is a non-cleavable photoinitiator.

20. The polymeric photoinitiator according to claim 1, wherein formula (I) comprises formula (IIIa):

(IIIa)

$$Ar_1-C(=O)-Ar_2-Z-N^+(X_1-W_1)(X_2-W_2)(R^1), \quad X^-$$

wherein Ar₁ and Ar₂ are each independently selected from the same or different aryl, where Z may be present at any position on Ar₂, and where each aryl independently may be optionally substituted with one or more substituents selected from the substitutents defined in claim 16.

21. The polymeric photoinitiator according to claim 20, wherein Ar₁ and Ar₂ each independently are an optionally substituted phenyl.

22. The polymeric photoinitiator according to claim 20, wherein Z is present at the para-position on Ar₂.

23. The polymeric photoinitiator according to claim 1, wherein formula (I) comprises formula (IV):

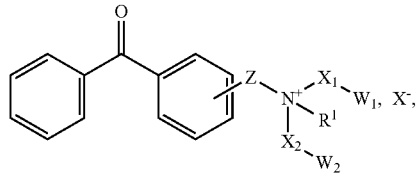

(IV)

wherein Z, R¹, X⁻, X₁, X₂, W₁ and W₂ are as defined in claim 1, and wherein the aromatic rings of formula (IV) may each independently be optionally substituted.

24. The polymeric photoinitiator according to claim 1, wherein formula (I) comprises formula (V):

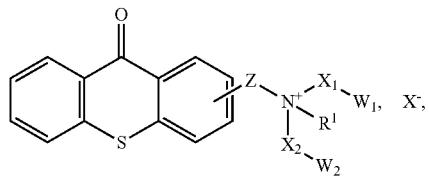

(V)

wherein Z, R¹, X⁻, X₁, X₂, W₁ and W₂, are as defined in claim 1, and wherein the aromatic rings of formula (V) may each independently be optionally substituted.

25. The polymeric photoinitiator according to claim 1, wherein formula (I) comprises formula (IVa):

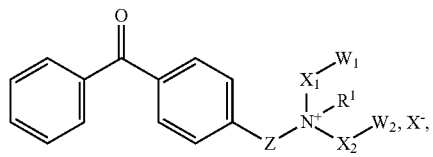

(IVa)

wherein Z, R¹, X⁻, X₁, X₂, W₁ and W₂ are as defined in claim 1, and wherein the aromatic rings each independently may be optionally substituted.

26. The polymeric photoinitiator according to claim 1, wherein the photoinitiator monomer (A) is selected from the group consisting of:
4-({[(4-benzoylphenyl)methyl]bis(2-hydroxyethyl)ammoniumyl}methyl)benzoate;
[(4-benzoylphenyl)methyl]bis[2-(2-hydroxyethoxy)ethyl]methylammonium bromide;
[2-(4-benzoylphenyl)-2-oxoethyl]bis(2-hydroxyethyl)methylammonium bromide;
[2-(2-benzoylbenzoyloxy)ethyl]bis(2-hydroxyethyl)methylammonium bromide;
[3-(4-benzoylphenoxy)propyl]bis(2-hydroxyethyl)methylammonium bromide;
[3-(4-benzoylphenoxy)propyl](benzyl)bis(2-hydroxyethyl)ammonium bromide;
3-{[3-(4-benzoylphenoxy)propyl]bis(2-hydroxyethyl)ammonium}propane-1-sulfonate;
{2-[(4-benzoylphenyl)sulfanyl]ethyl}(ethyl)bis(2-hydroxyethyl)ammonium iodide;
[2-(4-benzoylphenoxy)ethyl]bis(2-hydroxypropyl)methylammonium 4-methylbenzene-1-sulfonate;
2-{[2-(4-benzoylphenoxy)ethyl]bis(2-hydroxyethyl)ammoniumyl}ethane-1-sulfonate;
2-[bis(2-aminoethyl)[3-(4-benzoylphenoxy)propyl]ammoniumyl]acetate;
{3-[(1-chloro-9-oxo-9H-thioxanthen-4-yl)oxy]propyl}bis(2-hydroxyethyl)methylammonium bromide;
{3-[(1-chloro-9-oxo-9H-thioxanthen-4-yl)oxy]propyl}bis(2-hydroxyethyl)ethylammonium iodide;
2-({3-[(1-chloro-9-oxo-9H-thioxanthen-4-yl)oxy]propyl}bis(2-hydroxyethyl)ammoniumyl)ethane-1-sulfonate;
bis(2-hydroxyethyl)methyl[2-({2-[(9-oxo-9H-thioxanthen-2-yl)oxy]acetyl}oxy)ethyl]ammonium chloride;
(cyanomethyl)({2-[4-(2-hydroxy-2-methylpropanoyl)phenoxy]ethyl})bis(2-hydroxyethyl)ammonium 4-bromobenzene-1-sulfonate; and
benzyl({3-[(1-chloro-9-oxo-9H-thioxanthen-4-yl)oxy]propyl})bis(2-hydroxyethyl)ammonium bromide.

27. The polymeric photoinitiator according to claim 1, wherein W₃ and W₄ are each independently selected from isocyanate and thioisocyanate groups.

28. The polymeric photoinitiator according to claim 1, wherein monomer (B) is selected from the group consisting of: 1,4-phenylene diisocyanate (PPDI), toluene diisocyanate (TDI), methylene diphenyl diisocyanate (MDI), 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI), and 1,3-bis(isocyanato-methyl)cyclohexane (HXDI).

29. The polymeric photoinitiator according to claim 1, wherein both W₁ and W₂ are alcohol functional groups and both W₃ and W₄ are isocyanate functional groups.

30. The polymeric photoinitiator according to claim 1, further comprising one or more additional monomers (C), wherein monomer (C) has the structure of formula (VII):

$$W_5\text{-}T\text{-}W_6 \quad (VII)$$

herein T is selected from the group consisting of an optionally substituted $C_1$-$C_{12}$ alkylene, an optionally substituted $C_1$-$C_{12}$ alkenylene, an optionally substituted $C_3$-$C_8$ cycloalkyl, an optionally substituted $C_3$-$C_{12}$ heterocyclyl, an optionally substituted aryl, an optionally substituted biaryl, and combinations thereof; wherein each of said one or more additional monomers (C) comprises at least two functional groups W₅ and W₆, said W₅ and W₆ being independently selected from —OH, —CH₂OH, —NH₂, —NHR¹², —SH, —Si(OR¹²)₂—H, —C(=O)—OSi(R¹²)₃, —SiH(R¹²)₂, —NCO, —NCS, —COOH, —COOR¹², —COO-aryl, —C(=O)—Cl, —O—C(=O)—Cl, —C(O)—NH₂, —C(O)—NHR$^{11}$, —NH—C(O)—OR$^{11}$, and —OC(O)—NHR$^{11}$, wherein R$^{11}$ is H or $C_1$-$C_6$ alkyl, and wherein R$^{12}$ is $C_1$-$C_6$ alkyl;

wherein $W_5$ and $W_6$ are selected such $W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety.

31. The polymeric photoinitiator according to claim 30, wherein $W_5$ and $W_6$ are independently selected from —OH, —CH$_2$OH, —NH$_2$, —NHR$^{12}$, and —SH.

32. The polymeric photoinitiator according to claim 1, wherein the weight ratio of monomers (A):(B) is 1:99-99:1.

* * * * *

UNITED STATES PATENT AND TRADEMARK OFFICE
CERTIFICATE OF CORRECTION

PATENT NO. : 10,040,893 B2
APPLICATION NO. : 14/401126
DATED : August 7, 2018
INVENTOR(S) : Niels Joergen Madsen et al.

Page 1 of 1

It is certified that error appears in the above-identified patent and that said Letters Patent is hereby corrected as shown below:

In the Claims

Claim 1 at Column 80, Line 17 "to from" should read -- to form --

Claim 16 at Column 82, Line 32 "—C(O)—N(R)$_2$" should read -- —C(O)—N(R$^8$)$_2$ --

Claim 16 at Column 82, Line 33 "—O—C(O)—N(R)$_2$" should read -- —O—C(O)—N(R$^8$)$_2$ --

Signed and Sealed this
Twelfth Day of February, 2019

Andrei Iancu
*Director of the United States Patent and Trademark Office*